US012605115B2

(12) United States Patent
Wendler et al.

(10) Patent No.: US 12,605,115 B2
(45) Date of Patent: Apr. 21, 2026

(54) SENSOR ARRAYS, METHOD FOR OPERATING A SENSOR ARRAY AND A COMPUTER PROGRAM FOR PERFORMING A METHOD FOR OPERATING A SENSOR ARRAY

(71) Applicant: Albert-Ludwigs-Universität Freiburg, Freiburg (DE)

(72) Inventors: Daniel Wendler, Bad Krozingen (DE); Daniel De Dorigo, Freiburg (DE); Yiannos Manoli, Freiburg (DE)

(73) Assignee: Albert-Ludwigs-Universität Freiburg, Freiburg (DE)

( * ) Notice: Subject to any disclaimer, the term of this patent is extended or adjusted under 35 U.S.C. 154(b) by 248 days.

(21) Appl. No.: 18/363,892

(22) Filed: Aug. 2, 2023

(65) Prior Publication Data

US 2023/0389877 A1     Dec. 7, 2023

Related U.S. Application Data

(63) Continuation of application No. PCT/EP2021/080979, filed on Nov. 8, 2021.

(30) Foreign Application Priority Data

Feb. 4, 2021    (EP) .................................... 21155294

(51) Int. Cl.
   *A61B 5/00*        (2006.01)
   *A61B 5/262*       (2021.01)
       (Continued)

(52) U.S. Cl.
   CPC ............ *A61B 5/6848* (2013.01); *A61B 5/262* (2021.01); *A61B 5/291* (2021.01); *A61B 5/31* (2021.01);
       (Continued)

(58) Field of Classification Search
   CPC ......... A61B 5/293; A61B 5/302; A61B 5/305; A61B 5/51; A61B 5/685; A61B 5/6868
   See application file for complete search history.

(56)          References Cited

U.S. PATENT DOCUMENTS 4,839,649 A      6/1989  Imai et al.
5,410,310 A      4/1995  Molnar
              (Continued)

FOREIGN PATENT DOCUMENTS

CN        103378861 A     10/2013
CN        109645978 A      4/2019
              (Continued)

OTHER PUBLICATIONS

B. C. Raducanu et al., "Time Multiplexed Active Neural Probe with 678 Parallel Recording Sites", IEEE ESSDERC, pp. 385-388, 2016.
              (Continued)

*Primary Examiner* — Eun Hwa Kim
(74) *Attorney, Agent, or Firm* — Bridgeway IP Law Group, PLLC; Jihun Kim

(57)          ABSTRACT

A sensor array comprises a base for providing a probe signal and a plurality of modular recording sites. Each modular recording site of the plurality of modular recording sites is configured for receiving a signal, for converting the signal into a digital sensor signal using an in-situ analog-to-digital converter and to provide the digital sensor signal to the base using a communication interface. The communication interfaces of the plurality of modular recording sites are connected serially with respect to each other and to the base and each in-situ analog-to-digital converter is configured for operating in a first operating mode and in a second operating mode. The base is configured for receiving a plurality of digital sensor signals from the plurality of modular record-
              (Continued)

ing sites and to process the plurality of digital sensor signals so as to provide the probe signal.

21 Claims, 50 Drawing Sheets

(51) Int. Cl.
    *A61B 5/291*        (2021.01)
    *A61B 5/31*         (2021.01)
(52) U.S. Cl.
    CPC ............ *A61B 5/685* (2013.01); *A61B 5/6868* (2013.01); *A61B 2562/046* (2013.01)

(56) References Cited

U.S. PATENT DOCUMENTS

| | | |
|---|---|---|
| 7,623,053 B2 | 11/2009 | Terry et al. |
| 2004/0006264 A1 | 1/2004 | Mojarradi et al. |
| 2009/0079606 A1 | 3/2009 | Terry et al. |
| 2013/0278453 A1 | 10/2013 | Steensgaard-Madsen et al. |
| 2018/0242916 A1 | 8/2018 | Purdon et al. |
| 2020/0295772 A1 | 9/2020 | Huang et al. |
| 2020/0359921 A1 | 11/2020 | Ludwigs |

FOREIGN PATENT DOCUMENTS

| | | |
|---|---|---|
| CN | 111936044 A | 11/2020 |
| JP | 2008135943 A | 6/2008 |
| WO | 2013/100991 A1 | 7/2013 |
| WO | 2019/154989 A1 | 8/2019 |
| WO | 2022/167122 A1 | 8/2022 |

OTHER PUBLICATIONS

C. M. Lopez et al., "A 966-Electrode Neural Probe with 384 Configurable Channels in 0.13 μm SOI CMOS", ISSCC Dig. Tech. Papers, pp. 392-393, 2016.
S. Tao et al., "A Power-Efficient Continuous-Time Incremental Sigma-Delta ADC for Neural Recording Systems," in IEEE Transactions on Circuits and Systems I: Regular Papers, vol. 62, No. 6, pp. 1489-1498, Jun. 2015, doi: 10.1109/TCSI.2015.2418892. XP011582932.
S. Park et al., "Modular 128-Channel—Analog Front-End Architecture Using Spectrum Equalization Scheme for 1024-Channel 3-D Neural Recording Microsystems", IEEE JSSC, vol. 53, No. 2, pp. 501-514, Feb. 2018.
D. De Dorigo et al., "Fully Immersible Subcortical Neural Probes With Modular Architecture and a Delta-Sigma ADC Integrated Under Each Electrode for Parallel Readout of 144 Recording Sites," IEEE JSSC, vol. 53, No. 11, pp. 3111-3125, 2018.
Wendler et al., "Delta-Kodierung zur Reduzierung der Datenrate in neuronalen Sonden mit In-Situ Delta-Sigma Analog-Digital-Wandler Front-End", 2021.
G. Buzsaki et al., "Tools for Probing Local Circuits: High-Density Silicon Probes Combined with Optogenetics," Neuron, vol. 86, pp. 92-105, 2015.
K. Seidl et al., "CMOS-Based High-Density Silicon Microprobe Arrays for Electronic Depth Control in Intracortical Neural Recording-Characterization and Application," in Journal of Microelectromechanical Systems, vol. 21, No. 6, pp. 1426-1435, Dec. 2012.
A.S. Herbawi et al., "High-density CMOS neural probe implementing a hierarchical addressing scheme for 1600 recording sites and 32 output channels," Transducers, pp. 20-23, 2017.
V. Viswam et al., "High-density mapping of brain slices using a large multi-functional 15 high-density CMOS microelectrode array system," Transducers, pp. 135-138. 2017, doi: 10.1109/TRANSDUCERS.2017.7994006.
F Heer et al., "CMOS microelectrode array for the monitoring of electrogenic cells, Biosensors and Bioelectronics", vol. 20, pp. 358-366, 2004, ISSN 0956-5663, doi: 10.1016/j.bios.2004.02.006.
J. Scholvin et al., "Close-packed silicon microelectrodes for scalable spatially 30 oversampled neural recording", IEEE Trans. Biomed. Eng., vol. 63, pp. 120-130, 2016.
T.D.Y. Kozai et al., "Photoelectric Artefact from Optogenetics and Imaging on Microelectrodes and Bioelectronics: New Challenges and Opportunities," J. Mater. Chem. B, pp. 4965-4978, 2015.
Y. Zhang et al., "A 16 b Multi-Step Incremental Analog-to-Digital Converter With Single-Opamp Multi-Slope Extended Counting", IEEE JSSC, vol. 52, No. 4, pp. 1066-1076, Apr. 2017.
C. M. Lopez et al., A Neural Probe With Up to 966 Electrodes and Up to 384 Configurable Channels in 0.13 μm SOI CMOS, IEEE Trans. Biomed. Circuits Syst., vol. 11, No. 3, pp. 510-522, Jun. 2017.
B. C. Raducanu et al., Time Multiplexed Active Neural Probe with 1356 Parallel Recording Sites. Sensors (Basel, Switzerland), Oct. 19, 2017;17(10):2388.
S. Kim et al., "Thermal impact of an active 3-D microelectrode array implanted in the brain", IEEE Trans. Neural Syst. Rehabil. Eng., vol. 15, No. 4, pp. 493-501, 2007.
Rikky Muller, "Brain-computer interfaces: Fundamentals to future technologies", 2021 IEEE International Solid-State Circuits Conference (ISSCC) Tutorial.
Tan Zhichao et al., "Incremental Delta-Sigma ADCs: A Tutorial Review", IEEE Transactions on Circuits and Systems I: Regular Papers, IEEE, US, vol. 67, No. 12, doi:10.1109/TCSI.2020.3033458, ISSN 1549-8328, (Dec. 1, 2020), pp. 4161-4173, (Dec. 1, 2020), XP011823617.
Wendler Daniel et al., "A 0.00378mm2 Scalable Neural Recording Front-End for Fully Immersible Neural Probes Based on a Two-Step Incremental Delta-Sigma Converter with Extended Counting and Hardware Reuse", 2021 IEEE International Solid-State Circuits Conference (ISSCC), doi:10.1109/ISSCC42613.2021.9366015, ISBN 978-1-7281-9549-0, (Feb. 13, 2021), pp. 398-400, XP055889095.
Aziz J N Y et al., "256-Channel Neural Recording and Delta Compression Microsystem With 3D Electrodes", IEEE Journal of Solid-State Circuits, IEEE, USA, (Mar. 1, 2009), vol. 44, No. 3, doi:10.1109/JSSC.2008.2010997, ISSN 0018-9200, pp. 995-1005, XP011252594.
Abraham Volkhard, "Communication Pursuant to Article 94(3) EPC for EP Application No. 22813319.5", May 22, 2025, EPO, Germany.
Yixin Wu, "Office Action for CN Application No. 202180095111.3", Jan. 30, 2026; CNIPA, China.

bitcode frequency (Hz)

integrated noise ($\mu$Vrms)

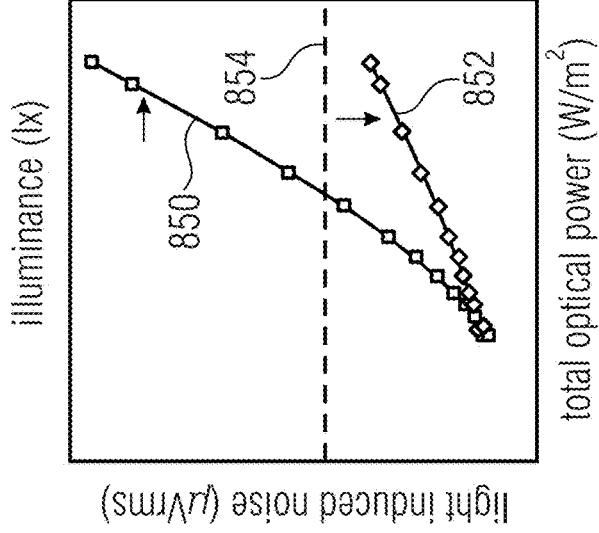
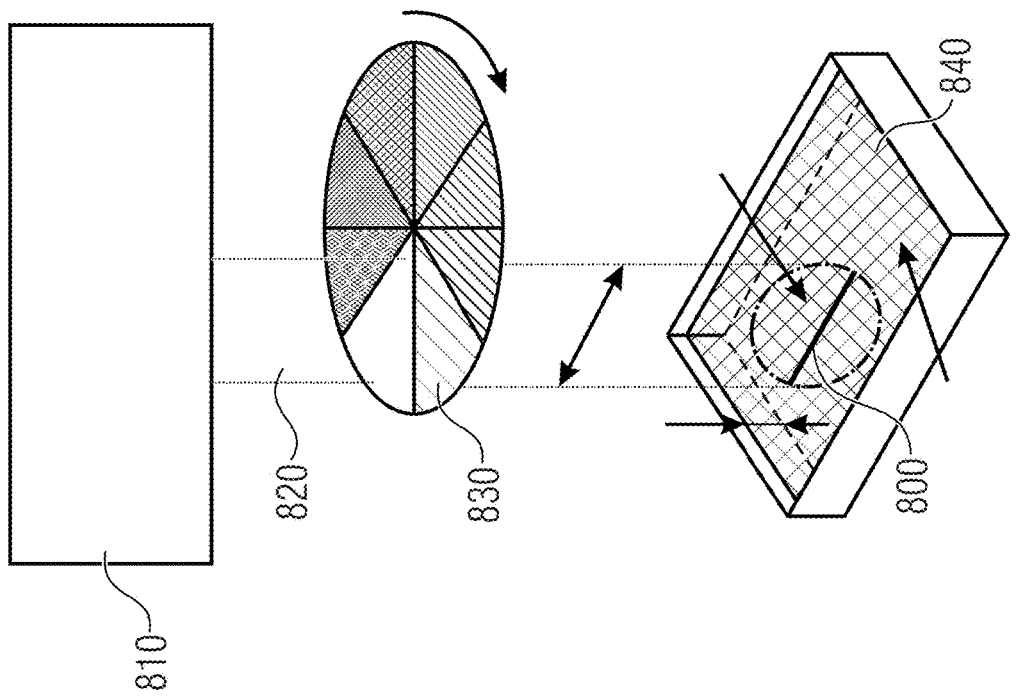
Fig. 8

2260

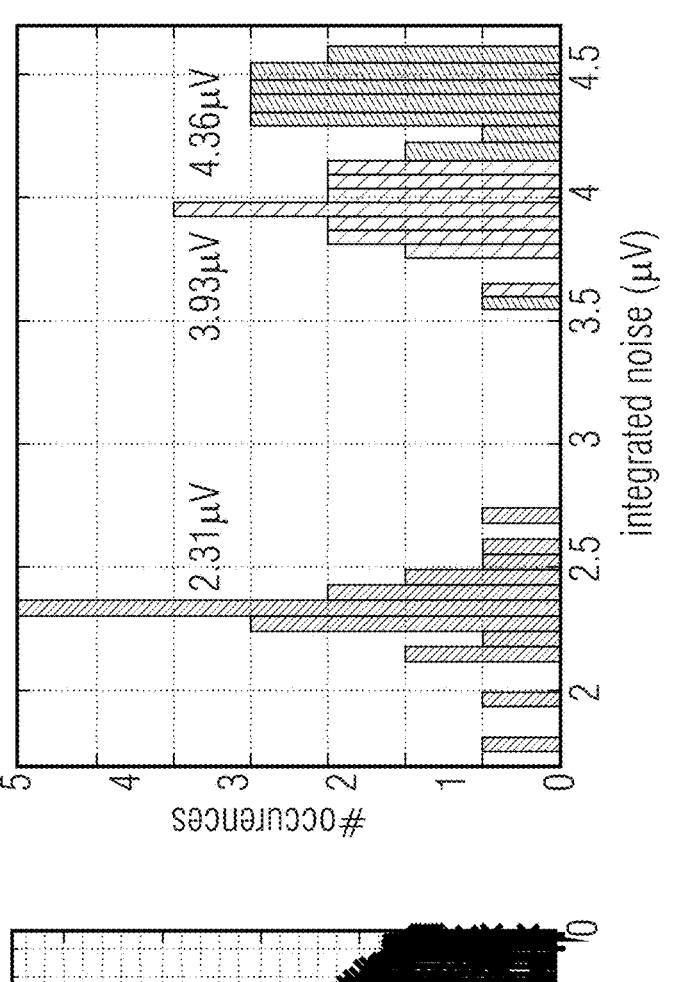
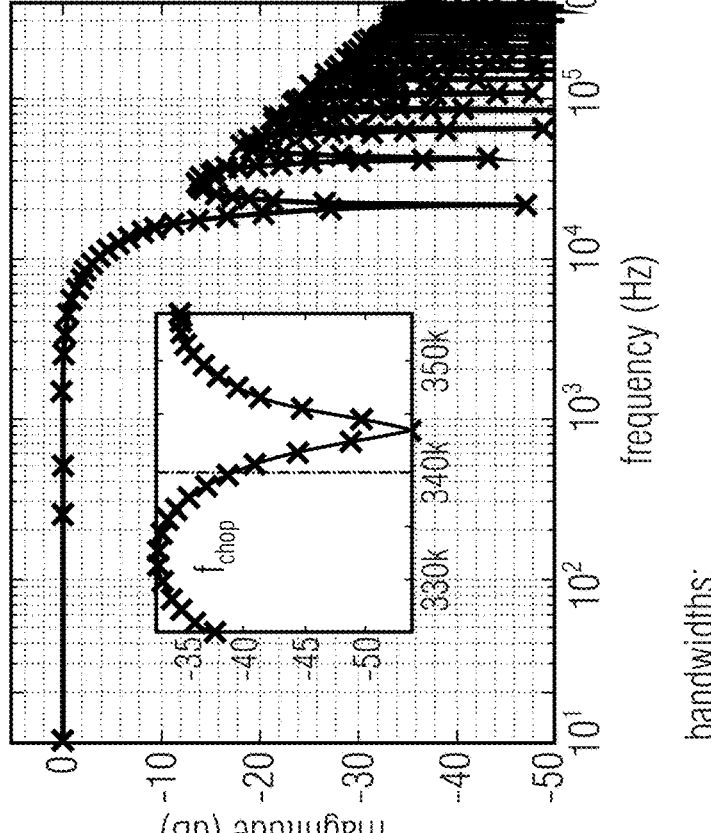
Fig. 21B

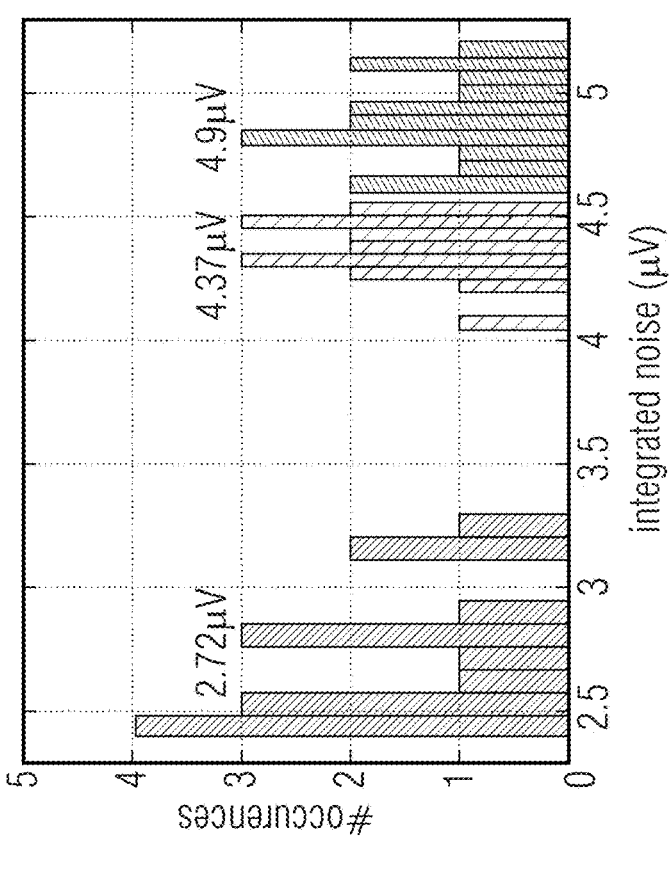
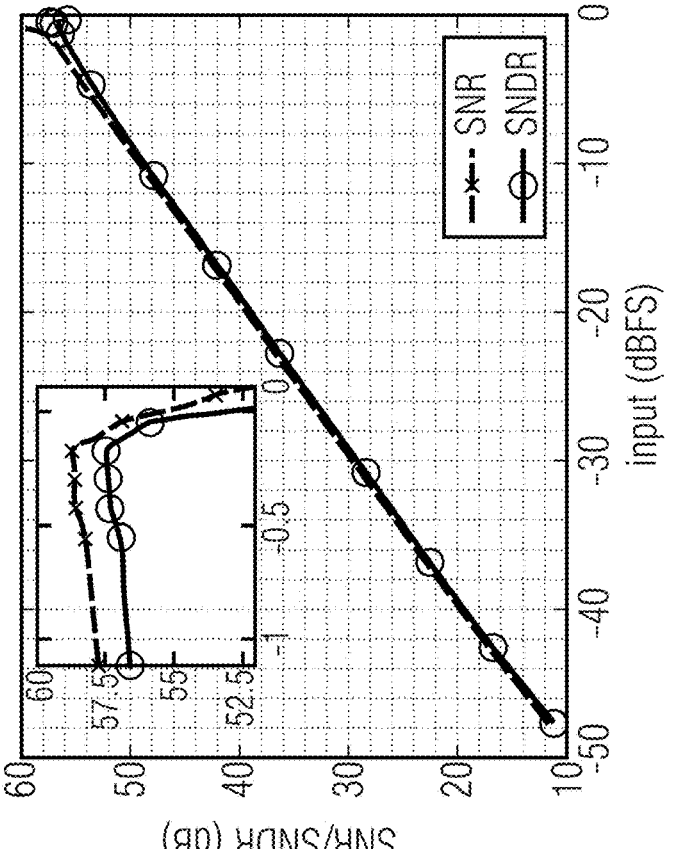
Fig. 21C

| | [1] | [2] | [4] | this work | |
|---|---|---|---|---|---|
| type | ac-coupled ADC in base | ac-coupled ADC in base | ac-coupled ADC in shank | ac-coupled ADC in shank | |
| full scale (mV) | - | - | ±11.25 | ±7 | |
| #electrodes | 1356 | 966 | 144 | 8-24* | |
| #channels | 678 | 384 | | | |
| #wires/required bond pads | 64 | 52 | 9 | 9 | |
| electrode pitch (µm) | 22.5 | 20 | 70 | 55 | 35 |
| ADC resolution (bit) | 10 | 10 | 11 | 11 | 11 |
| ADC dynamic range (bit) | | | 11 | 11 + 4 | 11 |
| ADC architecture | SAR | SAR | OTA-C IΔΣ | OTA-C IΔΣ w, extended counting | |
| noise (µVms) LFP: 0.5Hz - 1kHz | 50.2 | 10.32 | 7.7 | 2.72 | 2.31 |
| noise (µVms) AP: 300Hz - 10kHz | 12.4 | 6.36 | 10.46 | 4.37 | 3.93 |
| power/Ch, (µW) | 45 | 49.06 | 39.14 | 14.94 | 13.94 |
| area/Ch, (mm²) | 0.12 | 0.12 | 0.0049 | 0.00462 | 0.00378 |
| Ch, FoM (fJ/C·s) | 7866.43** | 5717.44** | 13012.89 | 1291.35 | 1068.94 |
| E-A Ch, FoM (fJ/C·s·mm²) | 943.97** | 686.09** | 63.76 | 5.97 | 4.04 |
| THD @1kHz & 10mVpp | n/a | 0.40% | 0.22% | 0.078% | 0.074% |
| Crosstalk @ 1kHz (dB) | -63 | -64.4 | -74.7 | <-80 | <-80 |
| supply voltage (v) | 1.2 | 1.2/1.8 | 1.8 | 1.8 | |
| CMOS technology | 130nm | 130nm | 180nm | 180nm | |

*the number of channels in these prototypes is limited by the CMOS reticle, but in principle expandable to a larger number due to the modularity of the system

**estimated with ENOB=8.16 and $f_s$=20kHz | $f_s$=30kHz

Fig. 23

SENSOR ARRAYS, METHOD FOR OPERATING A SENSOR ARRAY AND A COMPUTER PROGRAM FOR PERFORMING A METHOD FOR OPERATING A SENSOR ARRAY

CROSS-REFERENCES TO RELATED APPLICATIONS

This application is a continuation of copending International Application No. PCT/EP2021/080979, filed Nov. 8, 2021, which is incorporated herein by reference in its entirety, and additionally claims priority from European Application No. EP 21 155 294.8, filed Feb. 4, 2021, which is incorporated herein by reference in its entirety.

BACKGROUND OF THE INVENTION

Embodiments according to the invention relate to sensor arrays such as neuronal probes, a method for operating a sensor array and a computer program for performing a method for operating a sensor array.

In sensor applications, such as in biomedical measurement technology, frequently, a large number (more than 100) of sensor signals in the body have to be contacted and carried to external electronics. This is in particular the case for neuronal sensors where a number of small sensors and electrodes, respectively, which is as large as possible, are attached to a device for detecting neuronal signals in the brain tissue. The signals are carried to the outside to a computer control system which can process and store the signals. Such neuronal sensor systems are applied in neuroscience or generally in fields of application dealing with brain activity research.

Typically, neuronal needles consist of a plurality of electrodes and electric conductive traces carrying the signals to a base at the top-end of the needle. At this end a cable is attached to carry the signals to an external signal processing device. Typically, signal conditioning consists of a chain of preamplifier, filter and analog-digital converter. While in passive needles no active readout electronics is implemented in the needle, the electronics are partly or completely integrated in the base in active needles.

Neuronal signals can be divided into two main types, low frequency signals (local field potentials) with amplitudes of up to several millivolts and high frequency signals (action potentials) with amplitudes up to several hundred millivolts.

Since the amplitudes are very small, the same are also susceptible to interference sources, in particular when the conductor carrying the signal to the outside has a length of several centimeters.

By parasitic effects, such as line capacitances, different signals can interfere with each other on one needle, such that original source/electrode can no longer be identified (crosstalk).

The requirement that the neuronal needles typically have to be introduced into the brain tissue results in another important aspect for the application: tissue damages during surgical introduction into the brain tissue are to be minimized. For that reason, needles need to have a cross-sectional area that is as small as possible. While this has been successfully realized so far for the shank, all neuronal needles published so far have a large base which cannot be embedded into the brain tissue due to its size. Thus, the maximum introduction depth is limited to the length of the needle.

Another procedure to evaluate the neuronal signals is the usage of multi-electrode-arrays (MEA). In such systems brain slices can be placed on a two-dimensional array of neuronal sensors and the neuronal activity of the brain slices can be measured.

Generally, a great number of neuronal probes of different designs that can be used for the described applications exist already. All known systems can be classified based on the degree of electronic integration.

Neuronal evaluation systems can be divided into three groups.

One group comprises passive systems without electronics. Such systems consist of electrodes and electrical conductors, wherein the conductors guide the signals from a sensor to an external interface. There exists a plurality of different implementations, mostly on flexible substrates. An overview can be found in [1]. These systems are restricted to a small number of electrodes.

Another group comprises passive electronic systems. In passive CMOS sensor systems, no active evaluation electronics is implemented, but merely electronically-controlled switching allowing a connection of a specific sensor element (for example an electrode) with one of the conductors that lead to the output contacts. The evaluation electronics is located outside the system. The number of electrodes that can be readout simultaneously is limited by the number of contacts on the base. The papers [2] and [3] describe neuronal needles, whereas paper [4] introduces a two-dimensional MEA-system, which is based on the passive concept.

The third group comprises active electronic systems. In active needles, part of the evaluation electronics is integrated in the chip [5, 6]. Here, the signal chain (for example signal amplifier, analog-to-digital conversion, digital processing/interface) is integrated in the base. Similar to [2] and [3], the shank itself includes electronically-controlled switches and preamplifiers that carry the neuronal signals from selected electrodes to the base. A similar active MEA-System is however described in [7]. Additionally to switches for the selection of a sensor node, a part of the evaluation circuit is integrated in the sensor array (filter and preamplifier). The conversion from analog to digital is outside of the sensible area.

The known solutions show disadvantages. All known solutions have a very large base (electronics outside of the sensible area) and hence cannot, in case of neuronal needles, completely be immersed in the tissue. Additionally, the size of the base requires an invasive surgical procedure. The number of sensor nodes (for example electrodes) that can be readout in parallel depends on the shank width and the available area, respectively, for carrying analog signals from the electrodes to the base electronics. For carrying the signals to the outside, other solutions have many terminals and are hence difficult to handle. In passive needles, the number of terminals is directly proportional to the number of electrodes that can be read out simultaneously.

Known solutions carry sensitive neuronal signals from the sensors to the base. Thus, the same are particularly sensitive against external interference sources, as well as susceptible to crosstalk between the channels. In comparison to passive systems active concepts improve the signal integrity by pre-amplifying the signals on-site (in-situ/under the electrode). All known concepts are not suitable for reading out an arbitrary number of electrodes simultaneously. Furthermore, the conductors in the shank still guide analog signals, which are in fact amplified, but not completely insensitive to disturbances.

As the number of electrodes increases, conventional devices need either a large number of interconnects at the base of the probe or allow only a reduced number of electrodes to be read out simultaneously [8, 3].

In the use of biomedical measuring methods, oftentimes, a multitude of sensors is simultaneously read out so as to monitor bodily functions. In particular, this concerns the field of neuroscience, or the detection of brain activity, wherein sensors are invasively inserted into the brain tissue. These neuronal probes have a shank on which there should be as many electrodes with a pitch of <50 μm as possible so as to be able to reliably detect the activity of individual neurons. These spike-like events of single neurons are called action potentials (APs) and have a frequency range from 300 Hz to 10 kHz. In contrast, signals that consist of or comprise several neurons and are filtered by the brain tissue are called local field potentials (LFP). These typically occur in the frequency range from 0.5 Hz to 1 kHz. Generally, a distinction can be made between passive and active probes. With passive probes, no direct signal conditioning takes place. On the shank, there are only electrodes that are connected to pads in the so-called base and may be connected to external measuring means. In active fully integrated probes, the complete signal conditioning chain is implemented on-chip. The analog neuronal signals are wired along the shank to the base, where a majority of the signal conditioning takes place. Due to the high level of integration of electronics, a large silicon area is needed in the base. Thus, the probes cannot be fully immersed into the brain tissue without damaging the same. WO2019154989 describes a concept in which the full signal conditioning takes place on the shank of a probe and all sensors/channels are read out simultaneously. This enables the base and the shank to be dimensioned with an equal width so that the probe can be fully immersed into the brain tissue without significantly damaging the tissue. This enables the detection of neuronal signals in deep brain regions with a high signal quality and high spatial resolution. Accordingly, this concept requires an analog front-end (AFE) with a smallest possible silicon area that meets the requirements as to the electrode density and that can be integrated into the shank of a probe. At the same time, the noise has to be very low so as to be able to reliably detect the neuronal signals with small magnitudes. To meet the temperature requirements (temperature increase in the tissue of <1° C.), the power consumption of a front-end, or the power density in the shank, has to be very low.

In general, there are numerous analog front-ends for the detection of neuronal signals, wherein some have already been integrated into a neuronal probe. [5] describes an AFE whose signal conditioning chain consists of or comprises a preamplifier, separate filters with amplifiers for APs and LFPs, a multiplexer and a successive approximation register (SAR) analog-to-digital converter (ADC). Except for the preamplifier, which is integrated on the shank of the probe, the remaining components are located in the base of the probe. In [6], in contrast to [5], a multiplexer is implemented after the preamplifier on the shank so that several electrodes share a line to the base. In addition, an integrator with a reset is placed in front of the further signal conditioning in the base, similar to [5], so as to reduce the noise due to the increased bandwidth through multiplexing.

[10] describes an AFE based on two continuous-time incremental delta-sigma (IΔΣ) ADCs connected in a pipeline configuration. In this case, a coarse quantization of the input signal is first performed with the first ADC. The remaining quantization error is used as the input signal for the second ADC, where a fine quantization takes place accordingly. A preamplifier or anti-aliasing filter is not needed for the AFE.

[11] describes a system based on a continuous-time delta-sigma ADC. This includes a low-noise amplifier, followed by a programmable amplifier and the ADC.

[12] describes an AFE that has already been implemented on the shank of a neuronal probe. This was realized through minimizing the signal conditioning chain, with an area-efficient continuous-time first-order IΔΣ ADC representing the front-end.

Except for [12], all of the methods described need significant silicon area at the transistor level, so that they cannot be integrated on the shank of a neuronal probe while meeting the area requirements.

The signal conditioning chains of the methods [5] and [6] comprise too many components to be able to integrate them all on the shank. In contrast, the signal conditioning of the system presented in [10] consists of two ADCs. However, the architecture described is unsuitable due to the silicon area needed. In this case, only the modulator of the IΔΣ ADCs, without a corresponding decimation filter, has been implemented in silicon. The neuronal AFE in [11] has again too large of an area requirement.

The AFE in [12] requires little silicon area and it has already been integrated into the base of a probe. However, the electrode density is too low to be able to reliably detect the activity of individual neurons. In addition, the first-order IΔΣ ADC AFE described leads to increased power density in the shank. For a sufficiently high resolution during use, a high sampling rate is needed, leading to a high power consumption. If it were possible to further reduce the area of the AFE, e.g., using time-multiplexing methods or other circuitry techniques, the power density would increase even further. This would be problematic with respect to the temperature conditions of the brain tissue. In addition, compared to other known solutions, the noise level in the frequency band of the AP is increased. A discrete-time method such as in U.S. Pat. No. 5,410,310 [14] is also unsuitable for the application since the integration capacitor would have to be selected to be very large in order for the system to meet the noise requirements. As a result, implementation on a smallest possible area cannot be ensured, and the requirements as to the electrode density cannot be met.

Therefore, it is desired to get a concept which makes a better compromise between reducing the size of the base, enabling a simultaneous readout of an arbitrary number of sensor nodes and complexity.

The object of the invention is to provide a signal conditioning system for recording brain activity in deep brain regions with a high spatial resolution. The invention includes the system design of an AFE with a dedicated architecture, and the implementation at the transistor-level, which can be integrated on the shank of a neuronal probe with the smallest possible silicon area, lowest possible power consumption, and lowest possible noise while having sufficiently high linearity. The system can be used not only for 1D electrode arrays, but is also suitable for 2D and 3D multi-electrode arrays.

The range of application is not limited to the readout of brain activity, but is also suitable for the operation of other sensor systems in which a high-resolution ADC is required, such as biosensors, microelectromechanical systems, or image sensors.

SUMMARY

An embodiment may have a sensor array comprising: a base for providing a probe signal; a plurality of modular recording sites, wherein each modular recording site of the plurality of modular recording sites comprises, a CMOS substrate, at least one sensor element configured for receiving an analog signal, an in-situ analog-to-digital converter configured for converting the analog signal into a digital sensor signal and a communication interface configured to provide the digital sensor signal to the base; wherein the communication interfaces of the plurality of modular recording sites are connected serially with respect to each other and to the base; wherein each in-situ analog-to-digital converter is configured for operating in a first operating mode for performing a first quantization of the analog signal using a first quantization setting and to acquire a residual error from the first quantization;

and for operating in a second operating mode for performing a second quantization of the residual error using a second, different quantization setting for a same element of the analog-to-digital converter.

Another embodiment may have an analog-to-digital converter comprising a continuous-time delta-sigma modulator configured for operating in a first operating mode for performing a first quantization of an analog signal using a first quantization setting and to acquire a residual error from the first quantization; and for operating in a second operating mode for performing a second quantization of the residual error using a second, different quantization setting of the analog-to-digital converter.

Another embodiment may have a neuronal probe comprising an analog-to-digital converter according to the invention and an offset compensation circuit, the compensation circuit configured for compensating an offset in the analog signal.

Another embodiment may have a method for operating a sensor array according to the invention, comprising: recording of a signal with a sensor of a modular recording site of a plurality of modular recording sites of the sensor array; converting of the signal into a plurality of digital sensor signals using the plurality of modular recording sites of the sensor array by operating each analog-to-digital converter in the first operating mode and in the second operating mode to acquire the respective digital sensor signal; providing of the plurality of digital sensor signals to the base of the sensor array using the communication interfaces of the plurality of modular recording sites of the sensor array; receiving of the plurality of digital sensor signals from the plurality of modular recording sites of the sensor array with the base of the sensor array; processing of the plurality of digital sensor signals by the base of the sensor array so as to acquire a probe signal; and providing the probe signal with the base of the sensor array for a remote device.

In accordance with a first aspect of the present invention, the inventors of the present application realized that one problem encountered when trying to achieve high signal quality and high spatial resolution at a detection of neuronal signals stems from the fact that a high electrode density is required, and that at the same time the components integrated in a shank of a neuronal probe have to satisfy the requirement of a small area consumption and a very low power density in the shank. According to the first aspect of the present application, this difficulty is overcome by using a two-step in-situ analog-to-digital converter, which is configured for operating in two modes with different quantization settings. The inventors found, that compared to a conventional first-order system, the oversampling ratio can be reduced by using a multi-step method with coarse and fine quantization. At the same time, the area can be maintained since it is sufficient for the system to use one integrator at both modes. This is based on the idea that in sum a low quantization error is obtained with a low number of elements which in turn allows for small elements and low chip sizes, which is of particular advantage in the field of biometric probes.

Accordingly, in accordance with a first aspect of the present invention, a sensor array comprises a base for providing a probe signal and a plurality of modular recording sites. Each modular recording site of the plurality of modular recording sites comprises, a CMOS substrate, at least one sensor element configured for receiving/detecting an analog signal, an in-situ analog-to-digital converter configured for converting the analog signal into a digital sensor signal and a communication interface configured to provide the digital sensor signal to the base. The communication interfaces of the plurality of modular recording sites are connected serially with respect to each other and to the base. For example, the base is configured for receiving a plurality of digital sensor signals from the plurality of modular recording sites and to process the plurality of digital sensor signals so as to provide the probe signal. Each in-situ analog-to-digital converter is configured for operating in a first operating mode for performing a first quantization of the signal using a first quantization setting and to obtain a residual error from the first quantization; and for operating in a second operating mode for performing a second quantization of the residual error using a second, different quantization setting for a same element of the analog-to-digital converter.

The serial connection realized by the communication interface means that all modular recording sites of the plurality of modular recording sites can be read out simultaneously. In this case the communication interface is, for example, in a normal operating mode. Each communication interface of each modular recording site, for example, transfers the respective digital sensor signal in a sequence of a plurality of digital sensor signals (e.g., the sequence comprises from each modular recording site a digital sensor signal), wherein a position of the respective digital sensor signal in the sequence corresponds to a position of the respective modular recording site with respect to a position of each other modular recording site. In that way, the digital sensor signals of each modular recording site can be linked to the digital sensor signals of the neighboring modular recording sites and can be carried to the base. In that way, for example, the number of connections from one modular recording site of the plurality of modular recording sites to a neighboring modular recording site of the plurality of modular recording sites is kept very small and no analog signal (for example the received biosignal by each modular recording site) susceptible to interferences is carried to the base. Since all signals are digitized (this means, for example, that each biosignal received by a modular recording site of the plurality of modular recording sites is converted into a digital sensor signal) directly on-site (for example on each modular recording site), and send serially by a communication interface to the base, the sensor array requires only a very small number of lines to the base. Thus, the sensor array not only reduces the complexity but also the size of the base and shank of the sensor array, because only a reduced number of lines from each modular recording site of the plurality of modular recording sites is needed to transfer a digital sensor signal to the base. The serial connection of the communication interfaces of the plurality of modular recording sites with respect to each other and to the base also enables the sensor array to contact an arbitrary number of modular recording sites.

According to an embodiment, each in-situ analog-to-digital converter comprises a signal input and is configured for providing a connection between the signal input and the signal in the first operating mode and for disconnecting the signal input from the signal in the second operating mode. The in-situ analog-to-digital converter might comprise a switch configured to toggle between connecting and disconnecting the signal input and the signal. This is based on the idea that the signal can be quantized with a coarse quantization in the first operating mode and that by disconnecting the signal at the second operating mode a quantization error remaining from the quantization of the signal in the first operating mode can be quantized with a fine quantization. This increases the signal quality.

According to an embodiment, the first operating mode and the second operating mode differ from each other in view of an amplification applied in a feedback loop of a delta-sigma modulator of the analog-to-digital converter; a sampling rate of the delta-sigma modulator; and/or of a signal shape applied for sampling in the delta-sigma-modulator. For example, for the second operating mode, the amplification factor may be reduced, the sampling rate may be increased and/or a different signal shape may be used for the fine quantization. It allows, thus, a reuse of an integrating stage or integrator and/or of a quantizer and/or a feedback digital-to-analog converter of the delta-sigma modulator for different granularity, such that in sum a low quantization error is obtained with a low number of elements which in turn allows for small elements and low chip sizes, which is of particular advantage in the field of biometric probes.

According to an embodiment, in the second operating mode an integrator and/or a quantizer and/or a feedback DAC of a delta-sigma modulator of an analog-to-digital-converter, i.e. the in-situ analog-to-digital converter, is reused with respect to the first operating mode. This is based on the idea that different quantization levels can be achieved even if some elements of the in-situ analog-to-digital converter are reused. This has especially the advantage of a reduction of the oversampling rate and thus power consumption, and reduction of the needed area on the probe shank for the analog-to-digital conversion of the analog signal detected by the at least one sensor element of the respective modular recording site. Thus, each modular recording site can be realized very small which results in a thin sensor array preventing or reducing a damage of material into which the sensor array is inserted.

According to an embodiment, a delta-sigma modulator of a digital-to-analog converter is implemented in absence of an input-feedforward path. In other words, the in-situ analog-to-digital converter of a modular recording site can comprise a delta-sigma modulator without an input-feedforward path. An architecture with no input-feedforward is used to minimize the signal paths and therefore reduce the size of the sensor array.

A finding of the present invention is that by converting an analog signal to be measured, in particular a biosignal such as biomedical signals, e.g., biochemical signals and more specific a neuronal signal as being obtainable from neurons, muscles, brains or other parts of the body such as ears and/or eyes, into a digital sensor signal locally, i.e., at the place of the electrode, a digital sensor signal may be obtained. For example, in each modular recording site of the plurality of modular recording sites the respective in-situ analog-to-digital converter might be implemented under the respective at least one sensor element realizing a tight packaging. It is more efficient and reduces the complexity when the biosignal received by a modular recording site of the plurality of modular recording sites is converted directly in the modular recording site into a digital sensor signal. Thus, the digital sensor signal can be provided to the base instead of the analog sensor signal. The signal conditioning chain (as stated in the art) of the readout electronics is reduced by omitting preamplification, amplification and filtering and is replaced by direct local analog-to-digital conversion of the biosignals (for example sensor signals). Since only digital sensor signals (respectively, digital data) and no sensitive signals (for example analog signals) are carried from each modular recording site of the plurality of modular recording sites to the base (for example along a shank), (nearly) no crosstalk can be measured between each modular recording site (for example sensors) and there is high robustness with respect to external interference sources, such as light sources or electromagnetic fields. Thus, the digital sensor signal is robust against distortions and/or may be combined with a plurality of further signals allowing for small communication interfaces. Further, a small base is obtained despite the possible high number of recording sites carrying sensor elements for the measurement.

The analog signals are directly converted by each modular recording site into a digital sensor signal, thus, the signal conditioning is already done by each modular recording site. Thus, the base can be implemented with a small size, because few components for processing a signal are needed. With this embodiment, not only the size of the base can be reduced, but also the complexity of the sensor array can be low and an arbitrary number of modular recording sites can be contacted and read out at the same time.

Each modular recording site of the plurality of modular recording sites receives, for example, a biosignal. The biosignal is an analog signal so that the conversion from the biosignal to a digital sensor signal is performed by an analog-to-digital conversion. This is, for example, realized by an analog-to-digital converter, e.g. the in-situ analog-to-digital converter, implemented in each modular recording site. The base receives from each modular recording site of the plurality of modular recording sites digital sensor signals. Thereby, it is, for example, not necessary that the base comprises an analog-to-digital converter like active sensor arrays stated in the art. Thus, the base is, for example, implemented with a small size, because the base needs few components like, for example, conductors respectively, for all recording sites and/or ADCs (analog-to-digital converter), and/or filter and/or amplifier compared to the base of a sensor array stated in the art. The direct conversion of the biosignal into a digital sensor signal by each modular recording site of the plurality of modular recording sites makes it possible to contact an arbitrary number of modular recording sites of the plurality of modular recording sites.

In an embodiment, each modular recording site of the plurality of modular recording sites comprises a communication interface. The communication interface can, for example, receive configuration data from the base. Based on the received configuration data, the modular recording site can, for example, adapt parameters relating to the operation of the modular recording site. The configuration data can, for example, hold information about the state of each modular recording site, for example an on-state or an off-state of the modular recording site. Thus, it can be chosen which modular recording site should record and therefore receive a signal. Information which, for example, can be received in the form of configuration data may include a change of the scaling of the conversion from analog to digital, e.g. the quantization settings for the two different operating modes of the in-situ analog-to-digital converter. The communication interface is an interface enabling communication between each modular recording site and the base. In this case the communication interface, for example, operates in a configuration mode.

In an embodiment, the communication interface comprises a serial interface. The communication interfaces of the plurality of modular recording sites are, for example, connected to each other in a serial communication chain comprising a forward path from the base to a sensor array endpoint of the sensor array and a backward path from the sensor array endpoint to the base. Wherein the sensor array endpoint is a biomedical sensor array endpoint, in particular a tip.

For each pair comprising a first modular recording site and a directly adjacent neighboring second modular recording site, the communication interface of the first modular recording site is connected to the forward path and the communication interface of the second modular recording site is connected to the backward path. The digital sensor signals from each modular recording site as well as a clock are, for example, forwarded from one modular recording site to a next modular recording site (for example, to a directly adjacent neighboring modular recording site). The clock is, for example, slightly delayed from one modular recording site to another modular recording site to spread digital supply noise and reduce peak current consumption.

The modular recording sites are, for example, grouped into blocks of two modular recording sites comprising a first modular recording site connected to the forward chain and forward clock and a second modular recording site connected to the backward chain and backward clock. Thus, for example, the serial interfaces of every second modular recording site are connected/coupled to a forward chain and the serial interfaces of all other modular recording sites are connected/coupled to a backward chain. The first chain and the second chain are coupled to the base such that the digital sensor signal is transferred to the base. Alternatively, instead of using pairs of modular recording sites for the forward and backward chain also multiples of two (for example, 4 modular recording sites, the first two connected to the forward chain and the second two connected to the backward chain, or 6 modular recording sites, the first three connected to the forward chain and the second three connected to the backward chain) may be used or even only single modules with only one chain in one direction. In the latter case of only one chain, an additional digital wire from the end of the chain to the base may serve as backward path, when all modular recording sites are connected to the forward chain or an additional digital wire from the base to the end of the chain has to serve as forward path, when all modular recording sites are connected to the backward chain. An implementation using pairs of modular recording sites on the forward path and the backward path is more efficient compared to a single module solution, where only one path either the forward path or the backward path is used but not mandatory. Thus, each digital sensor signal provided by each modular recording site can be transferred very fast to the base and according to an embodiment only digital signals are exchanged between each modular recording site and the base. It is possible to read out the plurality of modular recording sites simultaneously and each digital sensor signal transferred to the base can be assigned to a specific modular recording site, because of the implementation of a forward chain and a backward chain connecting each modular recording site with each modular recording site and the base.

In an embodiment, the base is configured to receive a combined sensor signal from the plurality of modular recording sites, the combined sensor signal comprising the digital sensor signals of each of the modular recording sites. The combined sensor signal is, for example, a sequence of each digital sensor signal of each modular recording site (e.g., the sequence of the plurality of sensor signals), or a superposition of each digital sensor signal of each modular recording site with each digital sensor signal of each modular recording site. This implementation can, for example, reduce the complexity of the sensor array and reduce the size of the base, because there is only one digital data bus needed which connects each modular recording site of the plurality of modular recording sites with the base and transfers a combined digital sensor signal to the base.

In an embodiment, each modular recording site of the plurality of modular recording sites comprises a continuous-time multi-step incremental delta-sigma analog-to-digital converter, e.g., as the in-situ analog-to-digital converter. Since even the largest biosignals, in particular neuronal signals are only in the range of few millivolts and the required linearity is low, a direct conversion (for example by each modular recording site) using a Gm-C (integrator using a transconductance Gm of an amplifier in combination with a capacitance C) based incremental delta-sigma analog-to-digital converter in each modular recording site can be implemented. The continuous-time multi-step incremental ADC exploits hardware sharing and an extended counting technique and allows the implementation on a minimal silicon area, since the integrator and comparator of a first-order modulator can be reused in multiple quantization steps. The usage of a continuous-time multi-step incremental delta-sigma analog-to-digital converter by each modular recording site of the plurality of modular recording sites has the advantage that the received signal by each modular recording site can be converted into a digital sensor signal directly at each modular recording site. Thus, from each modular recording site to the base (nearly) insensitive digital sensor signals to electromagnetic interferences or crosstalk are sent. Thereby, the sensor array gets very accurate. Another advantage of this embodiment is that the signals transferred from each modular recording site of the plurality of modular recording sites to the base are already digitized instead of sensor arrays as in prior art, where the conversion of the signals to a digital sensor signal is implemented in the base, which makes the base very big, but with the sensor array according to this invention the size of the base can be small. Continuous-time delta-sigma converters are known for their intrinsic low-pass transfer characteristics. Thus, more current and additional area can be saved, because the necessity for a dedicated anti-aliasing filter as an additional circuit block can be omitted. Thus, the complexity of the sensor array is low.

In an embodiment, each modular recording site of the plurality of modular recording sites comprises an integrator, a quantizer and at least two feedback paths with different gain coefficients configured to convert directly the signal into a digital sensor signal. The integrator is, for example, an OTA-C integrator (respectively, operational transconductance amplifier plus capacitance), i. e. a two-step incremental delta-sigma ADC. But it is also feasible to implement even ADCs with more quantization steps (more quantization steps means more feedback paths with different gain coefficients), which may be more optimal for different designs of the sensor array. The output of the single branch OTA-C integrator is connected to the quantizer, i.e., comparator and output latch, driving the switches for a current and/or voltage feedback. The integrator of each modular recording site of the plurality of modular recording sites is configured to receive the signal and to integrate the signal, so as to obtain an integrated signal. The quantizer of each modular recording site of the plurality of modular recording sites comprises a latched comparator and an output latch. The latched comparator is configured to receive the integrated signal and to quantize the integrated signal. The output latch is configured to drive feedback switches for a current and/or voltage feedback to the integrator, based on the comparator output and the quantization step. The noise of the feedback current and the feedback switches, which operate at digital level input signals, is negligible compared to the major noise contributors. An implementation with a Gm-C integrator has, for example, additionally the advantage that the area in demand is very small. Another advantage of the usage of an integrator and a quantizer directly by each modular recording site is that no preamplifier is needed. With the integrator and the quantizer the signal can directly be converted into the digital sensor signal by each modular recording site. Thus, digital sensor signals are transferred from each modular recording site of the plurality of modular recording sites to the base. In sensor arrays, as in prior art, the biosignal is transferred as an analog signal to the base and therefore a preamplifier is needed.

In an embodiment, each modular recording site of the plurality of modular recording sites is configured for converting the signal into the digital sensor signal independently of neighboring modular recording sites. This has the advantage that the signal received by each modular recording site of the plurality of modular recording sites does not have to be transferred as an analog signal, for example to the next modular recording site or directly to the base, but instead is converted directly by each modular recording site into a digital sensor signal. Thus, the sensor array is nearly insensitive to electromagnetic interferences or crosstalk.

In an embodiment, one modular recording site of the plurality of modular recording sites comprises at least one sensor element configured for detecting the signal. The sensor element may be an electrode, an optical sensor and/or a chemical sensor. It is also, for example, possible to have one modular recording site with, for example, three sensor elements. This means, for example, that more than one sensor element shares an electronic circuitry in one modular recording site of the plurality of modular recording sites for converting the analog signal into a digital sensor signal. Thus, the number of components is reduced and therefore, also the size of the sensor array is reduced.

In an embodiment, the plurality of modular recording sites is arranged along an axial direction and forms an array along the axial direction. An extension of the base along a first perpendicular direction perpendicular to the axial direction is at most an extension of the plurality of modular recording sites along the first perpendicular direction. An extension of the base along a second perpendicular direction perpendicular to the axial direction is at most an extension of the plurality of modular recording sites along the second perpendicular direction. This means, for example, that the cross-section perpendicular to an axis from the base through all modular recording sites (through the plurality of modular recording sites) to the last modular recording site does not have to change. This has the advantage that one can choose an arbitrary number of modular recording sites for the plurality of modular recording sites of the sensor array without influencing the cross-section of the base. Thus, the base can, for example, have the same cross-section as each of the modular recording sites of the plurality of modular recording sites. Thus, it is possible to bury the base completely in the tissue. Thus, the sensor array can be placed deeper into the tissue and the invasive surgical procedure may be minimized. This embodiment does not mean that the size of the base does not change with the number of modular recording sites. The size of the base, for example, is able to change (slightly) in one dimension.

In an embodiment, a cross-section of the plurality of modular recording sites in a plane perpendicular to an axial extension of the sensor array is independent of the number of modular recording sites. This can mean that the cross-section of each modular recording site does not change when more and more modular recording sites are appended to the sensor array but it can be possible to change the cross-section of each modular recording site of the plurality of modular recording sites if it is necessary for the surgical procedure to have a sensor array which has, for example, a decreasing cross-section from the base over the plurality of modular recording sites to the last modular recording site. Although embodiments allow for a small base even at high numbers of modular recording sites, the size of the base may change with the number of modular recording sites. The size of the base can, for example, change (slightly) in one dimension, when increasing the number of modular recording sites.

In an embodiment, the sensor array comprises one or more columns comprising the plurality of modular recording sites. The modular concept allows the realization of any arrangement of the plurality of modular recording sites, such as in the form a two-dimensional array or a needle having one or multiple columns. The advantage of the modular concept of a plurality of modular recording sites is that the arrangement of each modular recording site of the plurality of modular recording sites with respect to each modular recording site is very flexible. Thus, for example, a sensor array with two columns can be realized. Therefore, the sensor array can record signals from a greater area. Since no global analog signal routing is present and due to high modularity of the design, a longer probe or any application-specific modification of the probe geometry would deliver identical performance.

In an embodiment, the base comprises a wired output interface for providing the probe signal. A number of channels of the wired output interface are independent of the number of modular recording sites and independent of the cross-section of the plurality of modular recording sites in a plane perpendicular to an axial extension of the sensor array. With this implementation, the complexity of the sensor array can be reduced. The reason for the reduction of the complexity of the sensor array is, for example, that one can create a sensor array with an arbitrary number of modular recording sites but with the same wired output interface at the base to an external device.

In an embodiment, the plurality of modular recording sites is arranged between the base and a sensor array endpoint of the sensor array, wherein the sensor array forms a needle. Wherein the sensor array endpoint is a biomedical sensor array endpoint, in particular a tip. Thus, the surgical procedure to get the sensor array into tissue gets easier. With the implementation of a tip it is easier to bury the sensor array in the tissue.

In an embodiment, a modular recording site of the plurality of modular recording sites comprises a housing, the housing comprising a sensor portion for receiving the signal and comprising an insulating portion for insulating the sensor portion from a sensor portion of the housing of an adjacent modular recording site. The housing may be biocompatible and therefore, the sensor array can be buried in the tissue without complications. With an insulating portion between two modular recoding sites it is possible to separate a received signal from one modular recording site from a received signal from another modular recording site. With an insulating portion it may be prevented that a received signal by one modular recording site jumps from one modular recording site to the others and thereby, one would not be able to localize the received signal with the sensor array. With an insulating portion one can, for example, localize the received signal by one modular recording site by the sensor array.

According to an embodiment, a modular recording site of the plurality of modular recording sites comprises a housing, the housing comprising two or more sensor portions for receiving the signal and comprising an insulating portion for insulating each sensor portion from another sensor portion of the two or more sensor portions. Each sensor portion of the two or more sensor portions can receive the signal, wherein each sensor portion, for example, generates an individual signal. The individual signals can be the same or at least partially differ from each other. Thus, for example, if the modular recording site comprises three sensor portions all three individual signals (e.g. generated by the three sensor portions, wherein the sensor portions can also be called electrodes or sensor elements, from the received signal) are the same, all differ from each other or two are the same and one differs from the other two. Thus, one signal received by more than one sensor portion, can result in more than one individual signal, for example, depending on the position of the sensor portions. If a first sensor portion is, for example, arranged nearer to a source of the signal, than a second sensor portion, the first sensor portion generates according to an embodiment a first individual signal with a higher amplitude, than a second individual signal generated by the second sensor portion. By insulating the at least two sensor portions from each other, it may be prevented that the two or more sensor portions interact with each other and generate inaccurate individual sensors. Thus, a very exact localization and analysis of the received signal can be achieved.

In an embodiment, each modular recording site of the plurality of modular recording sites is divided into an analog part and a digital part. The analog part and the digital part comprise a separate supply routing. The digital part is shielded from the analog part by a first conductive element. This means, for example, that the analog part is separated from the digital part by a shield (low-impedance ground shield), configured to block (increase the robustness against) electromagnetic interferences. A second conductive element is arranged encircling a connector of the sensor element so as to shield the analog part and the digital part from the sensor element. In other words, the second conductive element is, for example, a shield that also covers the analog part and the digital part in the direction of the sensor. The analog part is configured to convert the biosignal received by the sensor element into the digital sensor signal. The analog part and the digital part are coupled for providing the digital sensor signal to the digital part. The digital part is configured to provide the digital sensor signal to the base. The whole sensor array is, for example, separated along one dimension (from the base to the last modular recording site) into a digital and an analog part with separate supply rooting and low-impedance ground shield in between, that also covers the top (respectively, a plane covering the analog part and the digital part in the direction of the sensor) to increase the robustness against electromagnetic interferences and to reduce digital noise coupling.

According to an embodiment, the sensor array comprises in each modular recording site an offset compensation circuit configured for compensating an offset (e.g., an electrochemical potential difference between sensor elements, like electrodes) in the analog signal (e.g. a biosignal), e.g. using an additional current-steering digital-to-analog-converter in the Gm-C integrator or a level-shifter at the input of the in-situ analog-to-digital converter increasing its dynamic range.

According to an embodiment, the sensor array comprises in each modular recording site an offset compensation circuit configured for compensating an offset (e.g. mismatch in the current branches when the input is disconnected during fine conversion) in the integrator output-referred current of the in-situ analog-to-digital converter, e.g. using 'chopper' method applied to input transistors and load transistors of the in-situ analog-to-digital converter. The offset can, especially in the second and subsequent operating mode, limit the resolution of the fine quantization. Thus, by compensating the offset a high resolution can be achieved.

An embodiment relates to an analog-to-digital converter comprising a continuous-time delta-sigma modulator configured for operating in multiple operating modes for performing quantization of an analog signal, e.g. in two modes where in a first operating mode for performing a first quantization of an analog signal using a first quantization setting and to obtain a residual error from the first quantization; and for operating in a second operating mode for performing a second quantization of the residual error using a second, different quantization setting of the analog-to-digital converter. E.g. in four modes where in a first operating mode for performing a first quantization of an analog signal using a first quantization setting and to obtain a first residual error from the first quantization; and for operating in a second operating mode for performing a second quantization of the first residual error using a second, different quantization setting of the analog-to-digital converter and to obtain a second residual error from the second quantization; and for operating in a third operating mode for performing a third quantization of the second residual error using a third, different quantization setting of the analog-to-digital converter and to obtain a third residual error from the third quantization; and for operating in a fourth operating mode for performing a fourth quantization of the third residual error using a fourth, different quantization setting of the analog-to-digital converter. In other words, in an n-th operating mode (for $2 \leq n \leq m$, wherein m is the maximal number of operating modes of the analog-to-digital converter) a residual error obtained by a preceding operating mode, i.e. the (n−1)-th residual error obtained in the (n−1)-th operating mode, is quantized to obtain an n-th residual error.

Another embodiment relates to a neuronal probe comprising the analog-to-digital converter described above, e.g., at a modular recording site of the neuronal probe; and/or at a base of the neuronal probe.

According to an embodiment, the neuronal probe further comprises an offset compensation circuit, e.g., at a modular recording site of the neuronal probe; and/or at a base of the neuronal probe. The compensation circuit is configured for compensating an offset (e.g., an electrochemical potential difference between sensor elements, like electrodes) in the analog signal (e.g. a biosignal), e.g. using an additional current-steering digital-to-analog-converter in the Gm-C integrator or a level-shifter at the input of the in-situ analog-to-digital converter increasing its dynamic range.

According to an embodiment, the neuronal probe further comprises an offset compensation circuit, e.g., at a modular recording site of the neuronal probe; and/or at a base of the neuronal probe. The compensation circuit is configured for compensating an offset (e.g. mismatch in the current branches when the input is disconnected during fine conversion (ideally zero differential input)) in the integrator output-referred current of the in-situ analog-to-digital converter, e.g. using 'chopper' method applied to input transistors and load transistors of the in-situ analog-to-digital converter. The offset can, especially in the second and subsequent operating mode, limit the resolution of the fine quantization. Thus, by compensating the offset a high resolution can be achieved.

The neuronal probe is based on the same considerations as the above-described sensor array. The neuronal probe can, by the way, be completed with all features and functionalities, which are also described with regard to the above-described sensor array.

According to an embodiment a method for operating a sensor array comprises the following steps, recording a signal with a sensor of a modular recording site of a plurality of modular recording sites of the sensor array, converting the signal into a plurality of digital sensor signals using the plurality of modular recording sites of the sensor array by operating each analog-to-digital converter in the first operating mode and in the second operating mode to obtain the respective digital sensor signal, providing the plurality of digital sensor signals to the base of the sensor array using the communication interfaces of the plurality of modular recording sites of the sensor array, receiving the plurality of digital sensor signals from the plurality of modular recording sites of the sensor array with the base of the sensor array, processing of the plurality of digital sensor signals by the base of the sensor array so as to obtain a probe signal and providing the probe signal by the base of the sensor array for a remote device.

The method is based on the same considerations as the above-described sensor arrays or neuronal probes.

The method can, by the way, be completed with all features and functionalities, which are also described with regard to the sensor arrays or neuronal probes.

According to an embodiment a computer program comprising a program code for performing, when running on a computer, a method as described above, is created.

BRIEF DESCRIPTION OF THE DRAWINGS

Embodiments of the present invention will be detailed subsequently referring to the appended drawings, in which:

FIG. 2a shows a schematic block diagram of a neuronal probe with a tip according to an embodiment of the present invention;

FIG. 2b shows a schematic perspective view of the neuronal probe shown in FIG. 2a;

FIG. 3a shows a schematic block diagram of a neuronal probe with shield according to an embodiment of the present invention;

FIG. 3b shows a schematic perspective view of the neuronal probe shown in FIG. 3a;

FIG. 8 shows photometric and radiometric light sensitivity measurements for optogenetic applications with a neuronal probe according to an embodiment of the present invention;

FIGS. 20a-1 and 20a-2 shows a transistor-level implementation of a two-step in-situ analog-to-digital converter;

FIGS. 21a-c show measurement data measured with a herein described sensor array;

FIG. 23 shows a table comparing state of the art neural probes with the herein proposed sensor array;

FIGS. 26-1 and 26-2 shows an embodiment of a measurement system with a sensor array comprising a two-step in-situ analog-to-digital converter and associated measurement data;

FIGS. 28-1 and 28-2 show options for differences obtainable by the data compression unit;

FIG. 33$b$ shows 7-bit delta encoding integrated into a decimation filter;

DETAILED DESCRIPTION OF THE INVENTION

Figure 1:
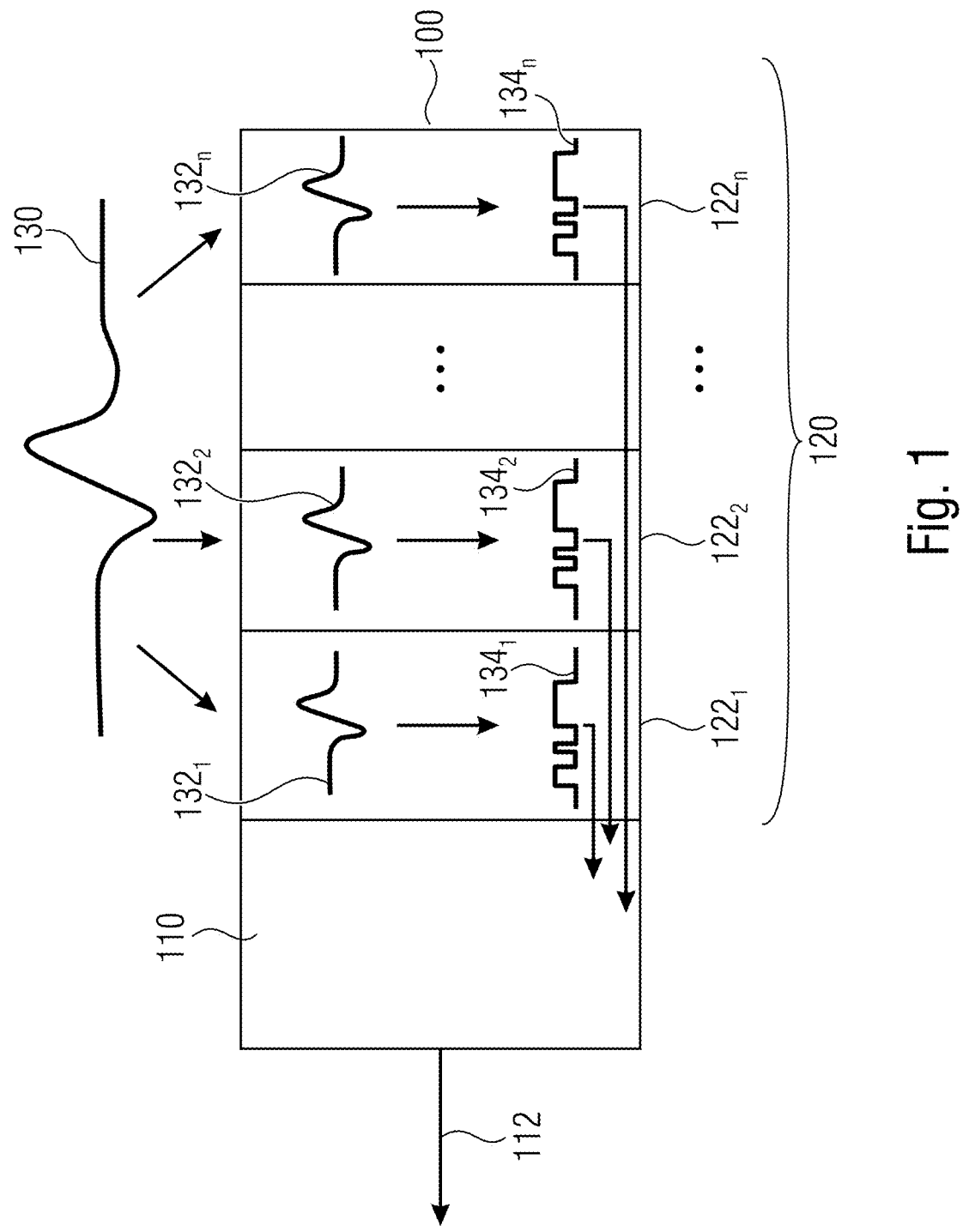
FIG. 1 shows a schematic view of a neuronal probe according to an embodiment of the present invention.

Equal or equivalent elements or elements with equal or equivalent functionality are denoted in the following description by equal or equivalent reference numerals even if occurring in different figures.

In the following description, a plurality of details is set forth to provide a more thorough explanation of embodiments of the present invention. However, it will be apparent to those skilled in the art that embodiments of the present invention may be practiced without these specific details. In other instances, well known structures and devices are shown in block diagram form rather than in detail in order to avoid obscuring embodiments of the present invention. In addition, features of the different embodiments described hereinafter may be combined with each other, unless specifically noted otherwise.

In the following, reference is made to embodiments of the present invention. Embodiments will be described in connection with neuronal probes as one possibility of implementing the present invention. Without any limitation, the description given hereinafter also relates to other sensor arrays, in particular biomedical sensor arrays. Examples for such biomedical sensor arrays are optical sensor arrays which may be used in connection with a retina of a human or animal. E.g., such a sensor array may be configured for receiving a signal. Although, in the following the described examples may refer to biosignals as the signal received by a modular recording site, the examples are not limited hereto but relate in general to other types of analogue signals such as, e.g., an optical signal or an electrical signal. A biosignal may be any signals in living beings that can be continually measured and monitored. The term biosignal may be used to refer to bioelectrical signals, but it may refer to both, electrical (e.g., electrochemically triggered) and non-electrical signals such as electrochemical signals or optical signals. A biosignal may in particular be or at least comprise an electrical signal, a signal being based on a biochemical reaction and/or an optical signal or stimulus. The sensor array may detect such a biosignal and may provide for a sensor signal based thereon. Thus, although the described examples may refer to neuronal probes which may be configured for receiving a neuronal signal, the examples are not limited hereto.

FIG. 1 shows a schematic view of a neuronal probe 100 according to an embodiment of the present invention. The neuronal probe 100 comprises a base 110, i.e., a biomedical sensor base, in particular a neuronal probe base, configured for providing a probe signal 112. The neuronal probe 100 also comprises a plurality 120 of modular recording sites. The plurality 120 of modular recording sites comprises modular recording sites $122_1$ to $122_n$. The sub-index n is, for example, an integer of at least 2, advantageously at least ten and more advantageously at least 50 such as 50, 70, 100 or more, e. g. 144, wherein it is also possible that the sub-index n is an arbitrary integer above 144. For convenience, each modular recording site will be identified by $122_e$. Each modular recording site $122_e$ of the plurality 120 of modular recording sites is configured for receiving a neuronal signal or biosignal 130, wherein each modular recording site $122_e$ can receive neuronal signals $132_1$ to $132_n$. The neuronal signals $132_1$ to $132_n$ can comprise at least two of the neuronal signals $132_1$ to $132_n$, which are similar or the same or all neuronal signals $132_1$ to $132_n$ are different with respect to each other. Each modular recording site $122_e$ of the plurality 120 of modular recording sites is configured for converting the received neuronal signal $132_1$ to $132_n$ into a digital sensor signal $134_1$ to $134_n$. Each modular recording site $122_e$ of the plurality 120 of modular recording sites is configured for providing the respective digital sensor signal $122_1$ to $122_n$ to the base 110. The base 110 is configured for receiving a plurality of digital sensor signals $122_1$ to $122_n$ from the plurality 120 of modular recording sites and to process the plurality of digital sensor signals $134_1$ to $134_n$ so as to provide the probe signal 112.

The neuronal probe 100 may be used as a tissue penetrating probe for high density deep-brain recording of in vivo neural activity and overcomes a limitation by the level of electronic integration on the probe shank. Active probes are, in the prior art, used to improve the signal quality and reduce parasitic effects in situ, but still need to route these signals from the electrodes to a base where the readout electronics is located on a large area [4, 6]. The neuronal probe 100 comprises the conversion of the received neuronal signal $132_1$ to $132_n$ into a digital sensor signal $134_1$ to $134_n$ in each modular recording site $122_e$ of the plurality 120 of modular recording sites, so that the base 110 does not need this component and therefore, the base 110 can be implemented on a small area.

Figures 1, 20A:
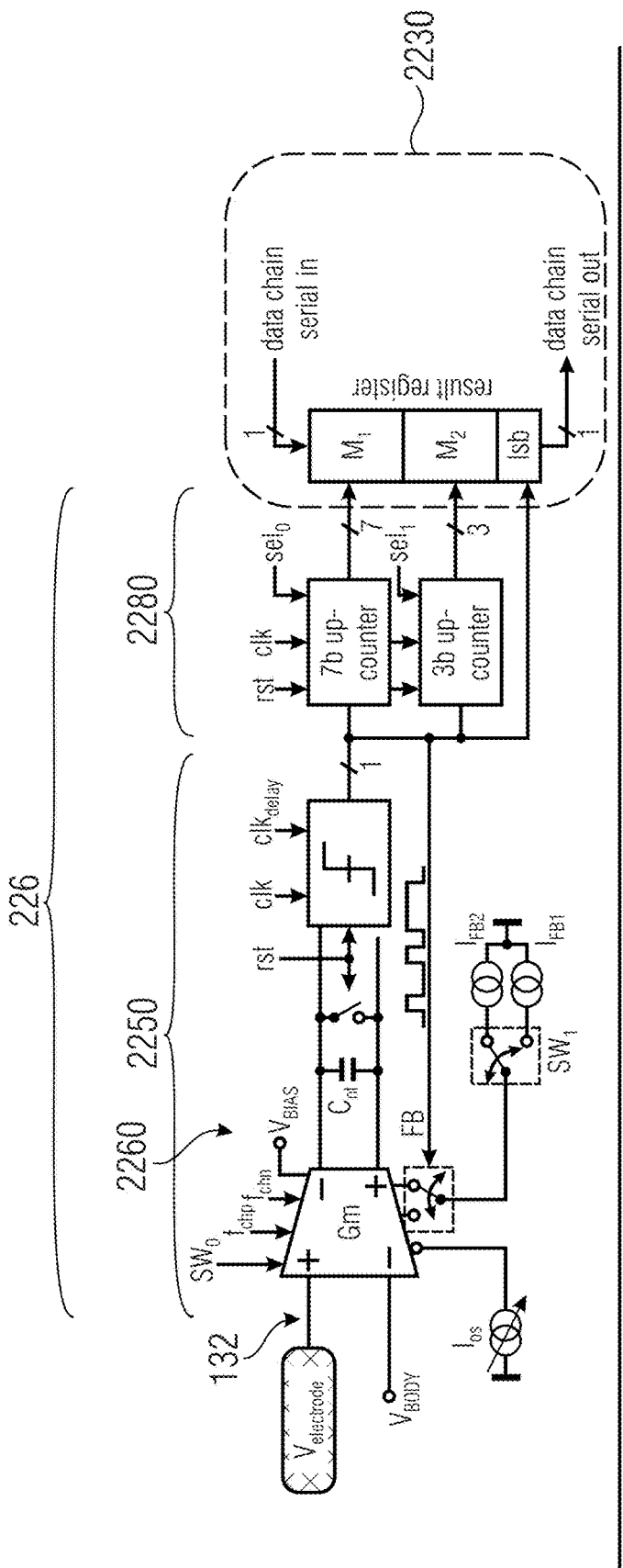
Figures 2, 20A:
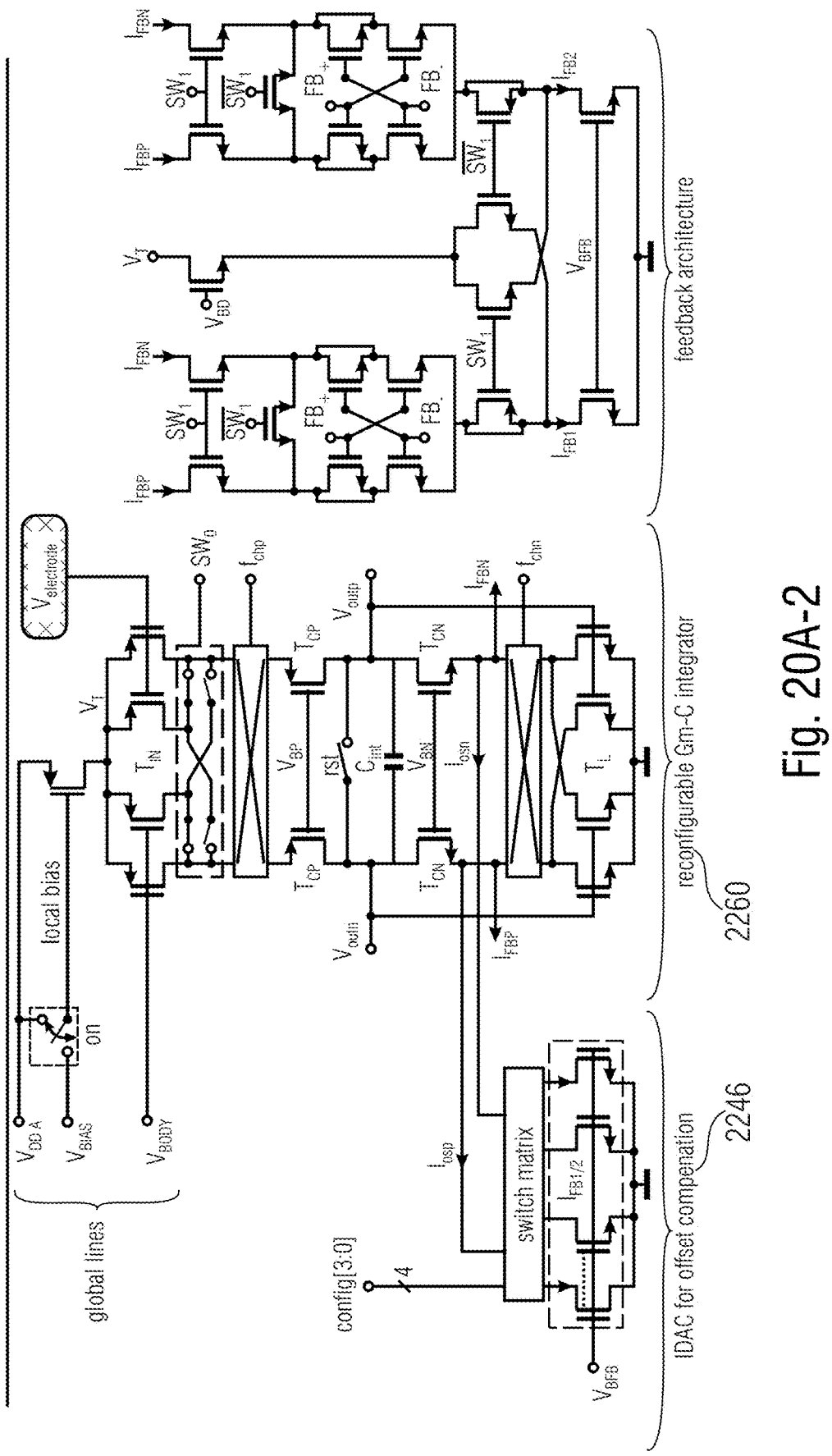
Figure 20B:
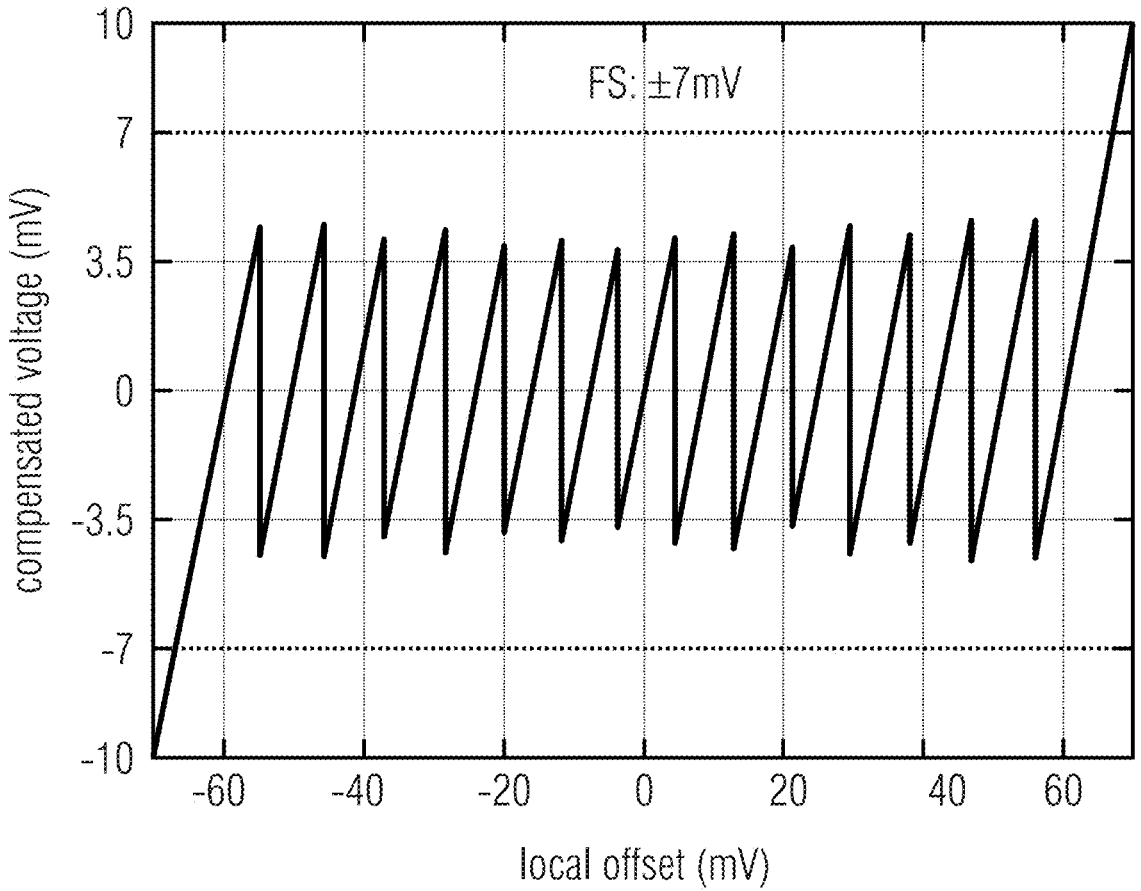
FIG. 20b show a diagram of a local offset compensable by an offset compensation integrated in a two-step in-situ analog-to-digital converter.

FIG. 2$a$ shows a block diagram of a neuronal probe 200 and FIG. 2$b$ shows a schematic view of a neuronal probe 200.

The neuronal probe 200 in FIG. 2$a$ comprises a base 210, a plurality 220 of modular recording sites and, for example, a tip 230. Each modular recording site $224_1$ to $224_n$ of the plurality 220 of modular recording sites comprises a sensor element $222_1$ to $222_n$, an in-situ analog-to-digital converter $226_1$ to $226_n$ and a bi-directional serial digital data bus $228_1$ to $228_n$. The base 210 of the neuronal probe 200 comprises a reference 212, an electrical power supply 214, a digital interface/control unit 216 and a peripheral interface/contacting 218 (pads), wherein the reference 212, for example, provides a ground potential or an arbitrary reference potential for each of the modular recording sites $224_1$ to $224_n$, the electrical power supply 214 provides power for each of the modular recording sites $224_1$ to $224_n$ and the electrical power supply 214 forms with the reference 212 a differential input for the analog-to-digital converter $226_1$ to $226_n$ and the digital interface/control unit 216 is connected to each bi-directional serial digital data bus $228_1$ to $228_n$ of each of the modular recording sites $224_1$ to $224_n$ and configured for providing configuration data to the plurality 220 of modular recording sites allowing for adjusting of, for example, the operation of each of the in-situ analog-to-digital converter $226_1$ to $226_n$ of each of the modular recording sites $224_1$ to $224_n$. The main function of the tip 230 is, for example, to get easier into tissue. The plurality 220 of modular recording sites is, for example, able to receive a neuronal signal with different sensor elements $222_e$ to $222_n$.

Figures 2A, 2B:
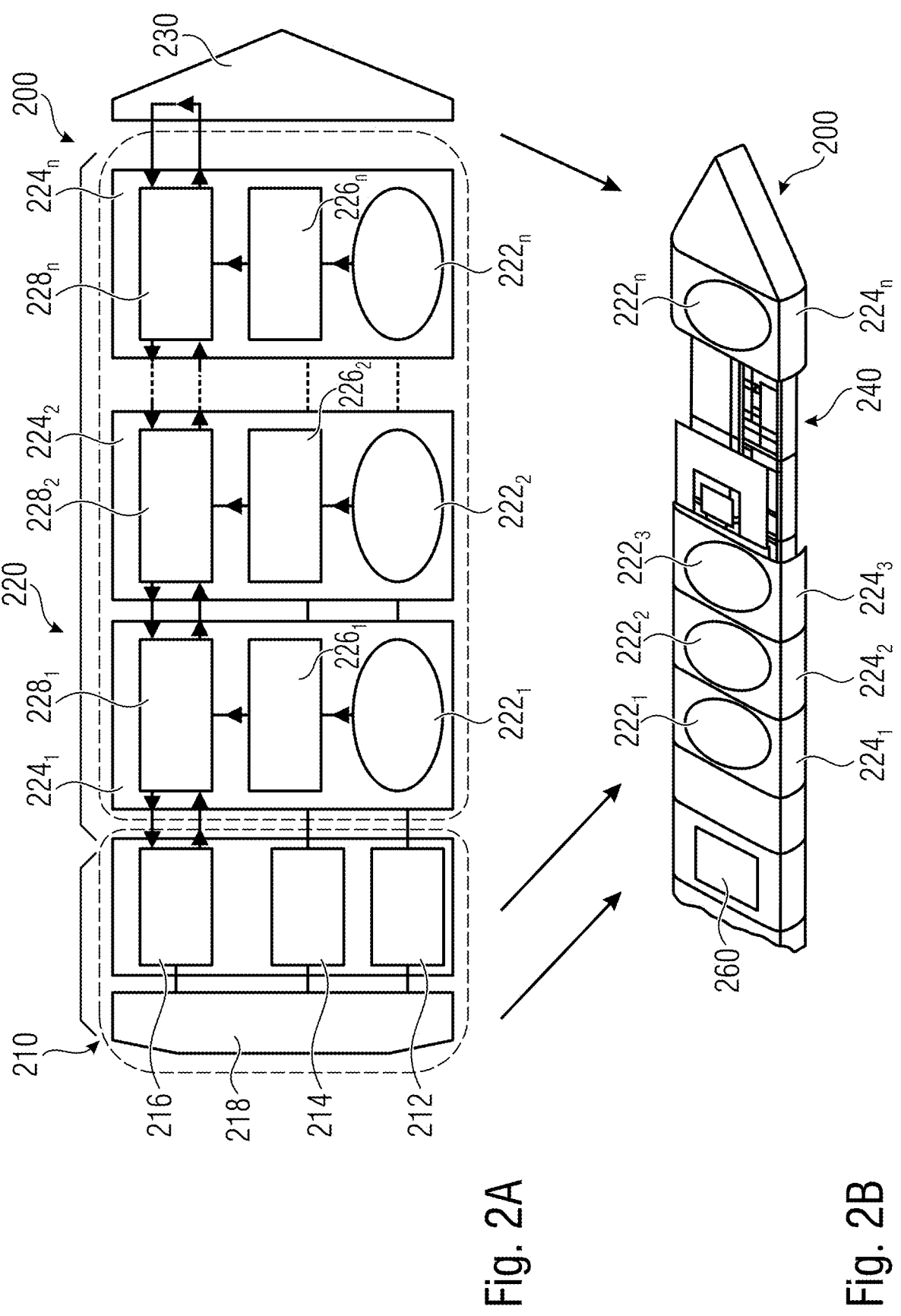

FIG. 2a shows a schematic configuration of a neuronal probe 200 as a modular readout circuit. The modular recording sites $224_1$ to $224_n$ are an arbitrary number and may comprise sensors or sensor elements $222_1$ to $222_n$, optionally electrodes (which receive neuronal pulses as a voltage), optical sensors or chemical sensors. Each modular recording site $224_1$ to $224_n$ is configured to receive a neuronal signal over the sensor element $222_1$ to $222_n$, to convert the received neuronal signal with the in-situ analog-to-digital converter $226_1$ to $226_n$ into a digital sensor signal and to transfer this digital sensor signal in a bi-directional serial digital data bus $228_1$ to $228_n$ to a digital interface/control unit 216 of the base 210. The digital interface/control unit 216 is configured for receiving a plurality of digital sensor signals from the plurality of modular recording sites $224_1$ to $224_n$ over a bi-directional serial digital data bus $228_1$ to $228_n$ and to process the plurality of digital sensor signals so as to provide a probe signal to a peripheral interface/contacting 218, whereby the peripheral interface/contacting 218 is configured to make a connection with an external device and send the probe signal to the external device.

FIG. 2b shows a schematic view of a neuronal probe 200. The neuronal probe 200 comprises a plurality of modular recording sites $224_1$ to $224_n$, wherein each modular recording site $224_1$ to $224_n$ comprises a sensor element $222_1$ to $222_n$. The sensor elements $222_1$ to $222_n$ are connected to electronics 240 under each sensor element $222_1$ to $222_n$ with a sensor contact area 250. At one end of the neuronal probe, the neuronal probe comprises pads 260 which are, for example, used as a peripheral interface/contacting 218. With the peripheral interface/contacting 218 the probe is connected to a cable and by that to a remote device. The sensor elements $222_1$ to $222_n$ can, for example, receive a neuronal signal and transfer the neuronal signal over the sensor contact area 250 to the electronics 240 under the sensor elements $222_1$ to $222_n$. The electronics 240 under each sensor element $222_1$ to $222_n$ can, for example, process the received neuronal signal and convert the neuronal signal into a (digital) sensor signal.

Figures 3A, 3B:
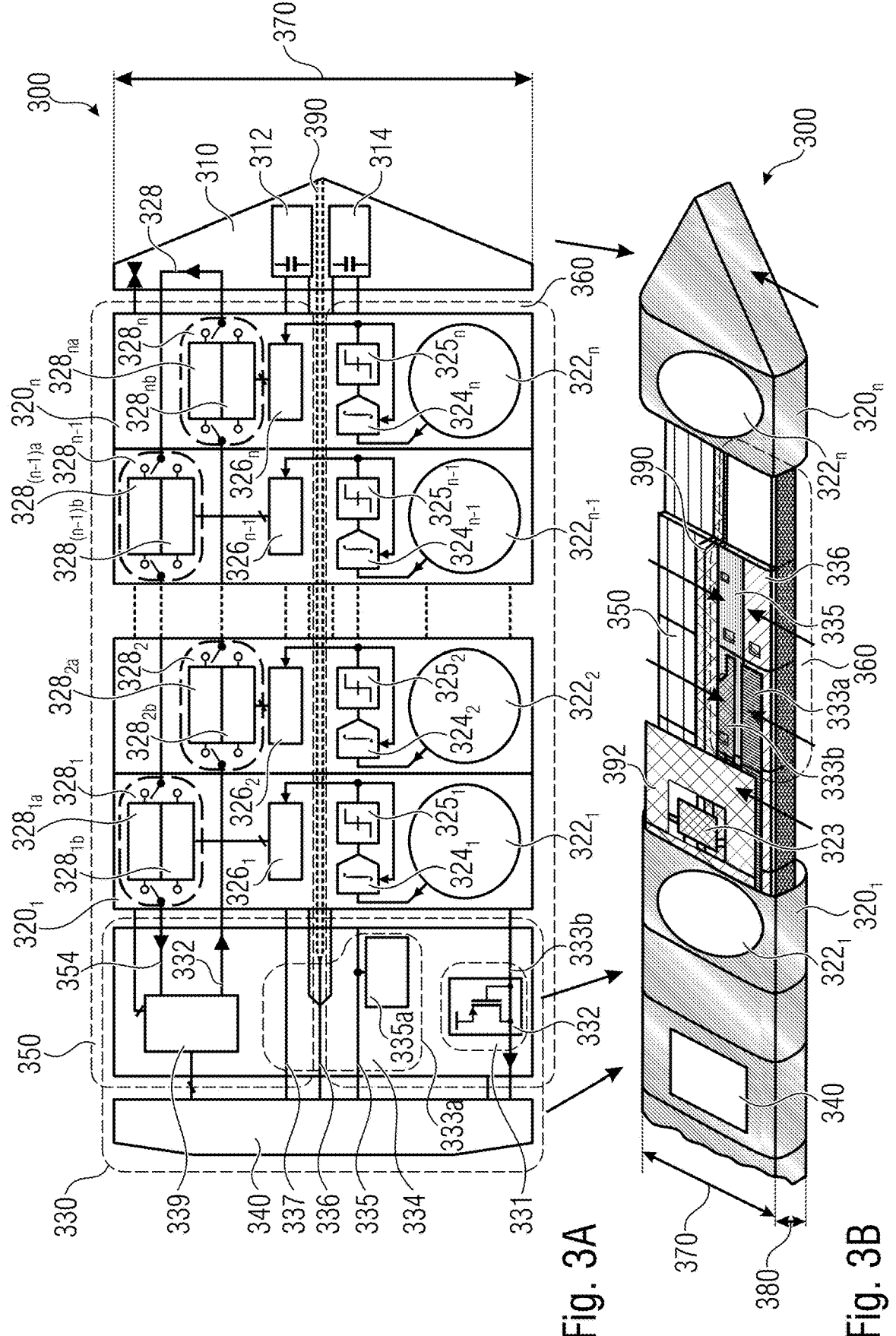

FIG. 3a shows a block diagram of a neuronal probe 300 and FIG. 3b shows a schematic view of the neuronal probe 300.

The neuronal probe 300 of FIG. 3a comprises a tip 310 which has, for example, the same function as the tip 230 in FIG. 2a. A plurality of modular recording sites $320_1$ to $320_n$ which may implement the same function as each of the modular recording sites $224_1$ to $224_n$ of FIG. 2a and FIG. 2b. The neuronal probe 300 further comprises a base 330 which can, for example, have the same functionality as the base 210 of FIG. 2a or the base 110 of FIG. 1. Each modular recording site $320_1$ to $320_n$ comprises a sensor element $322_1$ to $322_n$. The sensor elements $322_1$ to $322_n$ can, for example, have the same functionality as the sensor elements $222_1$ to $222_n$ of FIG. 2a and FIG. 2b. Each modular recording site $320_1$ to $320_n$ also comprises an integrator $324_1$ to $324_n$, a quantizer $325_1$ to $325_n$, a counter $326_1$ to $326_n$ and a bi-directional serial digital data bus 328, wherein the bi-directional serial digital data bus 328 can, for example, have the same functionality as the bi-directional serial digital data bus $228_1$ to $228_n$ of FIG. 2a. The bi-directional serial digital data bus 328 can for each modular recording site $320_1$ to $320_n$ comprise a communication Interface 328, wherein the communication Interface 328 can either be in a configuration mode $328_{1a}$ to $328_{na}$ or in a normal operating mode $328_{1b}$ to $328_{nb}$.

In other words, a digital part 350 of each modular recording site $320_1$ to $320_n$ of the plurality of modular recording sites comprises, for example, the communication interface $328_1$ to $328_n$ which is connected to its neighboring nodes (for example the communication interfaces $328_1$ to $328_n$ of each neighboring modular recording site) by a serial interface. In that way, the converted results (for example, the digital sensor signals) can be linked to the results of the neighboring nodes and can be carried to an external terminal (for example the base 330 or an external device connected to the base) of the overall system (for example, the neuronal probe 300). In that way, for example, the number of connections from one modular recording site $320_1$ to $320_n$ of the plurality of modular recording sites to a neighboring modular recording site $320_1$ to $320_n$ of the plurality of modular recording sites (the modular recording site $320_1$ to $320_n$ can, for example, also be understood as a sensor channel) is kept as low as possible and no analog signal (for example the received neuronal signal by each modular recording site $320_1$ to $320_n$) susceptible to interferences is carried to the outside (for example to the base or to an external device connected to the base) or from the base 330 (for example the outside) into a modular recording site $320_1$ to $320_n$ (for example also understood as a sensor node). Since all neuronal signals (this may be an electrode signal or a sensor signal) are digitized (this means, for example, that each neuronal signal received by a modular recording site $320_1$ to $320_n$ of the plurality of modular recording sites $320_1$ to $320_n$ is converted into a digital sensor signal) directly on-site (for example on each modular recording site $320_1$ to $320_n$) the neuronal probe 300 (respectively, the system) requires only a very small number of lines to the outside (this can, for example, include lines from the base 330 to an external device but it can also include, for example, lines from each modular recording site $320_1$ to $320_n$ to the base 330). Thus, the neuronal probe 300 not only reduces the complexity but also the size of the base 330 and shank (for example, the plurality of modular recording sites $320_1$ to $320_n$ with the tip 310) of the neuronal probe 300, because only a reduced number of lines from each modular recording site $320_1$ to $320_n$ of the plurality of modular recording sites $320_1$ to $320_n$ is needed to transfer a digital sensor signal to the base 330. The serial connection of the communication interfaces $328_1$ to $328_n$ of the plurality of modular recording sites $320_1$ to $320_n$ with respect to each other and to the base also enables the neuronal probe to contact an arbitrary number of modular recording sites $320_1$ to $320_n$ (respectively, sensor nodes).

Each of the digital sensor signals from each of the modular recording sites $320_1$ to $320_n$ can be transferred to the base 330 as a combined sensor signal. Each modular recording site $320_1$ to $320_n$, for example, provides the converted neuronal signal as a digital sensor signal to the bi-directional serial digital data bus $328$. Then the digital sensor signal is transferred by the digital data bus $328$ as a combined sensor signal, of all digital sensor signals of the plurality of modular recording sites, to the base $330$, where the base $330$ processes the combined sensor signal to provide a probe signal.

According to an embodiment, the neuronal probe $100$, $200$ and $300$ shown in FIG. $1$, FIG. $2$ and FIG. $3$ can be seen as a sensor array configured for receiving analog signals, like an optical signal or an electrical signal, as an alternative or in addition to the described analog biosignal which may comprise, by way of non-limiting example, a neuronal signal, and is therefore called sensor array $300$ in the following description regarding FIG. $3$.

The sensor array $300$ is according to an embodiment a Pixel-Level ADC (ADC=analog-to-digital converter), which represents, for example, an optical sensor with a conversion of an analog signal to a digital signal at each modular recording site $320_1$ to $320_n$. The inventive sensor array $300$ is optimized with regard to known optical sensors in terms of a self-sufficient analog-to-digital-conversion. Known sensors are based on an electric current (photodiode) to time conversion (time interval of a pulse). The time interval of a pulse respectively the time needed to reach a threshold is measured in known sensors at all sensor knots or nodes at the same time, which results in a parallel link between the sensors and no serial link is possible. A serial link like in an embodiment of the sensor array $300$ will result e.g. in area-efficient and/or cheaper sensors.

The base $330$ of the neuronal probe $300$ may comprises a reference $331$ which can, for example, have the same functionality as the reference $212$ of FIG. $2a$, an electrical power supply $334$ which can, for example, have the same functionality as the electrical power supply $214$ of FIG. $2a$ and a digital interface/control unit $339$ which can, for example, have the same functionality as the digital interface/control unit $216$ of FIG. $2a$. The base $330$ also comprises pads/digital four wire interface $340$ which can, for example, have the same functionality as the peripheral interface/contacting $218$ of FIG. $2a$. The tip $310$ of the neuronal probe $300$ comprises, for example, a first supply buffer $312$ and a second supply buffer $314$.

Each converter (modular recording site $320_1$ to $320_n$) comprises a digital part $350$ and an analog part $360$ and is configured for minimum area consumption. The system (for example, the neuronal probe $300$) is structured in a modular manner: the signal of each electrode (sensor element $322_1$ to $322_n$) is locally converted to a digital output signal independent of the neighboring electrode (sensor element $322_1$ to $322_n$).

In that way, the number of connections to a neighboring module (sensor channel/modular recording site $320_1$ to $320_n$) is kept as low as possible and no analog signals susceptible to interference are carried to the outside or from the outside into the sensor node (sensor element $322_n$ to $322_n$). Since all electrode signals (neuronal signals) are digitized (converted into a digital signal) directly on site, the system (for example, the neuronal probe $300$) requires only a very small number of lines to the outside (for example, to an external device).

Each modular recording site $320_1$ to $320_n$ of the neuronal probe $300$ can receive a neuronal signal with sensor elements $322_1$ to $322_n$ and convert the received neuronal signal into a digital sensor signal by first integrating the neuronal signal by the integrator $324_1$ to $324_n$ and quantization using a quantizer $325_1$ to $325_n$. With the bi-directional serial digital data bus $328$, the digital sensor signal of each modular recording site $320_1$ to $320_n$ is transferred from each modular recording site $320_1$ to $320_n$ to the digital interface/control unit $339$ of the base $330$, where the digital sensor signal is processed by the digital interface/control unit $339$ into a probe signal, wherein the probe signal is transferred over the pads/digital four wire interface $340$ to an external device.

The whole probe (neuronal probe $300$) is separated along its length into a digital $350$ and an analog part $360$ with separate supply routing and optionally a low-impedance ground shield $390$ in between, that also covers the top to increase the robustness against EMI (electromagnetic interferences) and to reduce digital noise coupling.

The supply routing can be realized with the electrical power supply $334$. The supply routing for the analog part $360$ comprises, for example, a voltage $V_{DD,A}$ $335$ with an optional supply buffer $335_a$ and a ground voltage $V_{SS}$ $336$. The supply routing for the digital part comprises, for example, a voltage $V_{DD,D}$ $337$ with the ground voltage $V_{SS}$ $336$. The digital part $350$ may be connected to its neighboring node (neighboring recording site $320_1$ to $320_n$) by a serial interface (communication interfaces $328_1$ to $328_n$). In that way, the converted results may be linked to the results of the neighboring node (neighboring modular recording site $320_1$ to $320_n$) and may be carried to the external terminal (for example an external device or the base $330$) to the overall system. Configuration data can be carried in a linked manner to each sensor node (modular recording site $320_1$ to $320_n$) via the same interface (communication interfaces $328_1$ to $328_n$) for switching the node (for example, the modular recording site $320_1$ to $320_n$) on and off or for changing its scaling, for example. The base $330$ includes, for example, a reference transistor $332$ providing the global voltage biasing $V_{BIAS}$ to all recording sites (modular recording sites $320_1$ to $320_n$) and a finite-state-machine that allows to switch between a configuration mode and a normal operating mode (readout modes) and forwards the internal data (for example the digital sensor signal) and configuration chains to the external unit (for example, an external device). The switching (of the communication interfaces $328_1$ to $328_n$) between the configuration mode $328_{1a}$ to $328_{na}$ and the normal operation mode $328_{1b}$ to $328_{nb}$ is controlled, for example, with a separate control signal. In the configuration mode $328_{1a}$ to $328_{na}$, settings may be readout of a storage, which is, for example, transferred over the bi-directional serial digital data bus $328$ and can be adapted by each modular recording site $320_1$ to $320_n$, while in the normal operation mode $328_{1b}$ to $328_{nb}$ the digital output (the digital sensor signal) of the converter (modular recording site $320_1$ to $320_n$) will, for example, be written in the storage. The storage may be a volatile or non-volatile storage and may comprise, for example, a plurality of transistor elements for storing information. According to embodiments, the configuration data in the configuration mode $328_{1a}$ to $328_{na}$ and the digital data in the normal operation mode $328_{1b}$ to $328_{nb}$ may be transmitted between each modular recording site $320_1$ to $320_n$ and the base $330$ without using a storage by using the bi-directional serial digital data bus $328$ directly.

On the digital side $350$, no global signals have to be routed: the chain signal, as well as the clock, may be forwarded from one block (bi-directional serial digital data bus $328$) to the next one. The clock is slightly delayed from each modular recording site $320_1$ to $320_n$ to each modular recording site $320_1$ to $320_n$ to spread digital supply noise and reduce peak current consumption. The recording sites (modular recording sites $320_1$ to $320_n$) are grouped into blocks of two ADCs (analog-to-digital converter), one connected to the forward chain 352 and one to the backward chain 354 and clock. In the analog part 360, there are only two global reference lines throughout the probe, i.e., the body reference voltage $V_{BODY}$ 333a and $V_{BIAS}$ 333b. The bias voltage (referenced to $V_{DD}$) is routed with large parasitic capacitances to the supply 334 to enhance noise rejection from external sources.

In other words, the modular recording sites $320_1$ to $320_n$ are, for example, grouped into blocks of two modular recording sites (ADCs respectively, analog-to-digital converters comprising, for example, each of the integrators $324_1$ to $324_n$ and each of the quantizer $325_1$ to $325_n$), wherein one modular recording site comprising a first ADC is connected to the forward chain 352 and forward clock and the other modular recording site comprising a second ADC is connected to the backward chain 354 and backward clock. Thus, the serial interfaces (communication interfaces $328_1$ to $328_n$) of every second modular recording site are, for example, connected/coupled to a first chain (for example forward chain 352) and the serial interfaces of all other modular recording sites are connected/coupled to a second chain (for example backward chain 354). The first chain and the second chain are coupled to the base such that the digital sensor signal is transferred to the base.

The analog-digital converter (for example, the integrator $324_1$ to $324_n$ coupled with the quantizer $325_1$ to $325_n$) may be configured with a differential input in order to be largely robust against interferences of the supply voltage (for example, the supply voltage $V_{DD,A}$ 335 with the ground $V_{SS}$ 336 of the electrical power supply 334). Apart from the supply voltage (for example, the electrical power supply 334), two further global lines (for, example, joints) may be used and may be shared by all sensor nodes (modular recording sites $320_1$ to $320_n$):

The control voltage (for example, the reference voltage $V_{BIAS}$ 333b): each circuit requires, for example, internally a certain number of constant reference potentials and setting currents. All currents and potentials are, for example, derived from the global adjusting voltage (for example, the control voltage $V_{BIAS}$ 333b) which is distributed to all sensor nodes (modular recording sites $320_1$ to $320_n$) as global line. Since it is a global line to which all sensor modules (modular recording sites $320_1$ to $320_n$) are connected, the same may be provided with large parasitic capacitance. This has a positive effect on possible coupling of noise via this line. Additionally, noise (for example, on the control voltage $V_{BIAS}$ 333b) is suppressed by the differential readout principle. This control voltage (for example, the reference voltage $V_{BIAS}$ 333b) may be used for testing, but in principle it (for example, the reference voltage $V_{BIAS}$ 333b) does not necessarily have to be a global connection and the function can, for example, be implemented under each electrode (sensor element $322_1$ to $322_n$).

The reference voltage (for example, the reference voltage $V_{BODY}$ 333a): One side of the differential input is, for example, connected to the sensor (electrode/sensor element $322_1$ to $322_n$) while the second input is, for example, connected to a reference voltage (for example, the reference voltage $V_{BODY}$ 333a). Possible interferences on $V_{BODY}$ (reference voltage $V_{BODY}$ 333a) can be detected equally on all sensor nodes (modular recording sites) and can hence be filtered out in digital post-processing.

Since even the largest neuronal signals are only in the range of some tens of millivolts and the required linearity is low, a direct conversion using, for example, a continuous-time gm-C based incremental delta-sigma analog-to-digital converter (for example, the integrator $324_1$ to $324_n$ coupled with the quantizer $325_1$ to $325_n$) under each electrode (sensor element $322_1$ to $322_n$) may be implemented using a first-order modulator allowing the implementation on a minimal silicon area, since only one integrator $324_1$ to $324_n$ and capacitor and no accurate time constants, thus no local biasing, are needed. Decimation may be accomplished using a simple ripple counter $326_1$ to $326_n$. The output of the single branch OTA-C integrator $324_1$ to $324_n$ is, for example, connected to the quantizer $325_1$ to $325_n$, i.e., comparator and output latch, driving the switches for the current feedback.

In the following a concrete example of a neuronal probe according to an embodiment is given, such as the neuronal probe 300. The example includes several concrete values of parameters used for implementing the neuronal probe. The values are to be understood as non-limiting example only and therefore they do not limit the embodiments but are merely suitable for a better understanding of the present invention. It is clear that by using further, different or other components other values may be obtained such as different voltages, currents and/or data rates.

The digital part 350 of the ADC (analog-to-digital converter) consists or comprises, for example, of a decimator, i.e., ripple counter $326_1$ to $326_n$, two registers for the 11b (11 bit) conversion result and a 2b (2 bit) configuration register. According to an example the ADC may run for 1024 cycles delivering a 10b result. Before resetting the OTA, the OTA output (for example, the output of the integrator $324_1$ to $324_n$) and the counter $326_1$ to $326_n$, the results may be transmitted using the data bus. For example, the last result of the comparator which represents the final conversion error may be appended as the eleventh bit to the 10 bit result and the obtained 11 bit may be put on the data chain. For example, the bit sequence may be stored in the storage of the bi-direction serial digital data bus 328. Alternatively or in addition, the bit sequence of the digital sensor signals of each modular recording site $320_1$ to $320_n$ may directly be transmitted using the bi-directional serial digital data bus 328. The delayed clock of a following cell (modular recording site $320_1$ to $320_n$) is used for a latch to avoid timing violations between the latch and the comparator. During readout, the digital data (the plurality of digital sensor signals) is shifted through the modular recording sites $320_1$ to $320_n$ and the neuronal probe 300 uses two possibly chains (the forward chain 352 and the backward chain 354), each of them may use the same or different data rate such as at least 15 Mbit/s or at least 20 Mbit/s such as 20.48 Mbit/s. For example both chains (the forward chain 352 and the backward chain 354) may use a bit rate of 20.48 Mbit/s, i.e., $f_s$=20.48 MHz. The FSM in the base 330 may combine the outputs of both chains into a single data stream, e. g., by time multiplexing which yields, for example, at the front-end in the given example. The base 330 may be a low power element and may consume less than 1 W, less than 100 mW or even less than 100 μW, e. g., 37 μW and the power consumption per recording site (modular recording site $320_1$ to $320_n$) may result to less than 1 W, less than 100 mW or even less than 100 μW, e. g., 39.14 μW, of which less than 1 W, less than 100 mW or even less than 100 μW, e. g., 12.77 μW are consumed by the analog part 360.

The 11b ADCs (for example, the integrator $324_1$ to $324_n$ coupled with the quantizer $325_1$ to $325_n$) may be designed to optimize noise performance per area, therefore as much area as possible is dedicated to the noise critical components, i.e., the input (the dedicated area should be less than 1000 $\mu m^2$, or less than 500 μm², or less than 200 μm² such as 171 μm² in the given example) and the load transistors (the dedicated area should be less than 1000 μm², or less than 500 μm², or less than 200 μm² such as 144 μm² in the given example). Only a small area is, for example, dedicated to the feedback current sinks, which are derived from the global bias line. The feedback current determines the full scale (FS) of the ADC (for example, the integrator $324_1$ to $324_n$ coupled with the quantizer $325_1$ to $325_n$) which can be configured to one of three different scopes, for example, one scope of ±15 mV, a second scope of ±30 mV and a third scope of ±55 mV or one scope of ±13 mV, a second scope of ±25 mV and a third scope of ±50 mV, or in one scope of ±12 mV, a second scope of ±23 mV and a third scope of ±46 mV, such as ±11.25 mV, ±22.5 mV or ±45 mV.

FIG. 3b shows a system-level schematic with 3D view of the neuronal probe 300. The housing of the neuronal probe 300 comprises optionally a passivation layer (externally covering the housing and providing electrical insulation for the housing. The passivation layer may spare one or more regions allowing electrical signals passing the housing, e. g., at a location of pads 340 and/or electrodes), only the pad 340 (in FIG. 3b, only one pad is shown but the neuronal probe 300 can also be implemented with more than one pad 340) and the electrodes (sensor elements $322_1$ to $322_n$) may be free of a passivation layer. The signal chain of the readout electronics is getting small by omitting pre-amplification, amplification and filtering and can be replaced by a local analog-to-digital conversion of the sensor signals (neuronal signals). Thereby, an analog-to-digital converter can be implemented below each sensor (electrode/sensor element $322_1$ to $322_n$) directly on the shank. The sensor elements $322_1$ to $322_n$ may be coupled to the electronics under each sensor element $322_1$ to $322_n$ by an electrode contact 323.

Each modular recording site $320_1$ to $320_n$ may be divided into an analog part 360 and a digital part 350. The digital part 350 may be shielded from the analog part 360 by a first conductive element 390, wherein the conductive element is configured to block electromagnetic interferences. The conductive element can, for example, be a low-impedance ground shield. A second conductive element 392 is arranged encircling a connector (electrode contact 323) of the sensor element $322_1$ to $322_n$ so as to shield the analog part 360 and the digital part 350 from the sensor element $322_1$ to $322_n$. Under each sensor element $322_1$ to $322_n$ the reference 331 can be implemented with the control voltage $V_{BIAS}$ 333b and the reference voltage $V_{BODY}$ 333a. The electrical power supply 334 can be implemented as, for example, the analog supply voltage $V_{DD,A}$ 335 and the ground voltage $V_{SS}$ 336.

At least a part of the analog part 360 and at least a part of the digital part 350 are, for example, covered by a sensor element $322_1$ to $322_n$ configured for receiving the neuronal signal. In an embodiment the sensor element $322_1$ to $322_n$ covers the digital part 350 and the analog part 360 centric, but it is also possible, that the sensor element $322_1$ to $322_n$ covers only the digital part 350 or only the analog part 360.

In this embodiment, a modular and scalable architecture of a needle probe is realized, which, instead of routing or pre-buffering noise-sensitive analog signals along the shank, integrates, for example, analog-to-digital conversion under each electrode (sensor element $322_1$ to $322_n$). An area used for such integration may be arbitrary and be influenced by the functionality to be integrated. For example, an area of less than 200×200 μm², less than 150×150 μm² or less than 100×100 μm², such as, for example, 70×70 μm² may be used. The design eliminates the need for any additional readout circuitry at the top of the probe (for example, neuronal probe 300) and connects with a digital 4-wire interface 340. The neuronal probe 300 may be implemented as reconfigurable 11.5 mm neuronal probe (but it is also possible to have larger probes of more than 11.5 mm, more than 14 mm or also more than 20 mm) features a constant width 370 of 70 μm (The width 370 is, for example, smaller than 100 μm, smaller than 90 μm or smaller than 75 μm) and thickness 380 (The thickness 380 is, for example, smaller than 100 μm, smaller than 80 μm or smaller than 60 μm) of 50 μm from top to bottom (for example, from the last modular recording site $320_n$ to the first modular recording site $320_1$ or to the base 330 along an axial extension of the array) for minimal tissue damage with, for example, 144 integrated recording sites (modular recording sites $320_1$ to $320_n$) and can be fully immersed in tissue for deep-brain recording applications.

The plurality of modular recording sites $320_1$ to $320_n$ is arranged along an axial direction and forms an array along the axial direction. An extension along a first perpendicular direction perpendicular to the axial direction is understood as the width 370 and an extension along a second perpendicular direction perpendicular to the axial direction understood as the thickness 380.

In an embodiment, the plurality of modular recording sites $320_1$ to $320_n$ is, for example, arranged along an axial direction and forms an array along the axial direction. An extension of the base 330 along a first perpendicular direction perpendicular to the axial direction is, for example, at most an extension of the plurality of modular recording sites $320_1$ to $320_n$ along the first perpendicular direction. An extension of the base 330 along a second perpendicular direction perpendicular to the axial direction is, for example, at most an extension of the plurality of modular recording sites along the second perpendicular direction.

In other words, an elongation of the base 330 in a direction of an axis of the plurality of modular recording sites $320_1$ to $320_n$ may be not bigger than an elongation of the plurality of modular recording sites $320_1$ to $320_n$ in a direction of an axis of the plurality of modular recording sites $320_1$ to $320_n$. An elongation of the base 330 in a direction perpendicular to an axis of the plurality of modular recording sites $320_1$ to $320_n$ may be not bigger than an elongation of the plurality of modular recording sites $320_1$ to $320_n$ in a direction perpendicular to an axis of the plurality of modular recording sites $320_1$ to $320_n$.

In other words, the cross-section perpendicular to an axis from the base through all modular recording sites $320_1$ to $320_n$ (through the plurality of modular recording sites $320_1$ to $320_n$) to the last modular recording site $320_n$ does not have to change. This has the advantage that one can choose an arbitrary number of modular recording sites $320_1$ to $320_n$ for the plurality of modular recording sites $320_1$ to $320_n$ of the neuronal probe without influencing the cross-section of the base 330. Thus, the base 330 can, for example, have the same cross-section as each of the modular recording sites $320_1$ to $320_n$ of the plurality of modular recording sites $320_1$ to $320_n$. Thus, it is possible to bury/immerse the base 330 completely in the tissue. Thus, the neuronal probe 300 can be placed deeper into the tissue and the invasive surgical procedure may be minimized.

The modular concept allows the realization of any arrangement of sensor nodes (modular recording sites $320_1$ to $320_n$), such as, for example, in the form of a two-dimensional array of a needle having one or multiple columns. Each modular recording site $320_1$ to $320_n$ may be arranged and connected to each other in at least one row or column. When referring again to FIG. 3b, the neuronal probe

300 may comprise a single row of a plurality of modular recording sites, being arranged along an axial direction. According to embodiments, a neuronal probe 300 may comprise more than one row or line of modular recording sites $320_1$ to $320_n$. Within one row or column, the modular recording sites $320_1$ to $320_n$ may be arranged serially to each other so as to avoid parallel communication and to thereby allow for small communication entities. Thus, an axial extension of the neuronal probe 300 along the axial direction may at least be influenced by a number of modular recording sites $320_1$ to $320_n$ arranged along that direction. In contrast, the number of modular recording sites $320_1$ to $320_n$ may have low or even no impact on an extension of the row/column of the neuronal probe 300 along one or more directions perpendicular to the axial direction.

Since only the digital data and no sensitive signals are carrier along the shank, a low amount or even no crosstalk can be measured between the sensors (for example, between each sensor element $322_1$ to $322_n$) or between each modular recording sites $320_1$ to $320_n$ and there is high robustness with respect to external interference sources such as light sources or electromagnetic fields.

The number of lines to the outside may be independent of the number of electrodes (sensor elements $322_1$ to $322_n$) and/or sensor modules (for example, the number of modular recording sites $320_1$ to $320_n$), respectively, and/or independent on the width 370 of the shank.

Since the base 330 of the needle may have the same width 370 as the shank, the same can be introduced into tissue beyond the length of the shank without causing additional damage. Thus, deeper brain areas can be measured when compared with conventional needles.

The neuronal probe 300 can, for example, represent a fully immersible deep-brain neuronal probe with modular architecture and a Delta-Sigma ADC (analog-to-digital converter) integrated under each electrode for parallel readout of, for example, 144 recording sites.

Figure 3C:
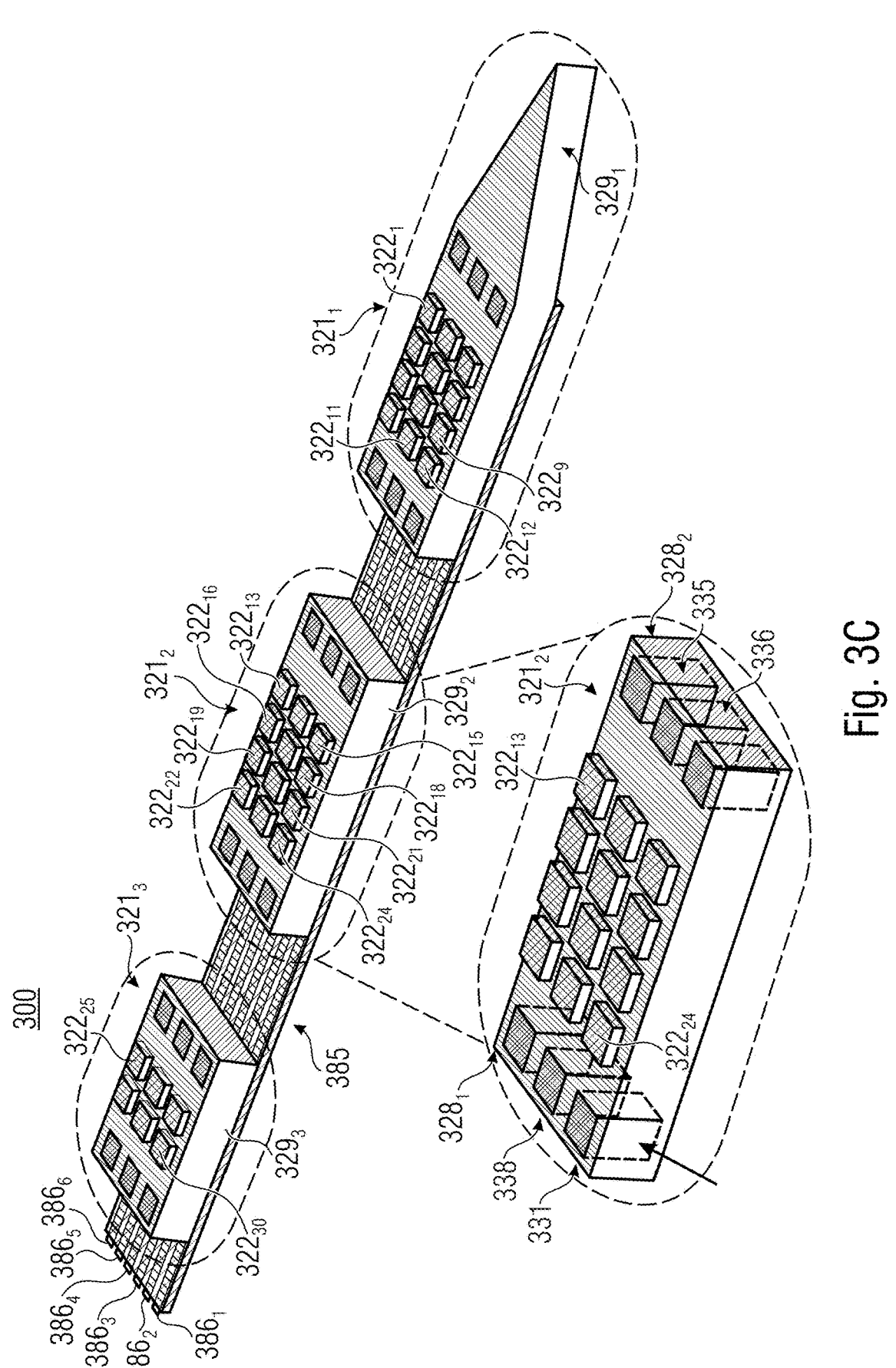
FIG. 3c shows a schematic perspective view of a segmented neuronal probe according to an embodiment of the present invention.

FIG. 3c shows a schematic 3D view of a segmented probe 300 representing an embodiment of the inventive sensor array, wherein the segmented probe 300 can comprise features and functionalities of the neuronal probe 300 shown in FIG. 3a and FIG. 3b. The segmented probe 300 shown in FIG. 3c differs from the neuronal probe 300 in FIG. 3a and FIG. 3b with regard to a positioning of modular recording sites and an arrangement of sensor elements (the sensor elements can also be described as sensor portions or electrodes), as described further below. In FIG. 3c equal or equivalent elements or elements with equal or equivalent functionality, compared to elements shown in FIG. 3a and FIG. 3b, are denoted by equal or equivalent reference numerals even if occurring in different figures.

According to an embodiment the segmented probe 300 shown in FIG. 3c comprises a number of at least two, at least three, at least four or even a higher number such as 10, 20 or the like of segments $321_1$ to $321_3$, wherein each segment $321_1$ to $321_3$ may comprise a number of sensor elements $322_1$ to $322_{30}$. Although being illustrated, for example, as comprising a number of 12 sensor elements $322_1$ to $322_{12}$ or $322_{13}$ to $322_{24}$ being arranged in a 3×4 configuration or a number of 6 sensor elements $322_{25}$ to $322_{30}$ being arranged in a 3×2 configuration any different number of sensor elements and/or any different configuration may be implemented within the scope of the described embodiment. At a tip of the segmented probe 300 is a first segment $321_1$ positioned, then comes a second segment $321_2$, then a third segmented $321_3$, and then more segments can be arranged before, for example, a base is positioned at an end of the segmented probe 300.

According to an embodiment, the sensor array, i.e. the segmented probe 300, comprises a plurality of modular recording sites, for example, represented by the segments $321_1$ to $321_3$ or by the sensor elements $322_1$ to $322_{30}$. For example, one sensor element $322_1$ to $322_{30}$ can represent one modular recording site and/or a group of two or more sensor elements $322_1$ to $322_{30}$ can represent one modular recording site, wherein one modular recording site comprises, for example, one analog-to-digital-converter.

According to an embodiment, a first subset of the plurality of modular recording sites is arranged on a first semiconductor substrate $329_1$, and wherein an adjacent and neighboring second subset of the plurality of modular recording sites is arranged on a second semiconductor substrate $329_2$; wherein the first semiconductor substrate $329_1$ and the second semiconductor substrate $329_2$ are spaced apart from each other by a gap and electrically connected to each other by at least one conductive line $386_1$ to $386_6$. If the first segment $321_1$ represents one modular recording site, this means, for example, that the segment $321_1$ is the first subset of the plurality of modular recording sites, wherein the modular recording site comprises 12 sensor portions $322_1$ to $322_{12}$ and one analog-to-digital-converter. If a sensor element $322_{13}$ to $322_{24}$ or groups of sensor elements (e.g. 2×2, 3×1, 1×3, 3×2, etc.) represent on the second semiconductor substrate $329_2$ two or more modular recording sites, this means, for example, that the two or more modular recording sites represent the second subset. Thus, for example, the second subset on the second semiconductor substrate $329_2$ comprises 4 modular recording sites, if each modular recording site comprises 3 sensor elements $322_{13}$ to $322_{15}$, $322_{16}$ to $322_{18}$, $322_{19}$ to $322_{21}$ and $322_{22}$ to $322_{24}$ with, for example, a 3×1 configuration and wherein each of the 4 modular recording sites comprises one analog-to-digital-converter. In FIG. 3c are shown three semiconductor substrates $329_1$ to $329_3$ which are spaced apart by a gap without semiconductor substrate.

According to an embodiment, the at least one conductive line $386_1$ to $386_6$ is arranged on or in a flexible substrate 385.

According to an embodiment, the segments $321_1$ to $321_3$ are arranged on the flexible substrate 385, like a flexible polymer cable. To improve the flexibility of the segmented probe 300 and to reduce possible damage to the segmented probe 300 by bending or twisting the probe, a gap between the segments $321_1$ to $321_3$ can be adjusted. The larger the gap, the more flexible is, for example, the segmented probe 300.

According to an embodiment a segment $321_1$ to $321_3$ comprises contacts, which connect each segment $321_1$ to $321_3$ to the flexible polymer cable 385, the flexible polymer cable thereby interconnecting the segments, e.g., in a serial way. According to an embodiment signals and/or a power supply is provided for each segment $321_1$ to $321_3$ by the base through the flexible polymer cable 385 and each segment $321_1$ to $321_3$ is, for example, configured to transmit signals by the flexible polymer cable 385 to the base, wherein the segments $321_1$ to $321_3$ are, for example, connected serially by the flexible polymer cable 385. Each segment $321_1$ to $321_3$ comprises, for example, a number of interfaces or contacts $328_1$, $328_2$, 331, 335, 336 and/or 338. Whilst being illustrated as having six contacts, embodiments are not limited hereto as any number of contacts, i.e., more or less, may be implemented so as to transmit signals and/or provide for power supply. For example, a first contact 331 represents a reference, e.g. a reference voltage, a second contact 338 represents a clock, a third contact $328_1$ represents a data input, a fourth contact $328_2$ represents a data output, a fifth contact 335 represents a voltage supply and a sixth contact 336 represents a ground, e.g. a ground voltage.

According to an embodiment, the segments $321_1$ to $321_3$ can comprise a CMOS silicon substrate $329_1$ to $329_3$, in which the electronics of the proposed sensor array, i.e. the segmented probe, is implemented. Optionally the six contacts or at least some of the six contacts 331, 338, $328_1$, $328_2$, 335 and/or 336 can be realized as through-silicon vias.

Figure 4A:
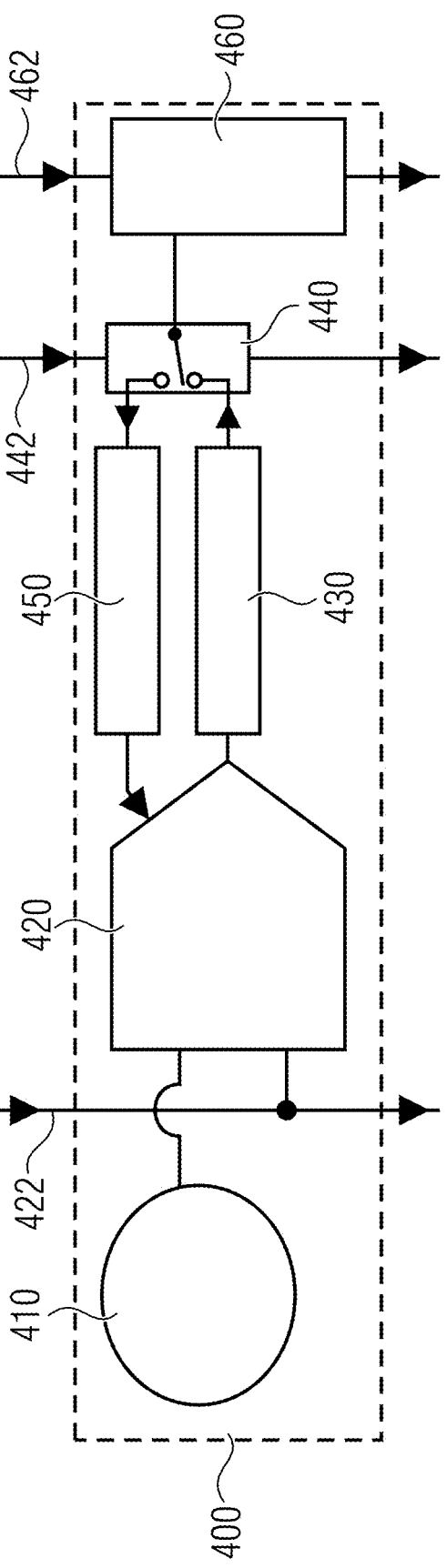
FIG. 4a shows a schematic block diagram of a modular recording site according to an embodiment of the present invention.

FIG. 4a shows a block diagram of a modular recording site 400, wherein the modular recording site 400 has the same functionality as each of the modular recording sites $122_1$ to $122_n$ of FIG. 1, each of the modular recording sites $224_1$ to $224_n$ of FIGS. 2a and 2b and of the modular recording sites $320_1$ to $320_n$ of FIGS. 3a and 3b. The modular recording site 400 comprises a sensor element 410 which can, for example, have the same functionality as each of the sensor elements $322_1$ to $322_n$ of the neuronal probe 300 in FIG. 3a. The sensor element 410 is, for example, coupled to a continuous-time Gm-C Delta-Sigma modulator 420. The time-continuous Gm-C Delta-Sigma modulator 420 can, for example, have the same functionality as the integrator $324_1$ to $324_n$ of FIG. 3a. The continuous-time Gm-C Delta-Sigma modulator 420 can, for example, have a differential input comprising a connection to a sensor element 410 and a connection to a global reference 422. The global reference 422 can, for example, consist of or comprise the reference voltage $V_{BODY}$ 333a of the reference 331 in FIG. 3a which represents the reference potential of the brain tissue towards which neural activity is measured. The -continuous-time Gm-C Delta-Sigma modulator is, for example, configured for transferring an output signal to a quantizer 430.

The quantizer 430 can, for example, have the same functionality as each quantizer $325_1$ to $325_n$ of FIG. 3a. The quantizer 430 may be coupled to a control unit 440, wherein the control unit 440 can, for example, interact with a control signal 442. The control unit 440 may be coupled to a configuration module 450 and storage 460.

The sensor element 410 of the modular recording site 400 can, for example, receive a neuronal signal and transfer the neuronal signal to the continuous-time Gm-C Delta-Sigma modulator 420. The continuous-time Gm-C Delta-Sigma modulator 420 can then, for example, integrate the neuronal signal and send the integrated neuronal signal to the quantizer 430, wherein the quantizer 430 can, for example, decimate the integrated neuronal signal and convert the neuronal signal into a digital sensor signal. The control unit 440 is, for example, configured to be either in a normal operating mode or in a configuration mode. The control signal 442 may tell the control unit 440 which mode is appropriate. When the control unit operates in the normal operating mode, the digitized sensor signal from the quantizer 430 may be written in the storage 460 and transferred by a digital data bus 462 to a base. When the control unit 440 operates in the configuration mode, the control unit 440 may transmit configuration parameters to the configuration module 450, wherein the configuration module 450 can thereby, for example, change parameters for operating each modular recording site such as, for example, the scaling of the continuous-time Gm-C Delta-Sigma modulator 420 is changed.

In other words, the communication interface (for example, control unit 440 and the storage 460) can, for example, operate either in a configuration mode or in a normal operating mode. The switching between the configuration mode and the normal operating mode can, for example, be carried out by a separate control signal. In the configuration mode, the setting of each modular recording site can, for example, be read out of the received configuration data and be used by each modular recording site for adapting a parameter relating to the operation of the modular recording site 400. In a normal operating mode of the communication interface of each modular recording site of the plurality of modular recording sites, the digital sensor signals can be transferred to the base. With the implementation of the communication interface in each modular recording site it is possible to operate each modular recording site individually and to change parameters regarding the conversion of the neuronal signal into a digital sensor signal.

For example, a digital data bus 462 comprising a storage 460 (the storage 460 is, for example, a transistor) couples the communication interface of each modular recording site of the plurality of modular recording sites serially with respect to each other and to the base. The line for the control signal 442 and the line for the digital data bus 462 do not necessarily have to be individual lines. It is, for example, possible to transmit the control signal 442 using the data bus 462. If the communication interface is in a normal operating mode the digital sensor signal converted by each modular recording site of the plurality of modular recording sites from the neuronal signal can, for example, be written in the storage 460 of the digital data bus 462. The digital data bus 462 then, for example, transfers the storage with the digital sensor signal to the base. The communication interfaces of each modular recording site of the plurality of modular recording sites are connected serially with respect to each other and to the base. This can mean that each communication interface of each modular recording site writes the respective digital sensor signal in the storage 460 of the digital data bus 462, so that the digital sensor signals of each modular recording site are arranged in sequence respective to a position of each modular recording site with respect to a position of each other modular recording site. With a separate control signal, the communication interface can change its mode from a normal operation mode (where the digital sensor signal is transferred from each modular recording site to the base) to configuration mode (where configuration data is transferred from the base to each modular recording site). Thus, this modular system concept allows, for example, the contacting of an arbitrary number of modular recording sites (for example neuronal electrodes of any topology or geometry) with minimum complexity, a small size of the base and reading out the modular recording sites simultaneously.

In other words, the architecture of an analog-to-digital converter (respectively, the modular recording site 400) resembles the architecture of a time-continuous Gm-C Delta-Sigma modulator. The time-continuous Delta-Sigma modulators are known for their reduced demand of electrical power. An implementation with a Gm-C integrator 420 has additionally the advantage that the area demand can be very small. Furthermore, these converters are known that they comprise an implicit anti-aliasing filter effect. Thus, more electrical power and area can be saved, because the necessity for a dedicated anti-aliasing filter as an additionally circuit block can be omitted. The usage of such converters and circuit architecture makes it possible to reduce the signal chain and to put an analog-to-digital converter directly under a sensor element 410.

Figure 4B:
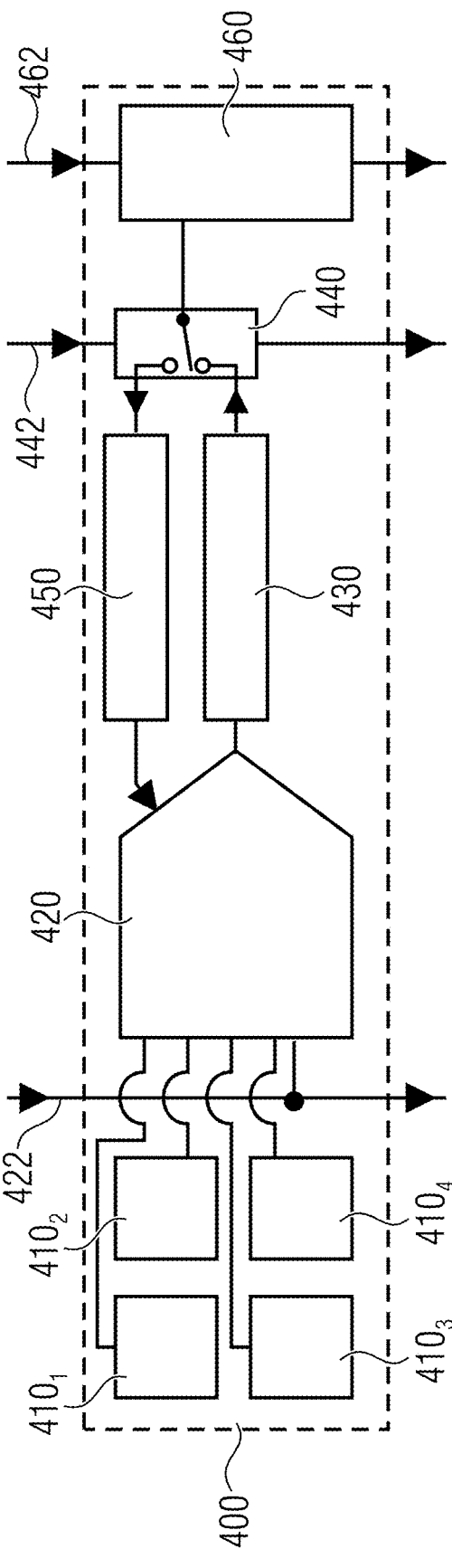
FIG. 4b shows a schematic block diagram of a modular recording site with four sensor elements according to an embodiment of the present invention.

FIG. 4b shows a block diagram of a modular recording site 400, wherein the modular recording site 400 can comprise features and functionalities of the modular recording site 400 shown in FIG. 4a. The modular recording site 400 shown in FIG. 4b differs from the modular recording site 400 in FIG. 4a with regard to the sensor element, wherein the modular recording site 400 of FIG. 4a comprises according to an embodiment at least a second sensor element, by way of example four sensor elements $410_1$ to $410_2$ instead of only one sensor element 410 as in FIG. 4a. The number of four sensor elements is selected for explanatory reasons only and does not limit the scope of the described embodiments. Any other suitable number of two or more, three or more, five or more or even higher numbers such as at least 10 or at least 15 may be implemented. In FIG. 4b equal or equivalent elements or elements with equal or equivalent functionality, compared to elements shown in FIG. 4a, are denoted by equal or equivalent reference numerals even if occurring in different figures. The sensor elements $410_1$ to $410_4$ can also be understood as sensor portions or electrodes.

The at least two sensor elements $410_1$ and $410_2$ are adapted for receiving a signal. The two or more sensor elements $410_1$ to $410_4$ are, for example, arranged in a 2×2-sensormatrix, representing four sensor elements $410_1$ to $410_4$. According to an embodiment all sensor elements $410_1$ to $410_4$ of one modular recording site 400 can detect the same signal, whereby each sensor element $410_1$ to $410_4$ generates for example a different individual signal associated with the same signal, based on a dependency of the same signal on different positions of the sensor elements $410_1$ to $410_4$ at the modular recording site 400. That is, the same signal, the biosignal for example, is received at the different sensor elements $410_1$ to $410_4$ such that the sensor elements $410_1$ to $410_4$ provide for individual, different signal being based on the same biosignal as described in connection with other embodiments of the present invention.

Thus, according to an embodiment, the modular recording site 400 is configured to process four individual signals, associated with the received signal. The individual signals can differ from each other or at least some of the individual signals can be the same. The integrator 420 may integrate the individual signals of the at least to sensor elements $410_1$ and $410_2$ in a time-sequential manner, thereby allowing the modular recording site 400 for sequentially providing an output signal based on two or more sensor elements, i.e., to time-multiplex the information collected with the sensor elements $410_1$ and $410_2$. This may allow for a higher resolution and/or for an oversampling of the signal sensed with the sensor elements $410_1$ and $410_2$ without providing for respective components for conversion of the provided analogue electronic signal into the digital signal.

According to an embodiment FIG. 4b shows an implementation of the modular recording site 400, where one analog-to-digital-converter (e.g. the Gm-C integrator 420 and the quantizer 430) is configured for converting two or more individual provided by the two or more sensor elements $410_1$ to $410_4$. The analog-to-digital-converter is, for example, configured for selectively converting the output of the sensor elements $410_1$ to $410_4$. Time-multiplexing is a widely used method to minimize complexity. According to the described embodiment having a number of sensor elements being four, a four times faster analog-to-digital-converter (when compared to FIG. 4a) can sample and quantize signals received by four sensor elements $410_1$ to $410_4$ in the same time as the analog-to-digital converter described with regard to FIG. 4a converting only one signal. I.e., instead of individually arranging additional converters, a higher conversion speed may be used to group a set of sensor elements.

That is, one, more or all modular recording sites of the probe may be configured for sampling a biosignal with at least a first and a second sensor element and for multiplexing outputs of the first and the second sensor element into the digital sensor signal. Alternatively or in addition to a time-multiplexing, a different or further concept of multiplexing may be implemented, e.g., a frequency-multiplex.

Figure 5A:
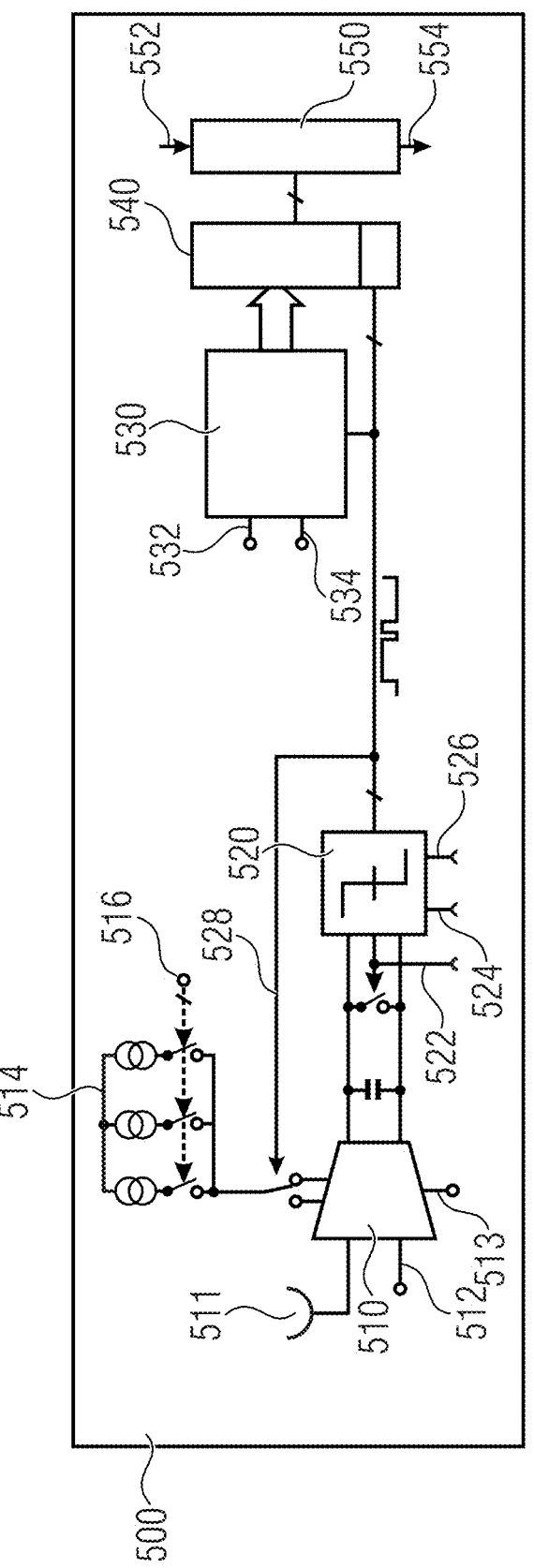
FIG. 5a shows a circuit diagram of a modular recording site with an analog-digital converter according to an embodiment of the present invention.
Figure 5B:
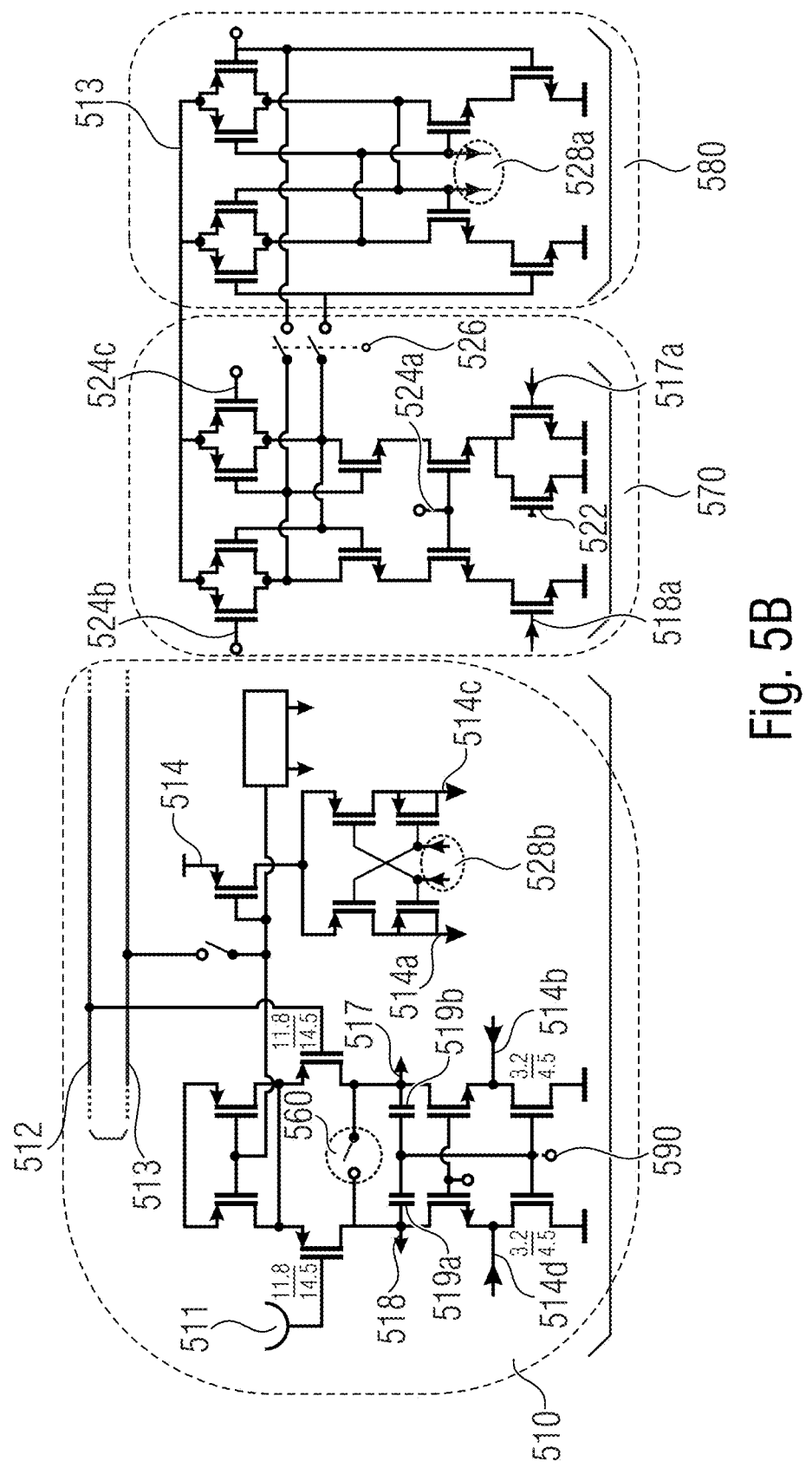
FIG. 5b shows circuit diagrams of components (a Gm-C integrator, a latched comparator and an output latch) of a modular recording site according to an embodiment of the present invention.

FIG. 5a shows a block diagram of a modular recording site 500 and FIG. 5b shows a circuit diagram of a Gm-C integrator 510 with current feedback, a latched comparator 520 and an output latch 530.

The modular recording site 500 from FIG. 5a comprises a Gm-C integrator 510, wherein the Gm-C integrator 510 has, for example, a differential input comprising a contact to a sensor element 511 (for example, an electrode) and to a reference voltage $V_{BODY}$ 512. The integrator 510 is controlled by a control voltage $V_{BIAS}$ 513 and is connected to a supply voltage $V_{DD}$ 514, wherein a full-scale mode select 516 can be applied. The sensor element 511 can, for example, have the same functionality as each of the sensor elements $322_1$ to $322_n$ of FIG. 3a or FIG. 3b, the reference voltage $V_{BODY}$ 512 can, for example, have the same functionality as the reference voltage 333a of FIG. 3a or FIG. 3b and the supply voltage 514 can, for example, have the same functionality as the supply voltage $V_{DD,A}$ 335 of FIG. 3a or FIG. 3b and the control voltage V BIAS 513 can, for example, have the same functionality as the control voltage 333b of FIG. 3a or FIG. 3b. The integrator 510 has a differential output coupled to a quantizer 520, wherein the quantizer 520 can, for example, have the same functionality as each of the quantizers $325_1$ to $325_n$ of FIG. 3a. From the quantizer 520, a feedback current 528 is coupled to the integrator 510 and a bitstream can be sent to a counter 530, wherein the counter 530 can, for example, have the same functionality as each of the counters $326_1$ to $326_n$ of FIG. 3a.

The quantizer 520 may comprise a reset 522, a clock 524 and a delay clock 526, wherein the delay clock 526 connects to the next side in chain (to the next modular recording site). The reset 522, for example, switches a transistor to reset the quantizer 520. Thus, for example, by the quantizer 520 a digitized sensor signal gets delayed in respect to the digital sensor signal of a neighboring modular recording site. The counter 530 is, for example, a ten-bit counter with a reset 532 and a clock 534. The counter 530 writes, for example, the digital sensor signal into a latch 540 (which has, for example, the function of the storage 460 from FIG. 4a and FIG. 4b). The digital sensor signal is then from the latch 540 written into the result register 550, wherein the result register 550 can, for example, have the same functionality as the storage 460 from FIG. 4a and FIG. 4b. Through the input 552, a data chain coming from the base goes into the result register 550 and leaves after receiving an additional digital sensor signal from the latch 540 through the output 554.

In FIG. 5b, the block diagram of FIG. 5a is shown in more detail. The Gm-C integrator is, for example, connected to two global analog lines (the reference voltage $V_{BODY}$ 512 and the control voltage $V_{BIAS}$ 513). The integrator also comprises, for example, the supply voltage $V_{DD}$ 514, wherein the supply voltage 514 creates a current from a first output 514a to a first input 514b and a current from a second output 514c to a second input 514d. The integrator 510 may be connected to a sensor element 511 (for example, an electrode) and can, for example, comprise a reset module 516. The integrator 510 couples, for example, with a latched comparator 570 by a connection between a first differential output 517 to a first differential input 517a and by a second differential output 518 to a second differential input 518a.

The latched comparator 570 comprises, for example, a reset 522, a first clock 524a, a second clock 524b, a third clock 524c and a delay clock 526, wherein the first clock 524a, the second clock 524b, the third clock 524c and/or the delay clock 526 operate cyclically and are, for example, provided with the same signal. The latched comparator 570 is connected with an output latch 580 by the supply voltage $V_{DD}$ 514. The output latch 580 is connected to the integrator 510 by a connection between a feedback output 528a and a feedback input 528b.

The feedback current sinks (for example, the connection between the feedback output 528a and the feedback input 528b) are, for example, derived from the global bias line (control voltage 513). The feedback current, for example, determines the full scale (FS) of the ADC which can be configured to ±11.25 mV, ±22.5 mV or ±45 mV. Depending on the comparator output (for example, the feedback output 528a), the current may be injected either to the left or the right low-impedance cascade node of the OTA (integrator 510). Common mode ripple caused by the asymmetrical feedback may be reduced by connecting the 95 fF MIM integration capacitances (a first MIM (metal/insulator/metal) integration capacitance 519a and a second MIM integration capacitance 519b, wherein the first MIM integration capacitance 519a and the second MIM integration capacitance 519b each occupy, for example, less area than 20×10 $\mu m^2$, 15×7 $\mu m^2$ or 10×4 $\mu m^2$, such as, for example, 7×3.5 $\mu m^2$ and can have a capacitance in the scope of 20 fF to 200 fF, 50 fF to 150 fF or 80 fF to 100 fF, such as, for example, 95 fF) to $V_{CMFB}$ 590 and rejected by the differential comparator input. The noise of the feedback current source and the feedback switches, which may operate at digital-level input signals, is negligible compared to the major noise contributors. The constraints on the area and accuracy of the common-mode feedback is not stringent, first because noise is canceled by the differential nature of the circuit, and second, because no exact common mode is needed at the comparator input (for example, a first input 517a and a second input 518a). The trans-conductance of the differential pair may be determined by thermal noise considerations, e. g., to be in the scope of 1 $\mu S$ to 20 $\mu S$, 2 $\mu S$ to 10 $\mu S$ or 3 $\mu S$ to 5 $\mu S$, such as, for example, 4.2 $\mu S$. A measured maximal SNR may be less than 300 dB, 200 dB or 100 dB, such as, for example, 65.6 dB (FS=±45 mV) and a THD of, for example, less than 5%, 1% or 0.5%, such as, for example, 0.22% at $V_{PP}$=10 mV (FS=±11.25 mV) is obtained for a tail current of 1.5 $\mu A$, according to this example.

In other words, the integrator 510 of each modular recording site of the plurality of modular recording sites is configured to receive the neuronal signal and to integrate the neuronal signal, so as to obtain an integrated neuronal signal. The quantizer 520 of each modular recording site of the plurality of modular recording sites comprises a latched comparator 570 and an output latch 580. The latched comparator 570 is configured to receive the integrated neuronal signal and to quantize the integrated neuronal signal. The output latch 580 is configured to drive switches for a feedback current 528 to the integrator 510, based on the comparator output latch 580. Depending on the comparator output latch 580, the current is injected either to the left or to the right low impedance cascade node of the OTA (the OTA together with a capacitance is an example for an integrator).

FIG. 5b shows, for example, an incremental delta-sigma system-level schematic and transistor-level implementation (for example, the feedback current sources of only one full-scale mode are shown: $I_{FBN}$ (from a first output 514a to a first input 514b), $I_{FBP}$ (from a second output 514c to a second input 514d)).

Figure 6A:
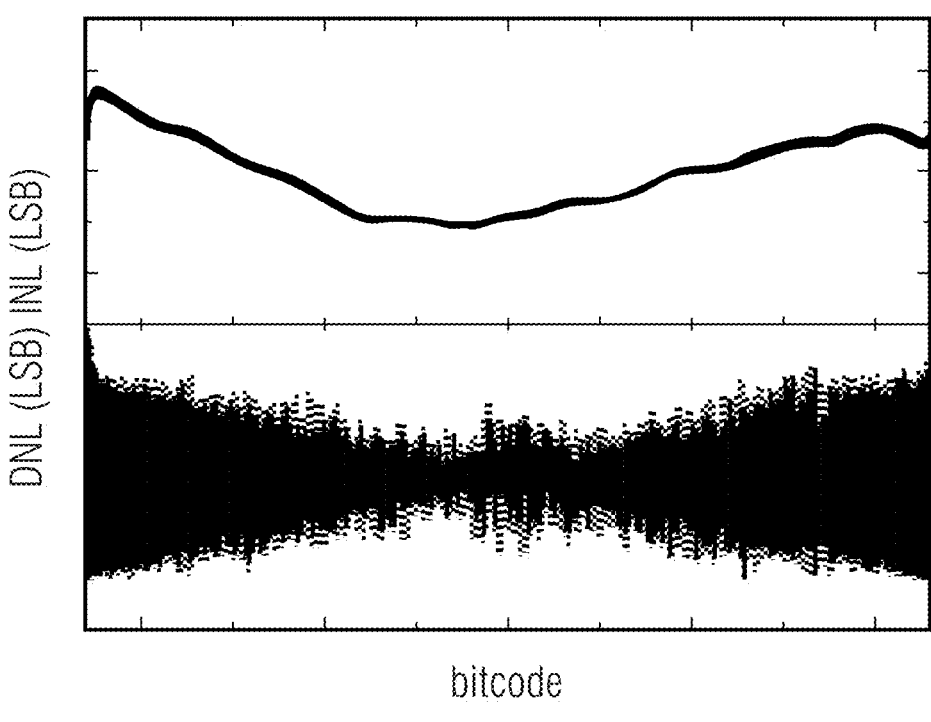
FIG. 6a shows a diagram with measured DNL/INL (differential non-linearity/integral non-linearity) in vitro measurement data measured by a neuronal probe according to an embodiment of the present invention.
Figure 6B:
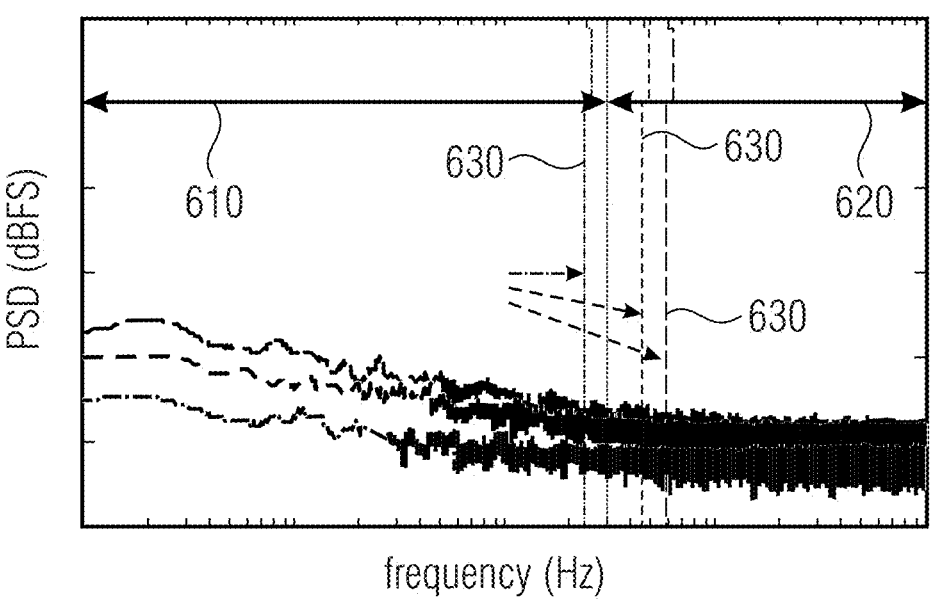
FIG. 6b shows a diagram with an in vitro power spectral density plot measured by a neuronal probe according to an embodiment of the present invention.
Figure 6C:
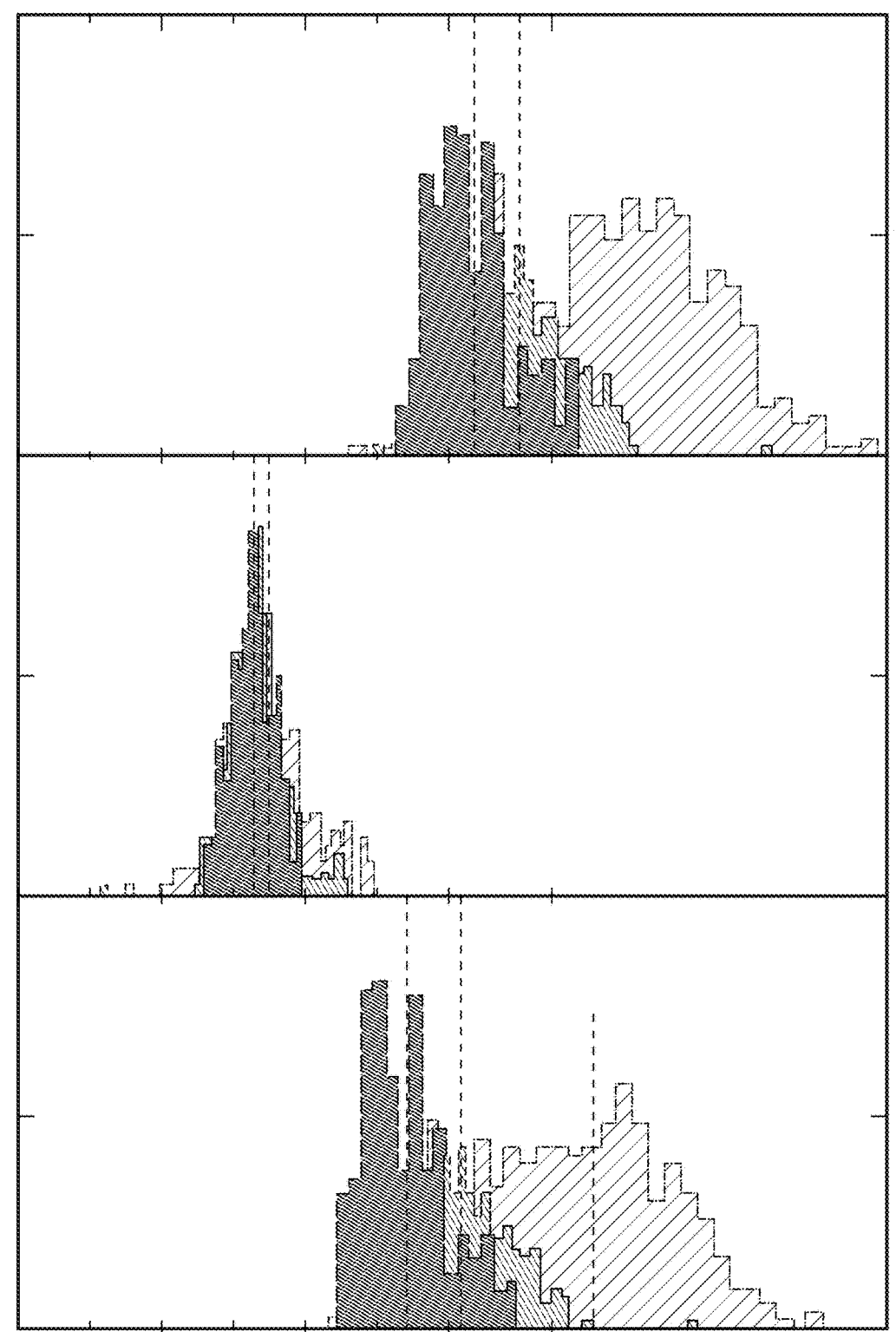
FIG. 6c shows a diagram with a statistical noise distribution of in vitro measurement data measured by a neuronal probe according to an embodiment of the present invention.

FIG. 6a, FIG. 6b and FIG. 6c show diagrams of in vitro measurements, which may be obtained by neuronal probes according to embodiments described herein. Neither the measurement results nor specific details in view of electronic parameters, sizes or numbers given in connection with the embodiments are suitable to limit the teachings given, unless stated otherwise. It is clear that other configurations, parameters, numbers or sizes may be implemented within the scope of the present embodiments.

FIG. 6a shows measured DNL/INL (differential non-linearity/integral non-linearity) for FS=±45 mV. FS means full scale of the ADC (analog-digital converter) which can be configured to ±11.25 mV, ±22.5 mV or ±45 mV.

FIG. 6b shows an in vitro power spectral density plot where the first half 610 corresponds to the LFP band (the band for local-field-potentials) and the second part 620 corresponds to the AP band (action-potential band). FIG. 6b also shows a plurality of noise corners 630.

FIG. 6c shows a statistical noise distribution (384 recording sites—multiple probes). The statistical noise distribution for FS=±11.25 mV is diagrammed in black, for FS=±22.5 mV the statistical noise distribution is shown in light black and for FS=±45 mV the statistical noise distribution is shown in grey. The top most diagram shows the full bandwidth, the middle diagram shows the local field potential band and the lower diagram shows the action potential band. The ADC (analog-digital converter in each modular recording site of a neuronal probe according to an embodiment) covers an input signal bandwidth of 10 kHz with a flicker noise corner between 240 Hz and 590 Hz, depending on the FS mode. The noise in the frequency bands of the two types of neural signals, i.e., local-field-potentials (LFP, 1 to 300 Hz) and action potentials (AP, 0.3 to 10 kHz) are 8.1 $\mu Vrms$ and 13.4 $\mu Vrms$, respectively (FS=±11.25 mV). All measurements are taken in vitro, i.e., include also noise resulting from the electrodes and the electrolyte surface interface, and without any additional shielding.

Figure 7:
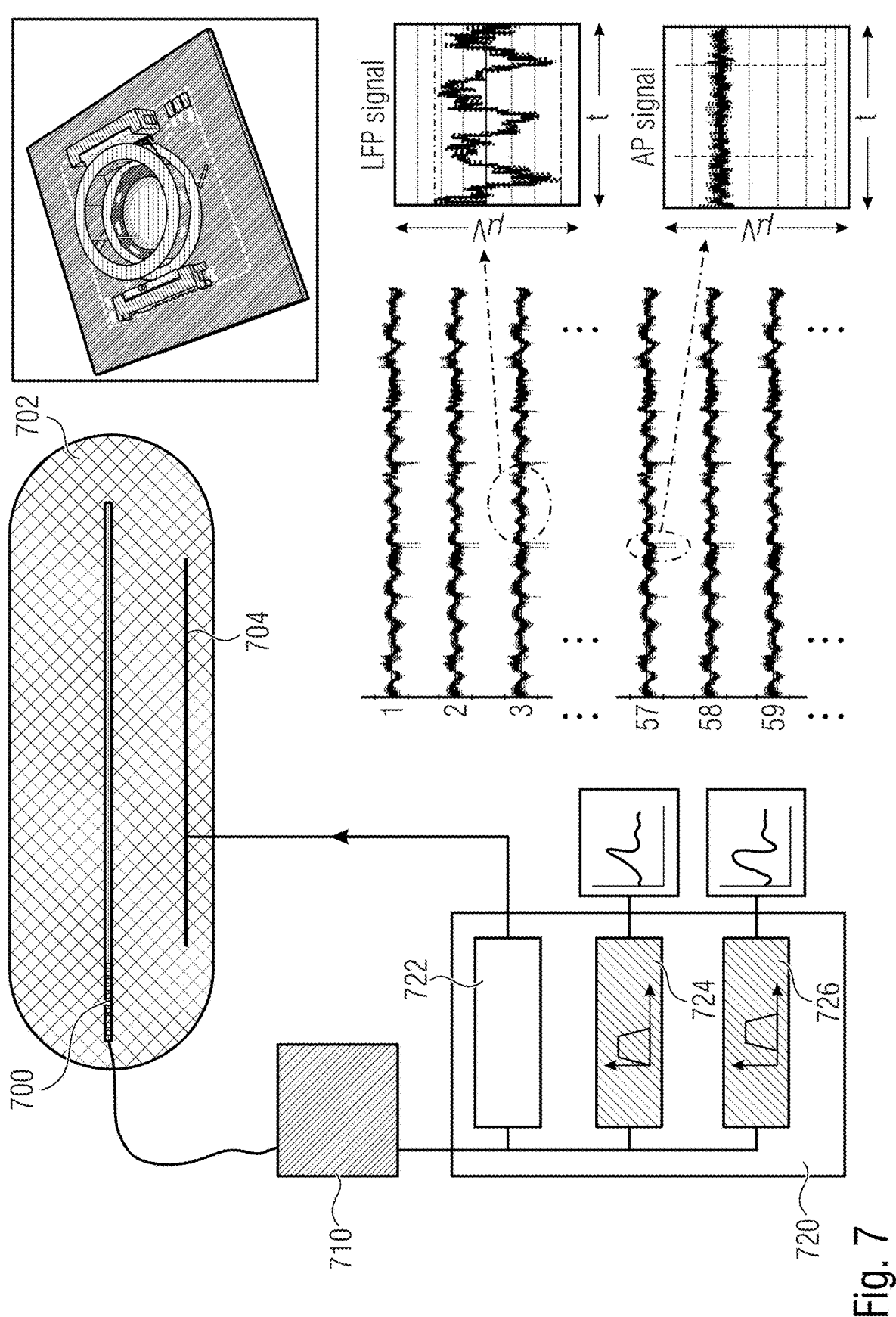
FIG. 7 shows a schematic view of an in vitro measurement setup with a neuronal probe according to an embodiment of the present invention.

FIG. 7 shows an in vitro measurement setup showing DC (direct current) controller/artefact filter and digital post-processing. Measurement results from stimulation with pre-recorded data (hippocampus). The photo on the top right shows in vitro MEA adapter with two needle probes for brain slice activity recording. The neuronal probe 700 (which can, for example, have the same functionalities as the neuronal probe 100, 200 and 300) is put into a phosphate-buffered saline solution 702 with a body voltage $V_{BODY}$ 704. The neuronal probe 700 is connected via a flex-cable to a field-programmable-gate-array 710 (FPGA). The FPGA 710 is connected via USB (universal serial bus) to a post-processing unit 720. The post-processing unit 720 comprises a DC controller artefact filter 722, a LFP filter 724 and an AP filter 726.

In the following, an example measurement is described shortly. The averaged data of all ADCs (analog-digital converter in each modular recording site of a neuronal probe according to an embodiment) is used to drive a proper body voltage for the application in saline solution and for cancellation of artifact signals. The measured signal is separated into low frequency local-field potentials (LFP) and high-frequency action potentials (AP) by digital post-processing.

FIG. 8 shows a photometric and radiometric light sensitivity measurement (average noise of all illuminated recording sites) for optogenetic applications (for comparison: an illuminance of about 500 Lux corresponds to typical office lighting, about 10000 Lux to full daylight). During optoge-netic stimulation an external light source excites specifically brain tissue and therefore, activity can be elicited, which can be detected with the neuronal probe. Generally light pulses also generate in neuronal probes artefact signals. The design of the neuronal probe, as described herein, is implemented such to be to a large extend immune to optical disruptions.

A pulsing (on/off with a frequency of 20 Hz or 1 kHz) broadband light source 810 ($\lambda$=400 nm to 1000 nm) may sends a beam 820 through a neutral density filter 830 onto an active needle probe 800 (the active needle probe 800 can, for example, have the same functionality as the neuronal probe 100, 200 and 300), wherein the active needle probe 800 is placed in a ringer solution 840. In the right diagram the first curve 850 corresponds to a high frequency (for example, 1 kHz) and a second curve 852 corresponds to a low frequency (for example, 20 Hz). In the diagram is also shown the full bandwidth noise limit 854. The shielding and layout concept (as described above) of the neuronal probe according to an embodiment with both input transistors of a differential pair (The differential transistor pair, describes a circuit technique in which two input transistors are used in order to create differential signaling in the signal path.) placed under the electrode suppresses illumination artifacts, which is a strong requirement for optogenetic stimulation of neuronal cells [9]. Sensitivity measurements against pulsing broadband light sources are shown in FIG. 8. The resulting signal shifts during light excitation are consistent with photonic effects on the electrode surface while the CMOS circuit underneath does not further degrade the performance.

Figure 9:
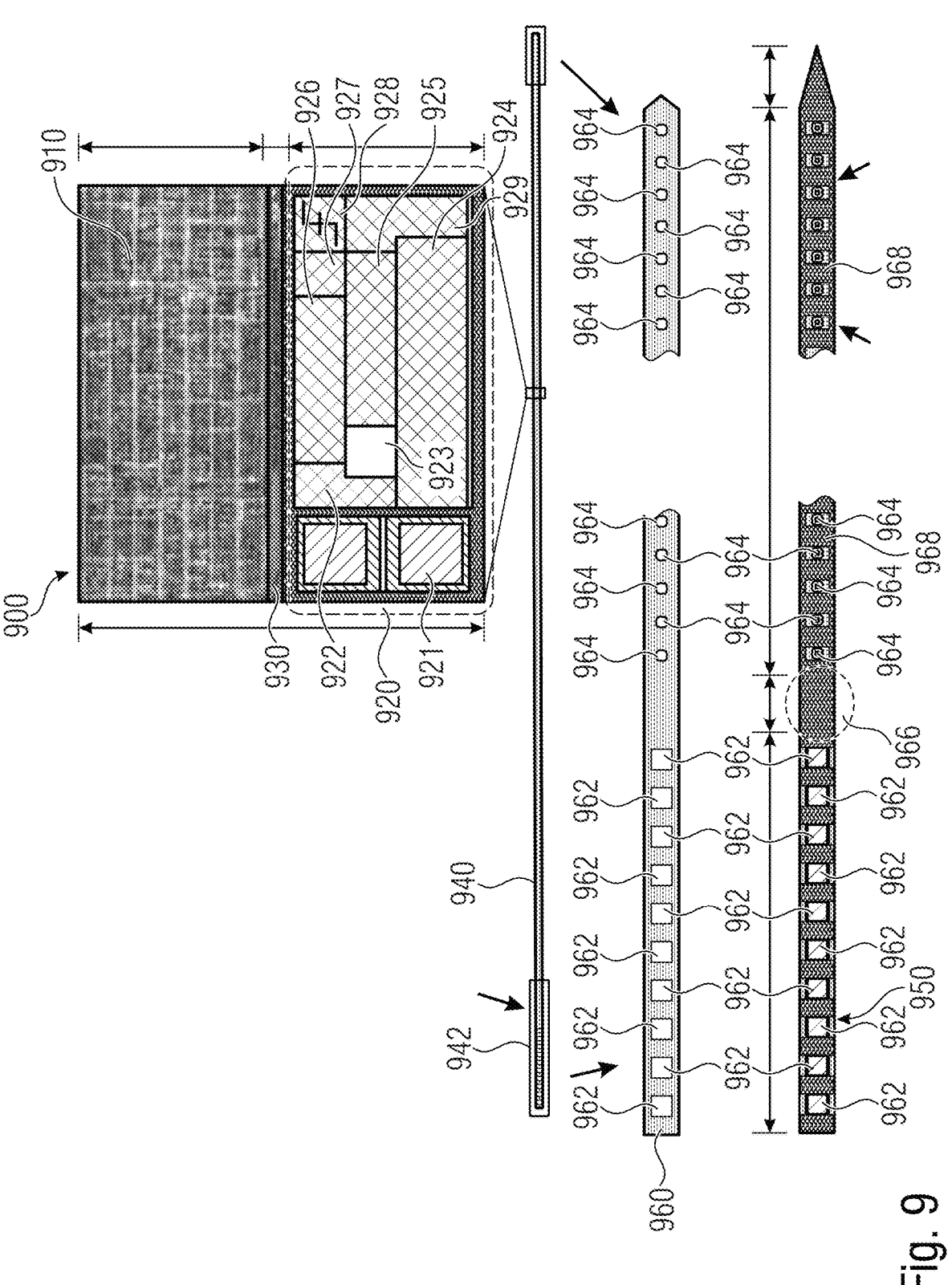
FIG. 9 shows micrographs of a CMOS chip and a neuronal probe according to an embodiment of the present invention.

FIG. 9 shows micrographs showing CMOS chip and final needle probe (an example for a neuronal probe according to an embodiment) after post-CMOS processing (supply volt-ages are tight together off-chip) on the cable. The pad is, for example, used for electrode characterization (for example, cyclic voltammetry or electrochemical impedance spectros-copy), it is not necessarily needed for the read out. One modular recording site 900 of a neuronal probe according to the present invention can be separated in a digital part 910 and an analog part 920 separated by a shield 930. The analog part 920 comprises, for example, a Gm integrator 921, a CMFB 922 (a C 923, a CMOS load 924, switches 925, current bias 926, $V_B$ 927, a quantizer 928 and a configuration module 929).

The neuronal probe 940 comprises an optional first elec-trode 942, wherein the first electrode (for example, a Pt-electrode) can be directly connected to $V_{REF}$ pad for elec-trode characterization. The neuronal probe 960 comprises Pads 962 and sensor elements 964, wherein the Pads 962 are, for example a contacting to connect the neuronal probe 960 to an external device. The neuronal probe 950 comprises Pads 962, sensor elements 964, a base 966 and an optional $Si_3N_4$—$SiO_2$ passivation, wherein the Pads 962 are, for example a contacting to connect the neuronal probe 960 to an external device, the sensor elements 964 are, for example, Pt-electrodes (platinum-electrodes) and the $Si_3N_4$—$SiO_2$ passivation forms an insulating portion 968 between each sensor element 964. The neuronal probe is separated after post-CMOS fabrication.

The micrographs show the fully implantable probe with, for example, a constant width of and thickness of 50 μm from tip to base. The length of the base is, for example, independent on the number of electrodes. The maximal number of recording sites may be solely limited by the data rate of the chain as the clock frequency equals to fs of the ADCs. Each ADC delivers, for example, 20 kS/s, limiting the length to, for example, 93 electrodes per chain. An example probe employs, for example, two data chains (each with, for example, 93 modular recording sites); however, an extension with multiple chains would only add marginal complexity to the digital part. Since no global analog neural signal routing may be present and due to the high modularity of the design, a longer probe or any application-specific modification of the probe geometry would deliver identical performance. Technology scaling would considerably reduce the power dissipation as well as the probe width, since half the probe area is dedicated to the digital circuitry.

Figures 10A, 10B:
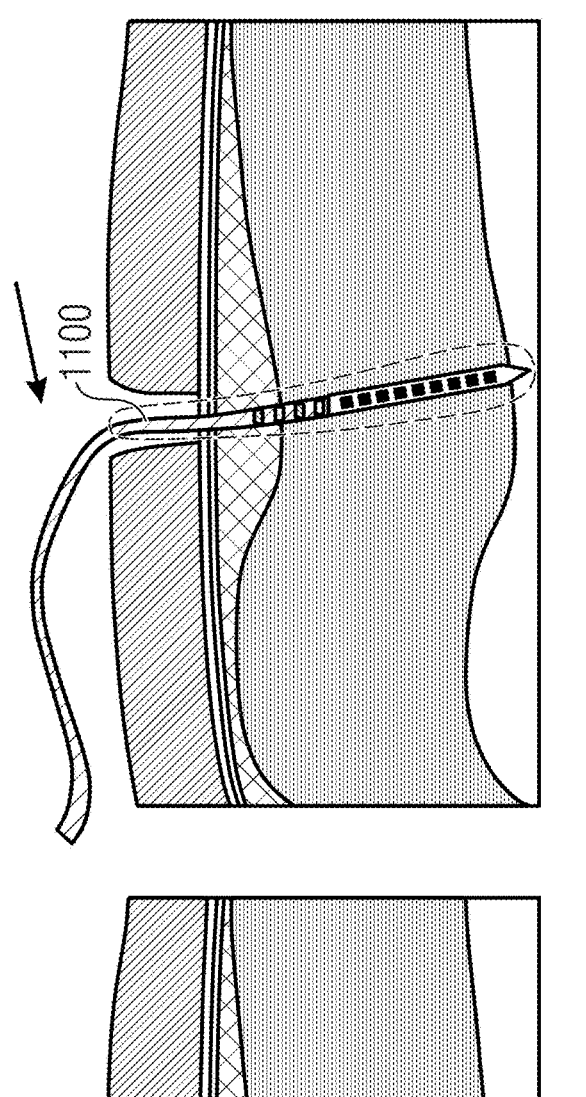
FIG. 10a shows a schematic view of a neuronal probe according to the prior art.
FIG. 10b shows a schematic view of a neuronal probe according to an embodiment of the present invention.

FIG. 10a shows a schematic view of a neuronal probe 1000 as stated in the art. FIG. 10b shows a neuronal probe 1100 according to an embodiment of the present invention. All known solutions have a very large base 1010 and hence cannot completely be buried in the tissue. Additionally, the size of the base 1010 requires an invasive surgical proce-dure. With the neuronal probe 1100, these problems can be overcome. Accordingly, it can be seen that the neuronal probe according to the present invention clearly outperforms conventional solutions.

Figure 11:
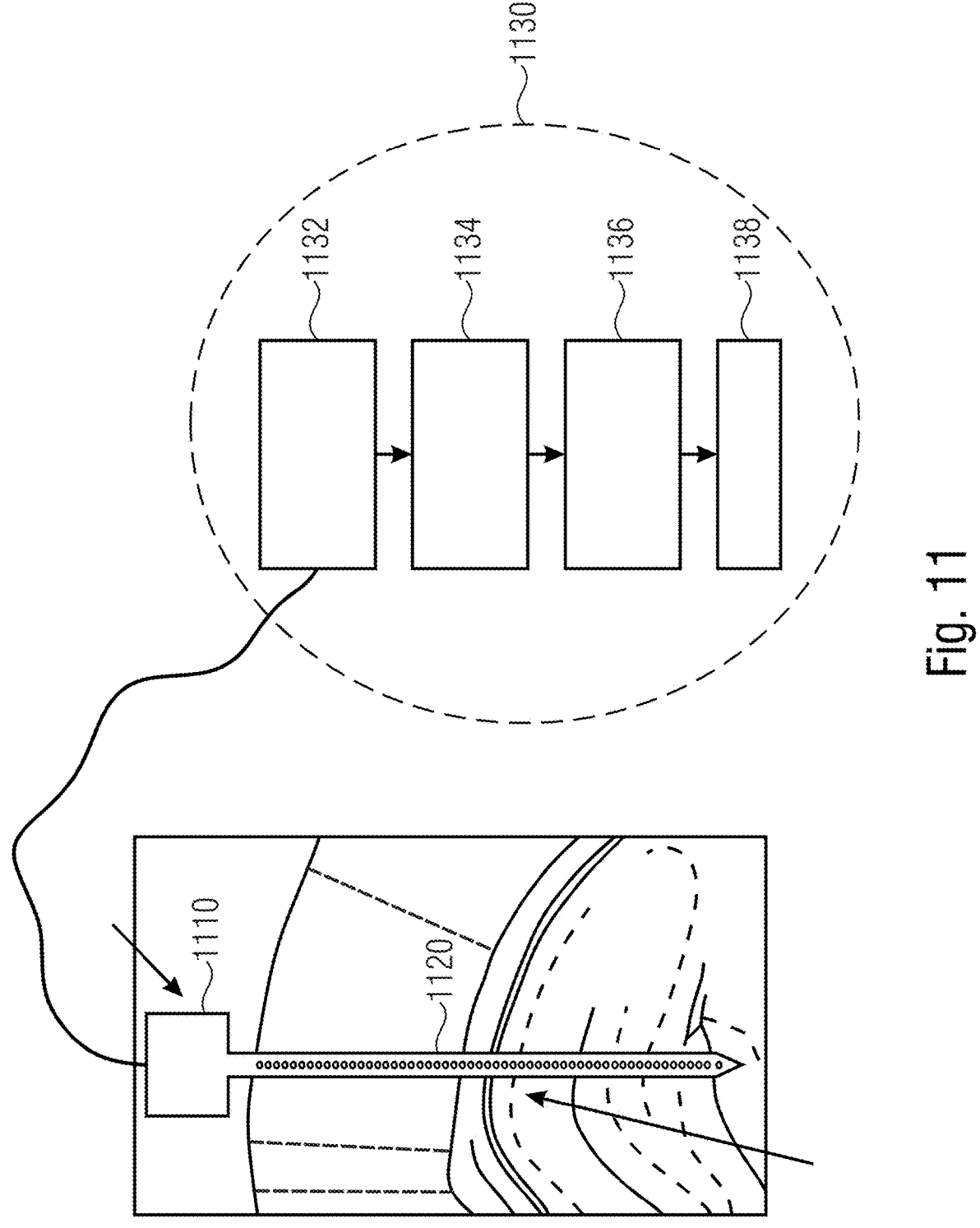
FIG. 11 shows a schematic view of a neuronal probe according to the prior art.

FIG. 11 shows a neuronal probe according to the state of the art with a base 1110, a shank 1120 and a signal process-ing unit 1130. The signal processing unit 1130 comprises a signal amplifier 1132, an analog-to-digital conversion 1134, a digital processing/interface 1136 and a computer 1138.

With the neuronal probe as described herein a number of components of the signal processing unit 1130 can be reduced by omitting the signal amplifier 1132 and the analog/digital conversion 1134. For example the neuronal probe already includes those components in each modular recording side. Accordingly, it can be seen that the neuronal probe according to the present invention clearly outperforms conventional solutions.

Figure 12:
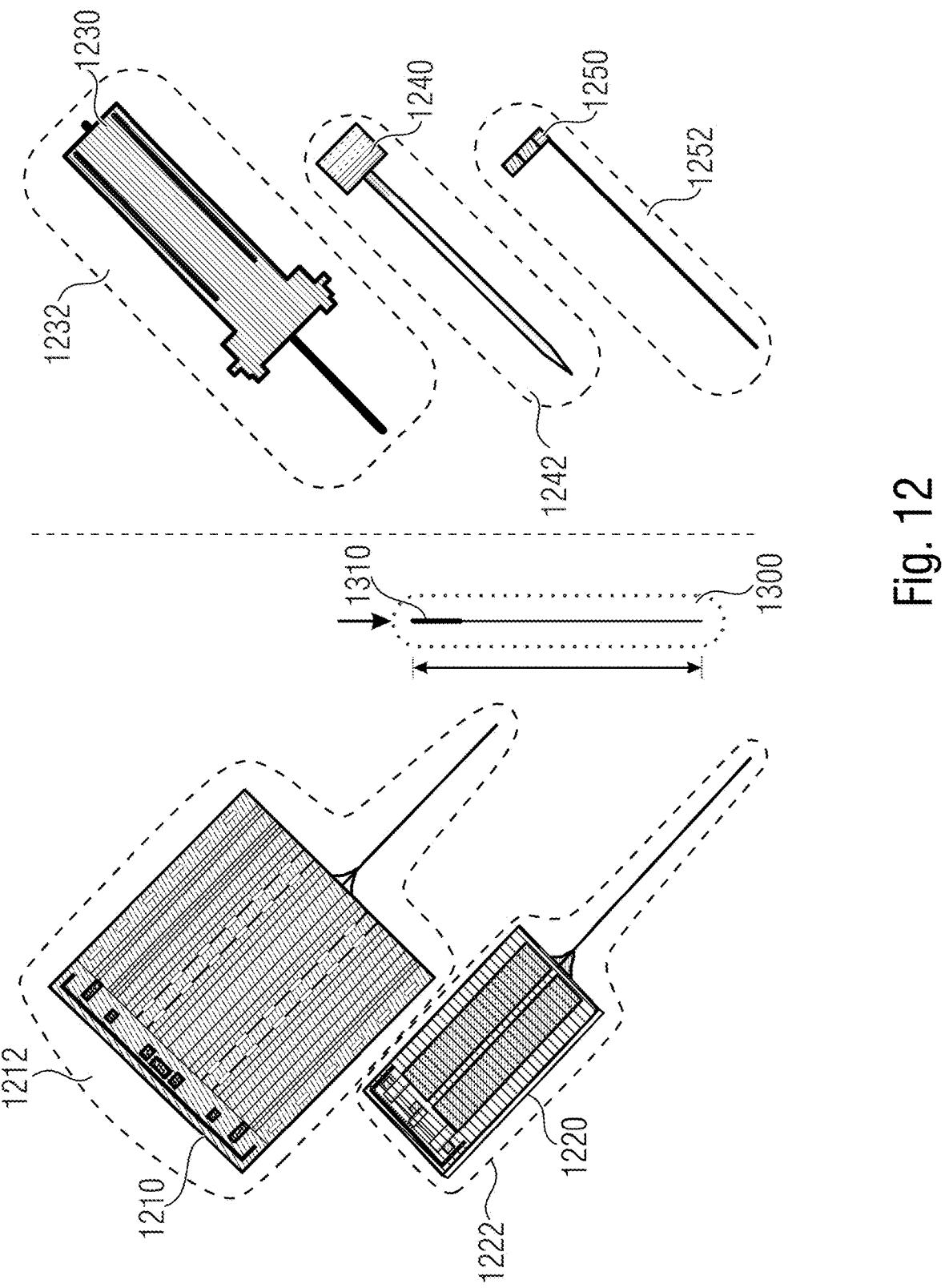
FIG. 12 shows a comparison of different neuronal probes including a neuronal probe according to an embodiment of the present invention.

FIG. 12 shows neuronal probes as stated in the art (neuronal probe 1212, 1222, 1232, 1242 and 1252) in comparison with a neuronal probe 1300 (an embodiment of the present invention), as presented in this application. It can be seen, that the neuronal probe 1300 as described herein comprises a very small base 1310. The base 1310 may be implemented much smaller than the base 1210, 1220, 1230, 1240 and 1250. Thus, the neuronal probe 1300 can be buried in tissue much easier and deeper than with the neuronal probes 1212, 1222, 1232, 1242 and 1252. Accordingly, it can be seen that the neuronal probe according to the present invention clearly outperforms conventional solutions.

Whilst some embodiments are described in connection with an analog-to-digital conversion using an integrator and a comparator or quantizer, in a specific example in connec-tion with the Gm-C based incremental delta-sigma analog-digital converter, i.e., a delta-sigma modulator of first order, embodiments described in the following further provide for an advantageous implementation of the analog-to-digital conversion by using a reconfigurable continuous-time incre-mental delta-sigma converter, i.e. an in-situ analog-to-digital converter 226 (see 226$_1$ to 226$_n$), that is configured for operating in a first operating mode 227a (see 227a$_1$ to 227a$_n$) for a coarse quantization and in a second operating mode 227b (see 227b$_1$ to 227b$_n$) for a fine quantization, i.e., for quantizing a remaining error 225 (see 225$_1$ to 225$_n$) of the first operating mode 227a, e.g., see FIG. 13.

The first operating mode 227a and the second operating mode 227b may differ from each other, e.g., in view of the amplification factor implemented in a feedback of the delta-sigma converter, in view of a sampling rate used and/or in view of a signal shape or signal type used for a feedback digital-to-analog converter 226.

A sensor array described in the following might comprise features and or functionalities as described with regard to one of the embodiments described above. Those embodiments may be combined without limitation with the embodiments described above, e.g., to substitute the prior ADC elements or to modify the analog-to-digital conversion. However, the advantage of reusing elements of a delta-sigma modulator in different operating modes 227 (see 227$a$ and 227$b$) to quantize a single analog signal 132 (see 132$_1$ to 132$_n$), the results of the different operating modes 227 to be combined with each other to obtain a combined result for the analog signal 132 is not limited to neural probes or even probes but may be used in any other application using an analog-to-digital conversion, e.g., sensor applications, communication applications or the like.

Figure 13:
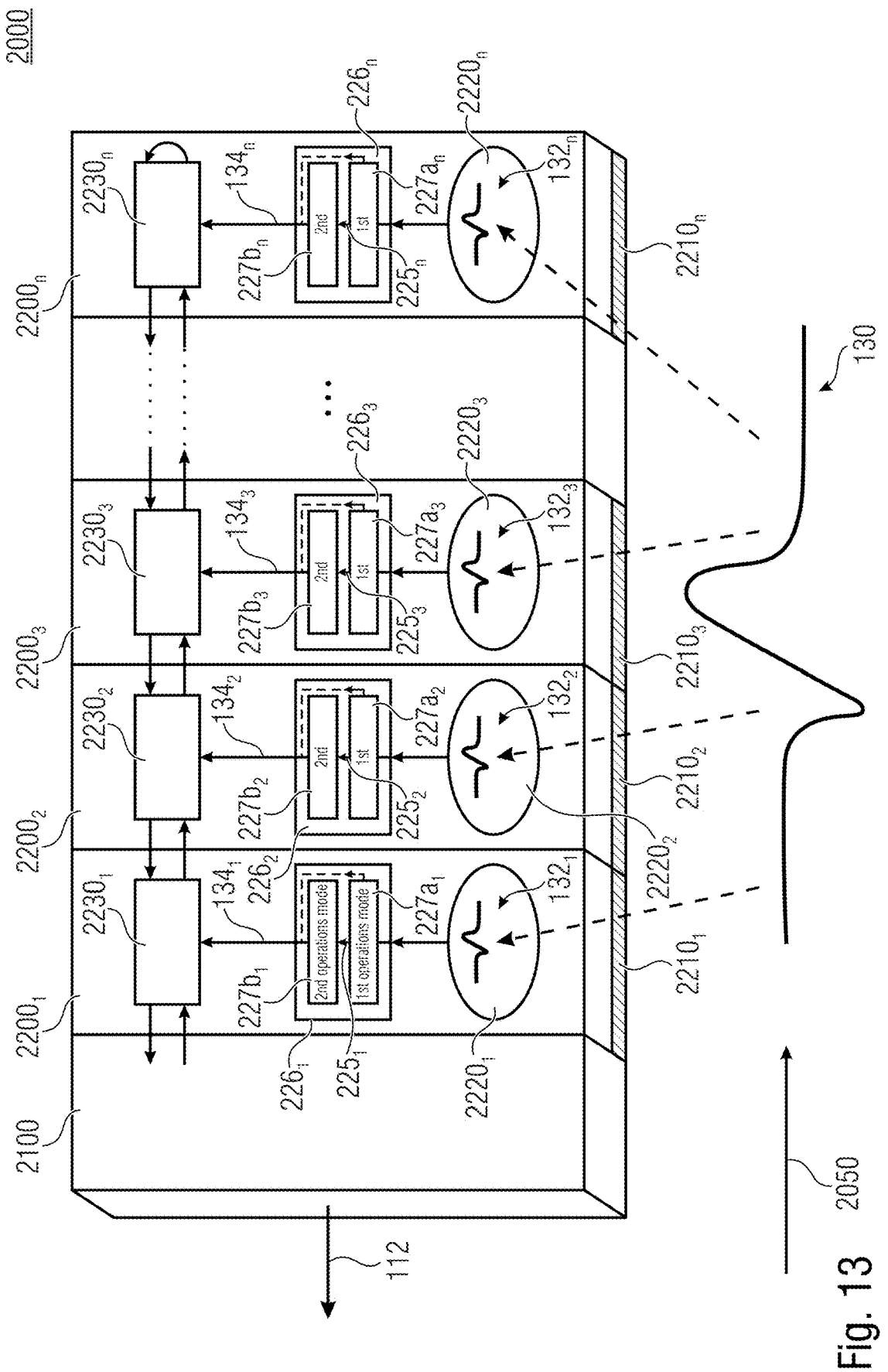
FIG. 13 shows an embodiment of a sensor array with two-step in-situ analog-to-digital converters.

FIG. 13 shows an embodiment of a sensor array 2000 comprising a base 2100 and a plurality of modular recording sites 2200 (see 2200$_1$ to 2200$_n$). The base 2100 and the plurality of modular recording sites 2200 are arranged along a first direction 2050 next to each other, wherein the base 2100 might represent the first element followed by the plurality of modular recording sites 2200. The aligned elements, e.g. the base 2100 and the plurality of modular recording sites 2200, are connect to each other to form the sensor array 2000.

Each modular recording site 2200 of the plurality of modular recording sites 2200 comprises, a CMOS substrate 2210 (see 2210$_1$ to 2210$_n$), at least one sensor element 2220 (see 2220$_1$ to 2220$_n$), an in-situ analog-to-digital converter 226, and a communication interface 2230 (see 2230$_1$ to 2230$_n$).

The electrical components of a modular recording site 2200, like the in-situ analog-to-digital converter 226 and the communication interface 2230, might be integrated in the CMOS substrate 2210 and might be positioned under a surface of the at least one sensor element 2220. A housing into which the surface of the at least one sensor element 2220 might be integrated can shield the electronic components from external influences.

The at least one sensor element 2220 is configured for receiving, e.g. detecting, an analog signal 132. For example, in the surroundings of the sensor array 2000 a biosignal 130 might occur, which can be detected by at least one of the pluralities of modular recording sites 2200. A sensor element 2220 of a modular recording site 2200 might detect the biosignal 130 as an analog signal 132, wherein the analog signal 132 represents the biosignal 130 at the position of the respective modular recording site 2200, e.g. with the same characteristics but with a damped amplitude due to a propagation loss. The respective at least one sensor element 2220 might be configured to forward the analog signal 132 directly to the in-situ analog-to-digital converter 226 or to a pre-processing means configured for providing a processed analog signal to the in-situ analog-to-digital converter 226.

The respective in-situ analog-to-digital converter 226 is configured for converting the analog signal 132 into a digital sensor signal 134 (see 134$_1$ to 134$_n$). Each in-situ analog-to-digital converter 226 is configured for operating in the first operating mode 227$a$ for performing a first quantization of the respective analog signal 132 using a first quantization setting and to obtain a residual error 225 from the first quantization; and for operating in a second operating mode 227$b$ for performing a second quantization of the residual error 225 using a second, different quantization setting for a same element of the respective in-situ analog-to-digital converter 226. The in-situ analog-to-digital converter 226 might be configured to provide the digital sensor signal 134 to further processing means or directly to the communication interface 2230.

The communication interface 2230 is configured to provide the digital sensor signal 134 or a further processed digital sensor signal to the base 2100. The communication interfaces 2230 of the plurality of modular recording sites 2200 are connected serially with respect to each other and to the base 2100.

The base 2100 is configured to provide a probe signal 112. The probe signal 112 might correspond to the digital sensor signal 134 provided by the communication interface 2230. Alternatively, the base 2100 might be configured to determine the probe signal 112 based on the digital sensor signal 134 provided by the communication interface 2230.

The sensor array 2000 might comprise features and/or functionalities which are described in the following with regard to FIGS. 14 to 35. The sensor array 2000 might, for example, especially further comprise a data compression unit 4000 and optionally a reduction element 4200, as will be described in more detail with regard to FIGS. 27 to 35.

Embodiments provide for a small, e.g., having an area of 0.00378 mm$^2$, scalable neural recording front-end for fully-immersible neural probes based on a two-step incremental delta-sigma converter 226 with extended counting and hardware reuse.

Embodiments relate, thus, to a delta-sigma modulator which is incorporated into a neuronal probe according to some embodiments. For example, such a delta-sigma modulator may be included in a modular recording site 2200 or at a different location, e.g., the base 2100.

According to further embodiments, the analog-to-digital converter 226 may be used without a neuronal probe.

A neuronal probe may be implemented such at that one, or more than one or every analog-to-digital converter 226, e.g., at each modular recording site 2200, the in-situ analog-to-digital converter 226 is configured for operating in a first operating mode 227$a$ for performing a first quantization of the biosignal, i.e. the analog signal 132, using a first quantization setting and to obtain a residual error 225 from the first quantization; and for operating in a second operating mode 227$b$ for performing a second quantization of the residual error 225 using a second, different quantization setting for a same element of the analog-to-digital converter 226. Thus, for the analog-to-digital conversion, an element, like an amplification element and/or a sampling element, can be used in both operating modes 227 by applying different settings dependent on the mode. This results in a small area needed for all components of the analog-to-digital converter 226, since an element, two or more elements or all elements used in the first operating mode 227$a$ can be reused in the second operating mode 227$b$.

According to an embodiment, the quantization setting corresponds to an amplification or a gain applied at the analog-to-digital conversion. An example for a first amplification or gain may be 1, less than one or more than 1. An example for an amplification, gain respectively of the second quantization setting may be a different value, e.g., a lower value such as 1/16, 1/8 or 1/4 with regard to 1 or the amplification value of the first quantization setting.

According to an embodiment, the quantization setting corresponds to a sampling rate applied at the analog-to-digital conversion. An example for a first sampling rate of the first quantization setting may comprise a normalized value of 1 and/or an absolute value of 1 MHz or less, at least 1.5 MHz or at least 2 MHz such as 2.72 MHz or even more. An example second sampling rate of the second quantization setting may comprise a normalized value of at least 5, at least 8 or more with regard to the first sampling rate, e.g., 21.76 MHz which may be 8 times 2.72 MHz. For example, a second gain being ⅛ of the first gain may be selected in accordance with 8 times a sampling rate of the second setting with regard to the first setting, rendering 8 as a relationship value. Alternatively, a different relationship value may be selected or no relationship value may be selected.

According to an embodiment, the quantization setting corresponds to a signal shape applied for sampling at the analog-to-digital conversion. An example first signal of the first quantization setting may comprise a non-return-to-zero pulse shape feedback signal, whilst the second signal of the second quantization setting may comprise a return-to-zero feedback signal, e.g., having a duty cycle of 12.5% and, thus, corresponding to the relationship value.

According to an embodiment, the first quantization setting may comprise an amplification of 1, a sampling rate of 2.72 MHz; a signal shape as a non-return-to-zero pulse shape feedback signal; and the second quantization setting may comprise an amplification/gain of ⅛, a sampling rate of 21.76 MHz; a signal shape as a return-to-zero feedback signal with 12.5% duty cycle to control the element "digital-to-analog converter", DAC, of the analog-to-digital converter. Different values may be selected for one or more parameters.

Figure 14A:
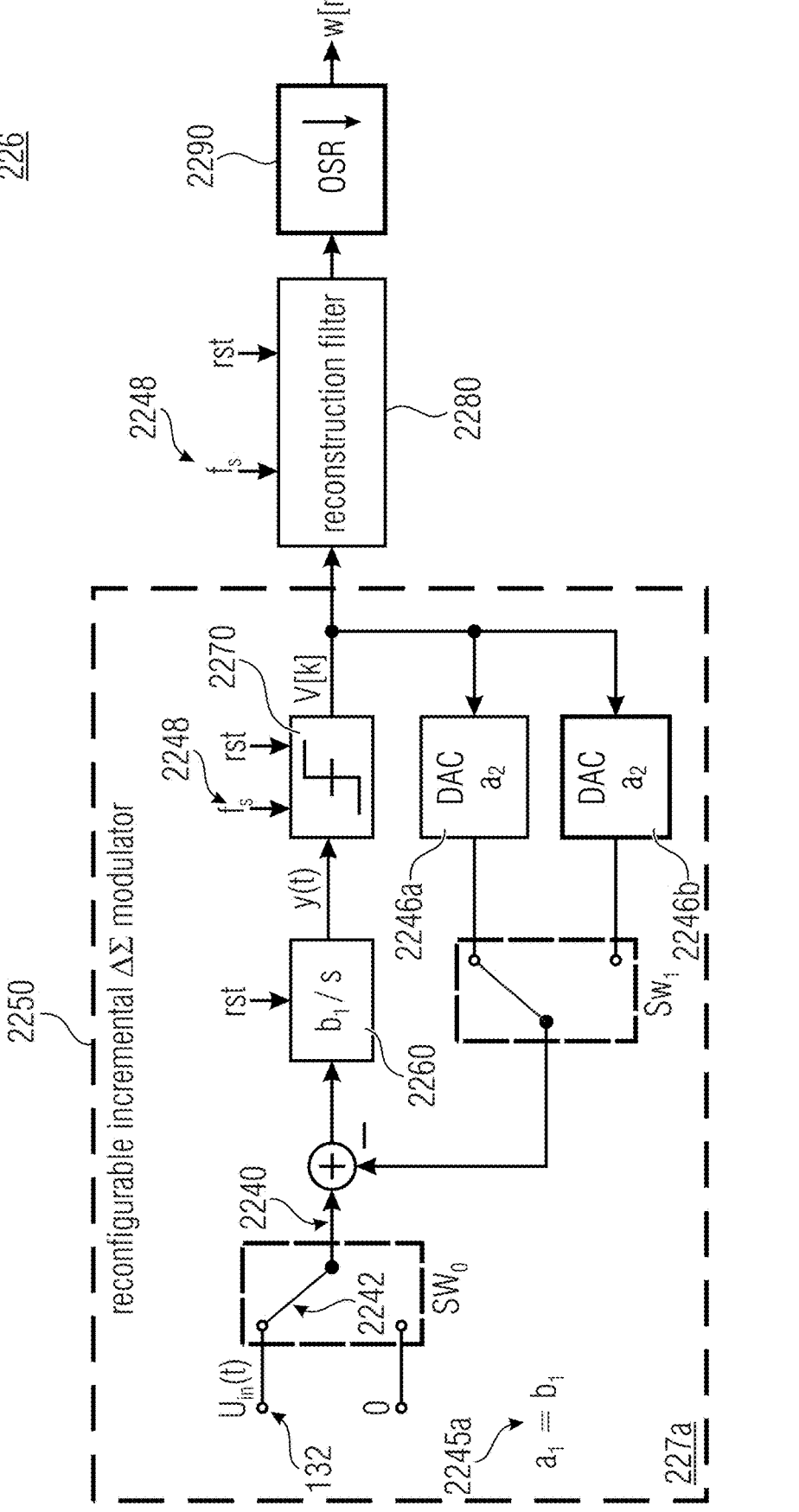
FIGS. 14a-c show an embodiment of two operating modes of an in-situ analog-to-digital converter.
Figure 14B:
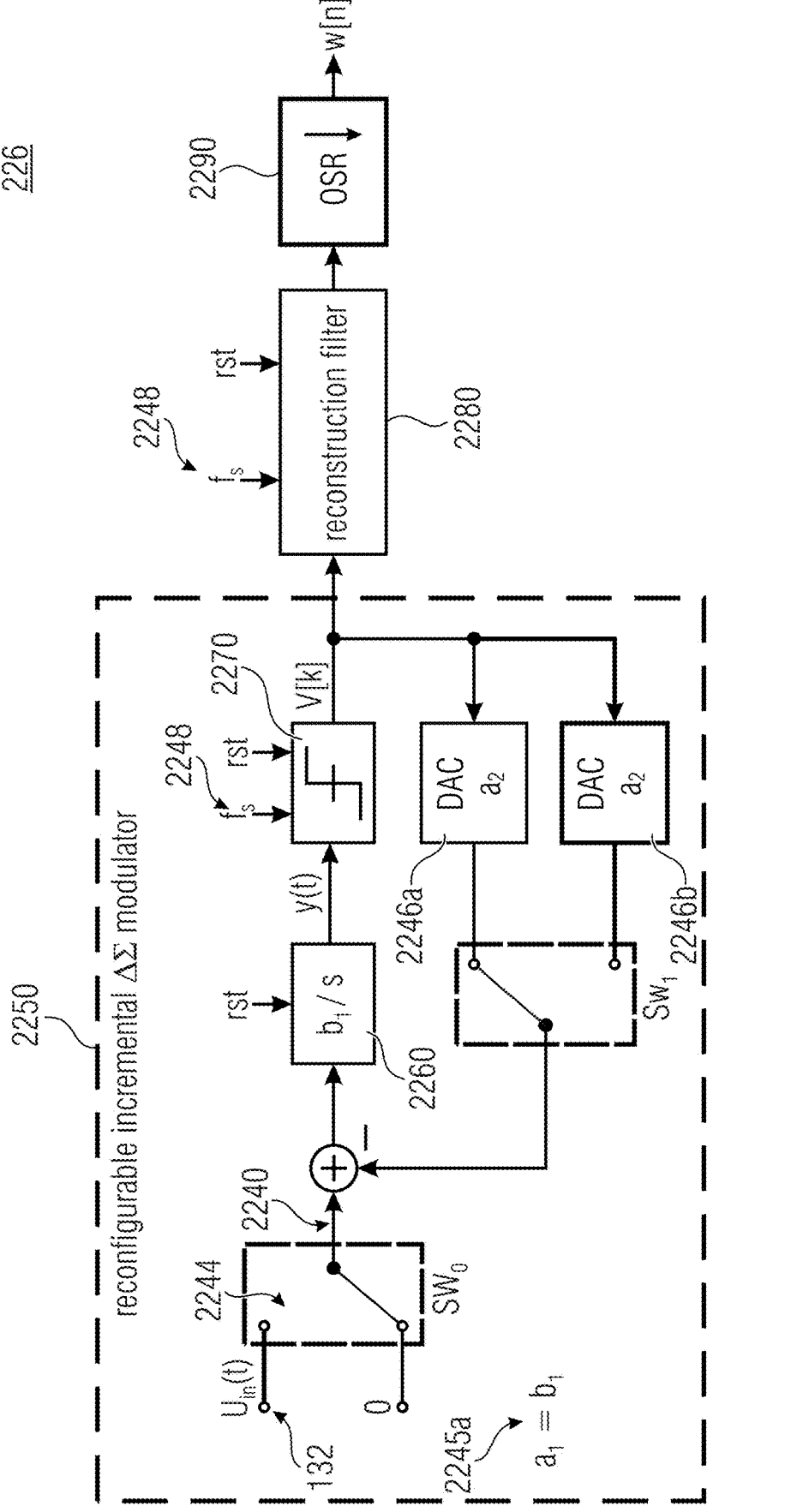
Figure 14C:
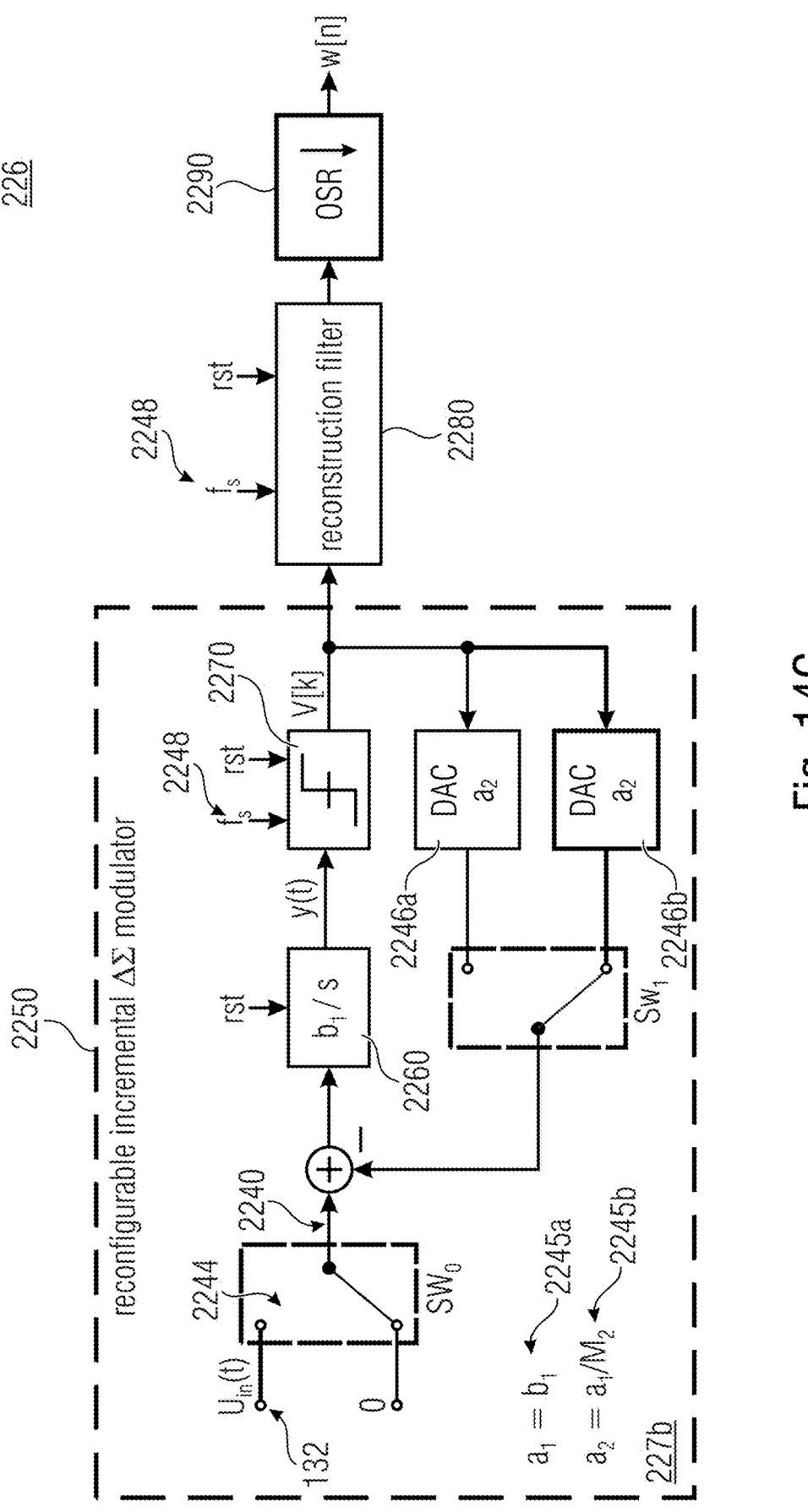

According to an embodiment, see e.g. FIGS. 14a to 14c, the sensor array 2000 may be implemented such that each or at least one of the in-situ analog-to-digital converter 226 comprises a signal input 2240 and is configured for providing a connection 2242 between the signal input 2240 and the analog signal 132, e.g. a biosignal, in the first operating mode 227a and for disconnecting 2244 the signal input 2240 from the analog signal 132, e.g. the biosignal, in the second operating mode 227b.

According to an embodiment the first operating mode 227a and the second operating mode 227b differ from each other, in view of an amplification 2245a/2245b applied in a feedback loop of a delta-sigma modulator 2250 of the analog-to-digital converter 226; a sampling rate 2248 of the delta-sigma modulator 2250; and/or of a pulse shape of the feedback DAC 2246a/2246b in the delta-sigma-modulator 2250.

For example, as pulse shapes of the feedback DAC 2246a/2246b non-return-to-zero and return-to-zero may be used in embodiments.

FIGS. 14a and 14b show an embodiment according to which the same DAC is used in both operating modes 227a and 227b. Assuming a non-return-to-zero (NRZ) pulse shape in the first operating mode 227a, instead of adjusting the feedback gain in the second operating mode 227b while using a NRZ DAC, the shape of the feedback signal may be changed, so that the DAC 2246a can be used for both operating modes 227a and 227b without reconfiguration and thus silicon area can be saved. For this purpose, a return-to-zero pulse shape may be used in the second operating mode 227b where the pulse width depends on the number of clock cycles in the second operating mode $M_2$ 227b. Another option is to increase the sampling frequency 2248 in the second operating mode 227b, which allows the same DAC 2246a to be reused for both operating modes 227a and 227b without reconfiguration and thus to save silicon area.

Assuming an amplification 2245a of 1 in the feedback path of the two-step incremental delta-sigma converter, i.e. the in-situ analog-to-digital converter 226, with $M_2$=8 as well as an sampling frequency 2248 of 2.72 MHz and a non-return-to-zero feedback signal in the first operating mode 227a, the amplification 2245b is reduced by the factor $M_2$, i.e., the amplification 2245b is ⅛, for fine quantization in the second operating mode 227b or the sampling frequency 2248 is increased by the factor of $M_2$, i.e., the sampling frequency 2248 is 21.76 MHz, or a return-to-zero signal with a duty cycle of 100%/$M_2$ is used, i.e., the duty cycle is 12.5%, or a combination of the mentioned methods, e.g., the amplification 2245b in the second phase, i.e. in the second operating mode 227b, is ¼ and the sampling frequency 2248 is 5.44 MHz or the amplification 2245b is ¼ and the duty cycle of the return-to-zero feedback signal is 50%.

According to an embodiment, in the second operating mode 227b an integrator 2260 and/or a quantizer 2270 and/or a feedback DAC 2246 of a delta-sigma modulator 2250 of an analog-to-digital converter 226 is reused with respect to the first operating mode 227a. In case of reusing the feedback DAC 2246a, as shown in FIGS. 14a and 14b, the feedback DAC 2246b can be omitted reducing the needed silicon area for the in-situ analog-to-digital converter 226.

In other words:

Embodiments provide for an analog front-end for recording neural signals based on a multi-step continuous-time incremental delta-sigma analog-to-digital converter.

Figure 15:
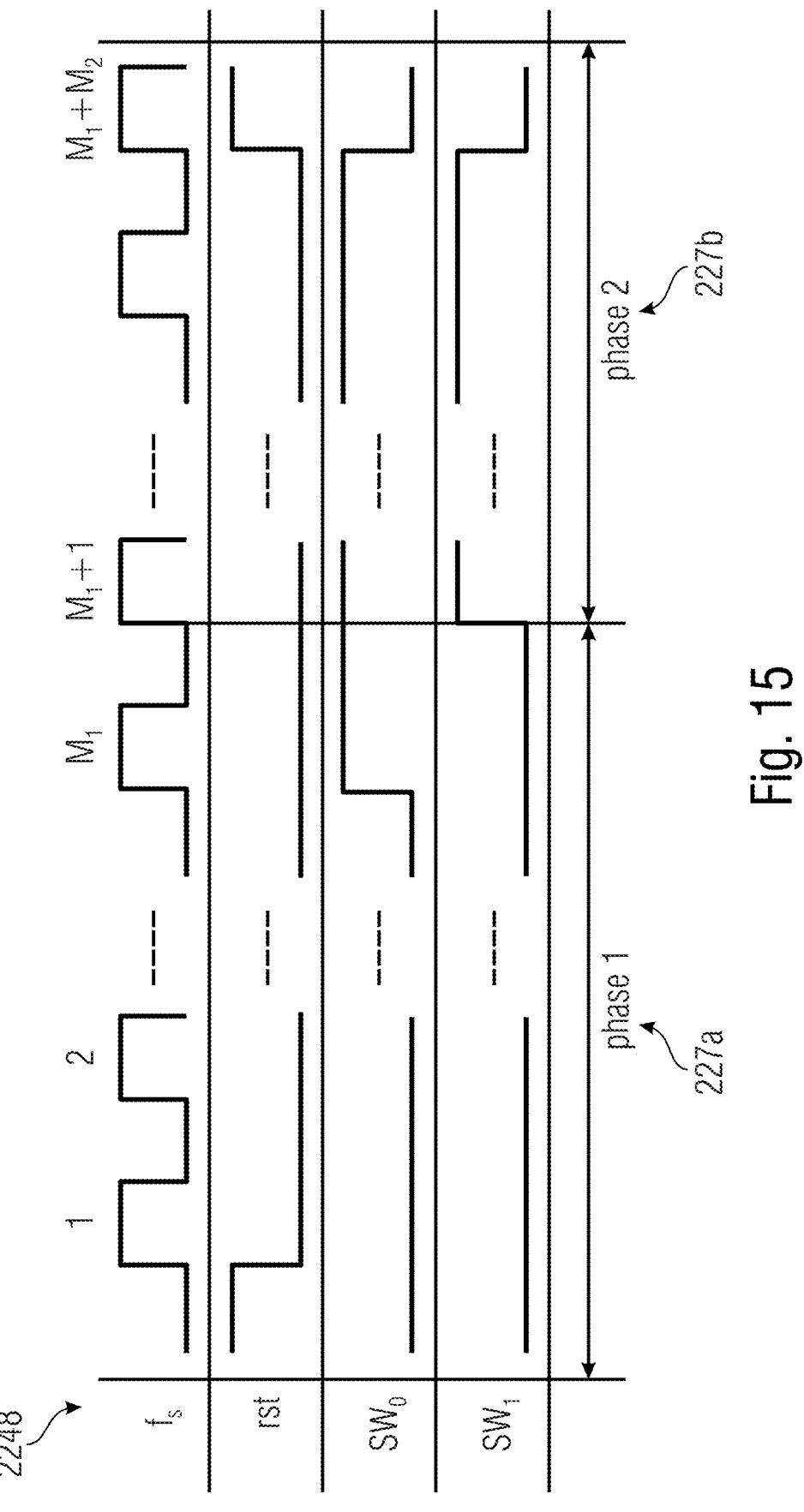
FIG. 15 shows a timing diagram of control signals for an in-situ analog-to-digital converter.

The architecture of the analog front-end is based on a multi-step continuous-time $I\Delta\Sigma$ ADC, i.e. the in-situ analog-to-digital converter 226, that combines the advantages of first-order and higher-order $\Delta\Sigma$ systems. This means that, compared to a conventional first-order system, the oversampling ratio can be reduced by using a multi-step method with coarse and fine quantization. At the same time, the area can be maintained since it is sufficient for the system to use one integrator 2260 that can be reused for the different stages, i.e. for the first operating mode 227a and for the second operating mode 227b, of the quantization process. The system architecture of the continuous-time ADC is shown for the different phases, i.e. for the first operating mode 227a and the second operating mode 227b, of the quantization process in FIG. 14, whereas FIG. 15 shows the timing diagram of the control signals. Here, $M_1$ and $M_2$ correspond to the number of clock cycles during coarse and fine quantization, respectively. The system, e.g. the sensor array 2000, might be composed of a configurable $I\Delta\Sigma$ modulator 2250 and a decimation filter 2290. For the process of the coarse quantization, the modulator 2250 is configured as a conventional $\Delta\Sigma$ modulator in phase 1 227a (see FIG. 14a). An input feedforward path is omitted so as to minimize the number of signal paths. Through this, however, not only the quantization error is stored in the integrator 2260, but also the input signal 132.

To ensure that only the remaining quantization error from phase 1 227a remains in the integrator at the beginning of phase 2 227b, the input signal $u_{in}(t)$ 132 is disconnected 2244 in the last clock cycle of phase 1 227a (see FIG. 14b). In phase 2 227b, the $\Delta\Sigma$ modulator 2250 is configured such that the gain 2245 in the feedback path is reduced according to the factor $M_2$ (see FIG. 14c). Instead of reducing the gain 2245, the sampling rate 2248 can be increased, the waveform can be changed, or a combination of methods can be used. The integrator 2260 and comparator 2270 are reused for the fine quantization.

FIG. 14 shows a system-level design of the multi-step continuous-time incremental delta-sigma analog-to-digital converter 226: (a) In phase 1 227a, the reconfigurable $\Delta\Sigma$ modulator 2250 is connected 2242 as a conventional $\Delta\Sigma$ modulator 2250. (b) In the last clock cycle of phase 1 227*a*, the input signal 132 is disconnected 2244 so as to ensure that only the quantization error, e.g. a residual quantization error, remains in the integrator 2260 for phase 2 227*b*. (c) The gain 2245 in the feedback path is adapted for the fine quantization in phase 2 227*b*.

During this phase, i.e. the second operating mode 227*b*, the stored value in the integrator 2260 y(t) is integrated towards the center value of the ADC. In doing so, the number of 1s and 0s occurring at the output of the comparator 2270 is counted. The result is added to the result of the coarse quantization. Furthermore, the remainder of the fine quantization is evaluated in the last clock cycle of phase 2 227*b*, gaining one additional bit of resolution. To this end, the sign of the residual value y(t) is checked and the result is attached to the previous one. Subsequently, the modulator 2250 is reset, and a new analog-to-digital conversion can be started. The resolution of the system, i.e. the in-situ analog-to-digital converter 226, is given by the number of clock cycles in the respective phases 227*a* and 227*b* with $ENOB=\log_2(M_1)+\log_2(M_2)+1$.

Figure 36:
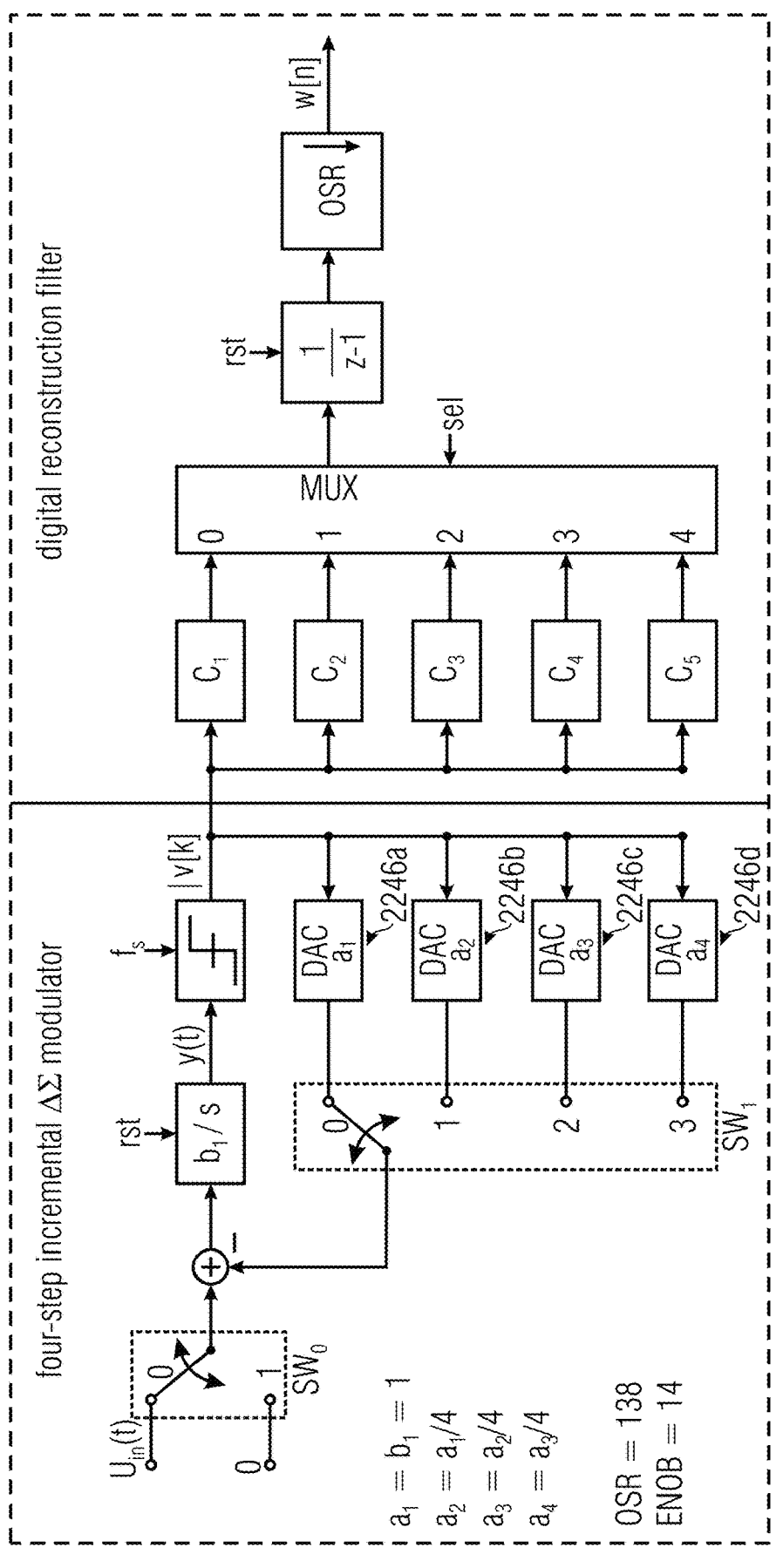
FIG. 36 shows an embodiment of a four-step analog-to-digital converter.

The two-step architecture in FIG. 14 can be extended to multiple steps, e.g., four steps, by e.g. including additional feedback paths, e.g., 2246*c* and 2246*d* in FIG. 36. The resolution of the system is then given as $ENOB=ENOB_{P1}+ENOB_{P2}+ENOB_{P3}+ENOB_{P4}+1$ with $OSR=M_1+M_2+M_3+M_4+2$ ($M_1$, $M_2$, $M_3$ and $M_4$ denote the number of clock cycles of the respective phase), depending on the number of steps. In case of four operating modes, the ADC 226 can be configured for operating additionally to the first operating mode 227*a* and the second operating mode 227*b* in a third operating mode and in a fourth operating mode, wherein the residual signal obtained by the first operating mode might represent a first residual signal and wherein the ADC is configured to obtain a second residual error from the second quantization. The ADC 226 can be configured for operating in the third operating mode for performing a third quantization of the second residual error using a third, different quantization setting of the analog-to-digital converter and to obtain a third residual error from the third quantization; and for operating in a fourth operating mode for performing a fourth quantization of the third residual error using a fourth, different quantization setting of the analog-to-digital converter. The first quantization might represent a coarse quantization and the quantization will get finer and finer with each operating mode so that the fourth quantization represents the finest quantization. At such a multiple-order ADC 226, the oversampling ratio can be further reduced compared to a two-step ADC 226, wherein at the same time, the area the area is not significantly increased since it is sufficient for the system to use one integrator and quantizer at all modes. Only additional Feedback paths may be added to enable the multiple operating modes.

Figure 16:
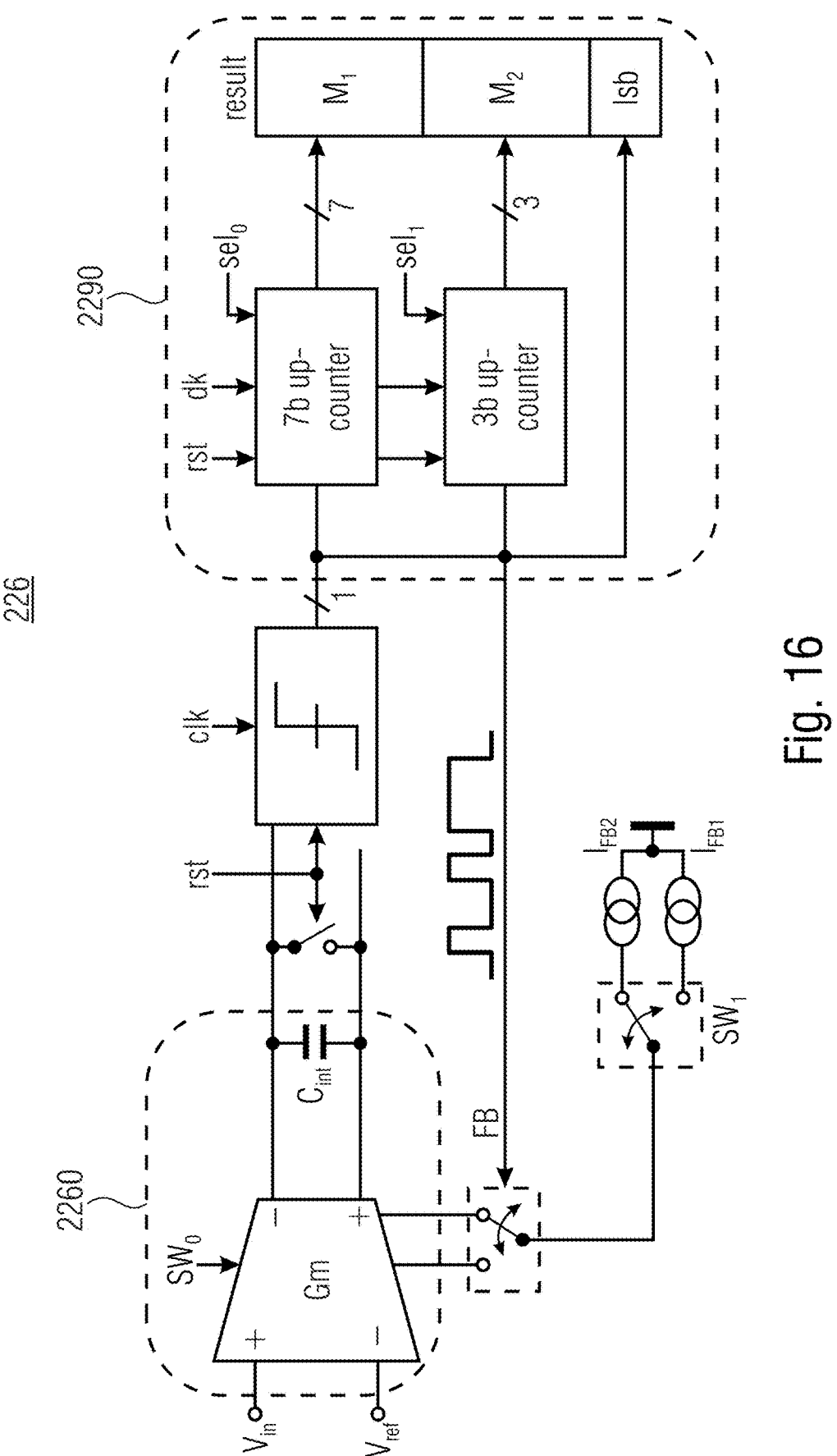
FIG. 16 shows a schematic view of an in-situ analog-to-digital converter.

The front-end architecture in FIG. 16 is based on a differential gm-C integrator 2260 for the smallest possible area at a resolution of 11 bit and an oversampling ratio of 136 ($M_1=128$, $M_2=8$). For the feedback, two current sources are used accordingly for phase 1 ($I_{FB1}$), i.e. for the first operating mode 227*a*, and phase 2 ($I_{FB2}$), i.e. for the second operating mode 227*b*. The decimation filter 2290 is realized according to the number of cycles of the respective phase with one ripple-carry adder each.

FIG. 16 shows a front-end architecture of the two-step continuous-time IΔΣ ADC 226 based on a gm-C integrator 2260.

Figure 17:
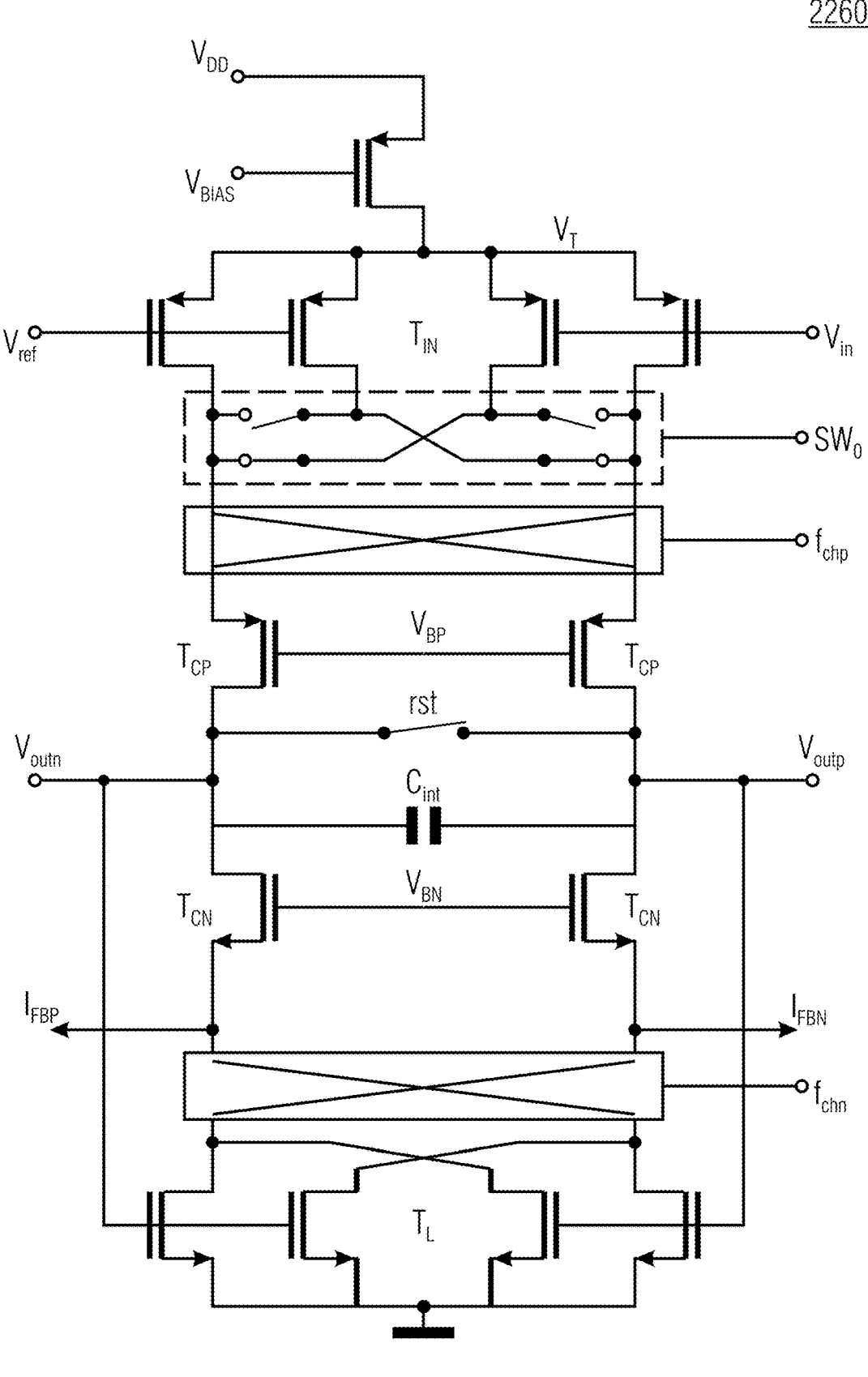
FIG. 17 shows a schematic of an integrator of an in-situ analog-to-digital converter.

The core of the transistor-level implementation is the gm-C integrator 2260 shown in FIG. 17. Instead of an additional amplifier for controlling the output common mode, the cross-coupled load transistors $T_L$ are used that are biased by the integrator output, thus saving area and power. Output common mode voltage is defined by $V_{GS}$ of the load transistors $T_L$. To minimize the noise of the circuit, or reduce the area of the load transistors, the "chopper" method is used in phase 1 227*a*. In order to disconnect the input signal 132 for phase 2 227*b*, the two input transistors TIN of the differential input pair are divided into two unit transistors each. One of the unit transistors, respectively, can be switched into the left or the right current path. By cross-coupling the input transistors in phase 2 227*b*, the differential output current is canceled. Since the offset in phase 2 227*b* can limit the resolution of the fine quantization, the "chopper" method is also applied to the input transistors and load transistors in this phase 227*b* so as to minimize the remaining offset.

With the multi-step quantization method, the oversampling ratio can be reduced by a factor of $(2M_1M_2)/(M_1+M_2)$ compared to a conventional first order IΔΣ system with the same resolution, leading to a strongly reduced power consumption on a similar silicon area due to the hardware reuse in the second operating mode 227*b*. This results in a greatly reduced power consumption, and since the integrator 2260 and the comparator 2270 are used for all phases 227*a* and 227*b*, the silicon area does not increase. Due to the reduced power, time-multiplexing methods can be employed without violating temperature requirements. With such a method, the area per channel could be further reduced. In contrast to discrete-time systems, the continuous-time implementation based on a gm-C integrator 2260 makes it possible to realize the system, e.g. the sensor array 2000, with a small integration capacitor on a smallest possible area and with low noise. Due to the intrinsic low-pass behavior of the ADC, an additional anti-aliasing filter becomes obsolete. Furthermore, cross-coupling the input transistors saves area by avoiding the need to add additional input transistors or a multiplexer in front of the input to disconnect 2244 the input signal 132. Additionally, it avoids the need to switch at the high-impedance input node Vin.

The herein proposed front-end architecture has the advantage that the area, the noise, and the power consumption could be strongly reduced compared to other concepts.

In again other words, a front-end having a possible size of 0.00378 mm² and, thus a scalable neural recording front-end for fully immersible neural probes based on a two-step incremental delta-sigma converter 226 with extended counting and hardware reuse is described.

The extensive integration of electronics into tissue-penetrating probes improves the signal quality and reduces parasitic effects for high-density recording of in vivo neural activity. In contrast to passive neural probes or devices implementing only part of the signal chain in the probe shank [5], [6], [11], fully immersible subcortical probes allow the recording of neural signals in deep brain regions [12]. This is achieved by directly digitizing brain activity in situ, thus avoiding a large base and allowing the probe to have a base and shank of equal width. However, this comes with a lower spatial resolution and an increased power density in the probe shank. To advance the concept of fully immersible probes, neural recording front-end architectures are required which reduce not only the area, but also the power per channel, thus avoiding tissue overheating due to increased power density. This paper presents a modular neural recording front-end, i.e. the sensor array 2000, which achieves these goals while also enhancing the noise and linearity performance compared to the state of the art.

Figure 18:
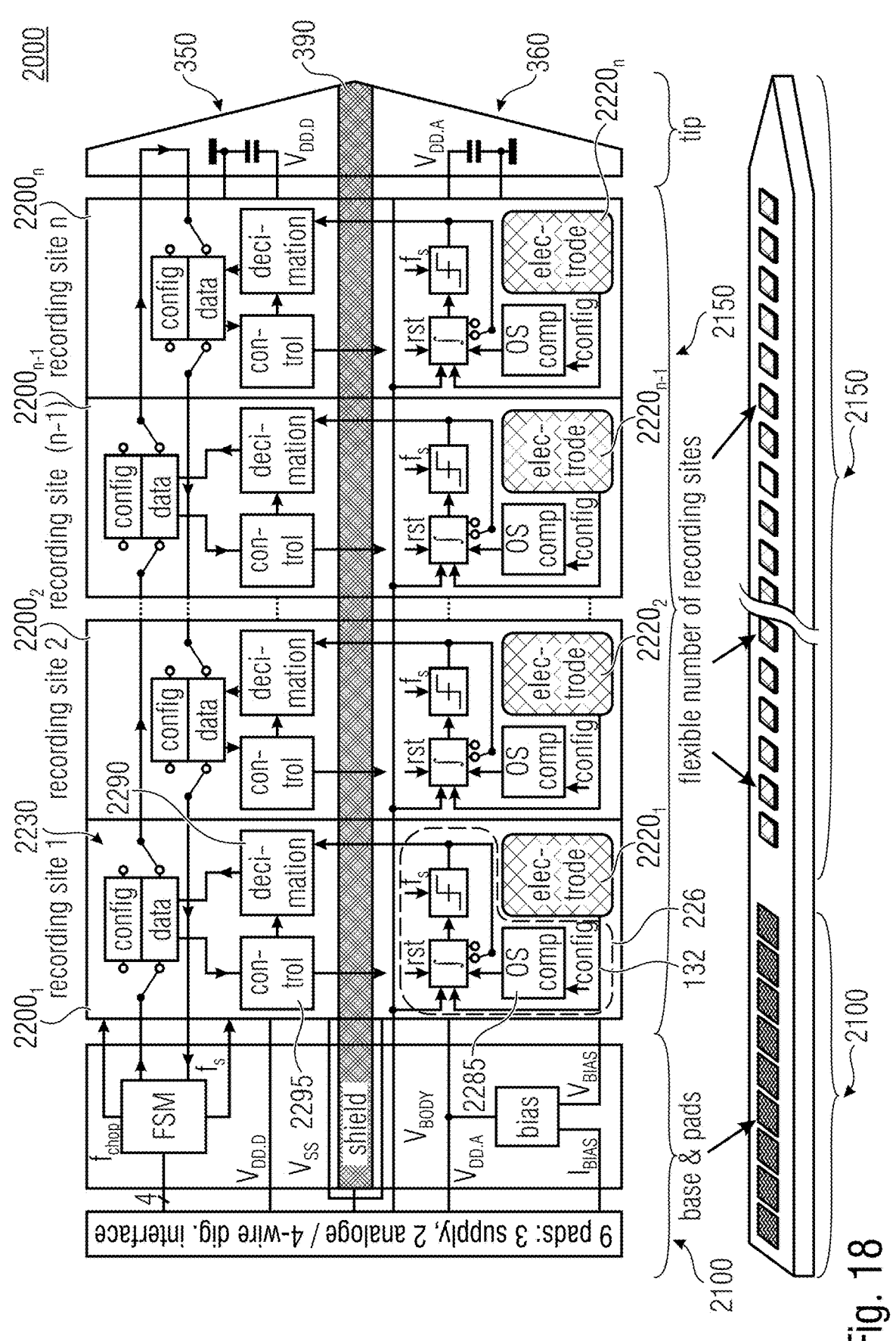
FIG. 18 shows schematically a system architecture of a sensor array with two-step in-situ analog-to-digital converters.

FIG. 18 shows the system architecture of a fully immersible probe 2000 with a variable number of cascaded modular recording sites 2200, where an 11 bit analog-to-digital converter 226, i.e. for an in-situ A/D conversion, with on-site electrode-offset compensation 2285 (os comp) is integrated underneath each electrode, i.e. the sensor element 2220. Each recording site 2200 features a continuous-time two-step incremental $\Delta\Sigma$ (I$\Delta$Z) ADC with an extended counting technique and hardware reuse, that is strictly divided into an analog 360 and a digital 350 part with a low-impedance shield 390 in-between. The digital domain 350 includes shift registers for configuration and readout of the digitized neural signals. Each recording site 2200 can comprise a communication interface 2230, a decimation filter 2290 and a control unit 2295 configured to generate control signals. The communication interface 2230, for example, comprises a data chain and a configuration chain. FIG. 18 shows a system-level design of the neural recording front-end integrated in a fully immersible neural probe 2000 with a flexible number of recording sites 2200 and an illustration of the probe 2000 with base 2100 and shank 2150 of equal width. The Base 2100 comprises a circuit with a finite-state machine controllable via a 4-wire interface (clock, control, data in and data out). Additionally, the circuit comprises a bias circuit with current mirror reference (external current source). Regardless of the number of channels, the base comprises only 9 pads.

Figure 19A:
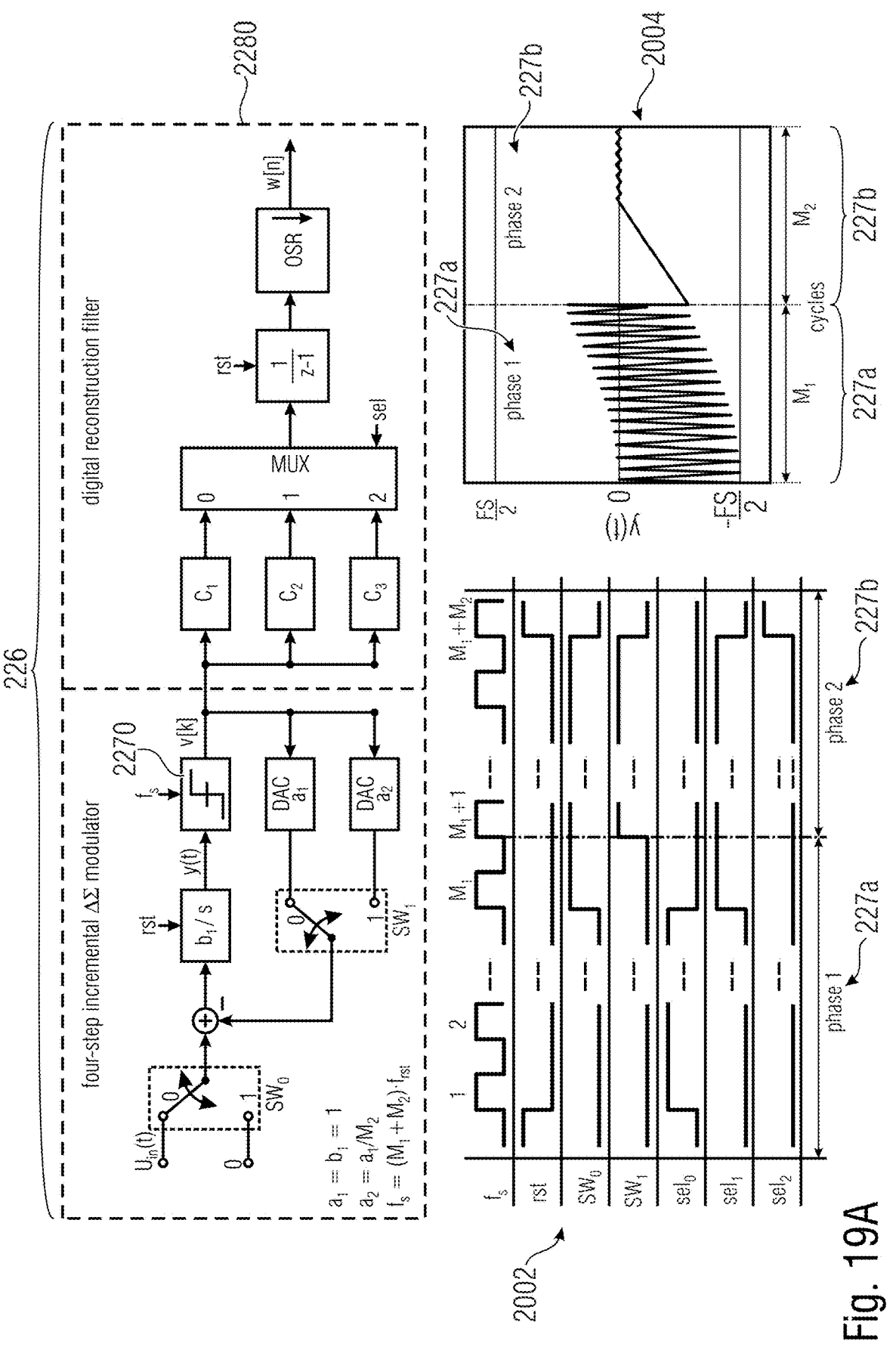
FIGS. 19a-e show an operation of a two-step in-situ analog-to-digital converter.

The operation of the two-step converter front-end shown in FIG. 19*a* is divided into two phases 227*a* and 227*b*, where $M_1$ and $M_2$ denote the respective duration in clock cycles, see also FIGS. 14 and 15 and the corresponding description for more details. FIG. 19*a* shows a block diagram of the two-step incremental $\Delta\Sigma$ ADC 226 with timing diagram 2002 and illustration 2004 of the quantizer 2270 input y(t) over the period of one conversion. The continuous time two step incremental $\Delta\Sigma$ converter has a low-pass transfer characteristics. OSR is reduced while maintaining area and the reconstruction filter 2280 is a simple up-counter. FIGS. 19*b* to 19*e* show the two operating modes 227*a* and 227*b* of the in-situ analog-to-digital converter 226 in more detail together with an illustration 2004 of the quantizer 2270 input y(t).

Figures 19B, 19C:
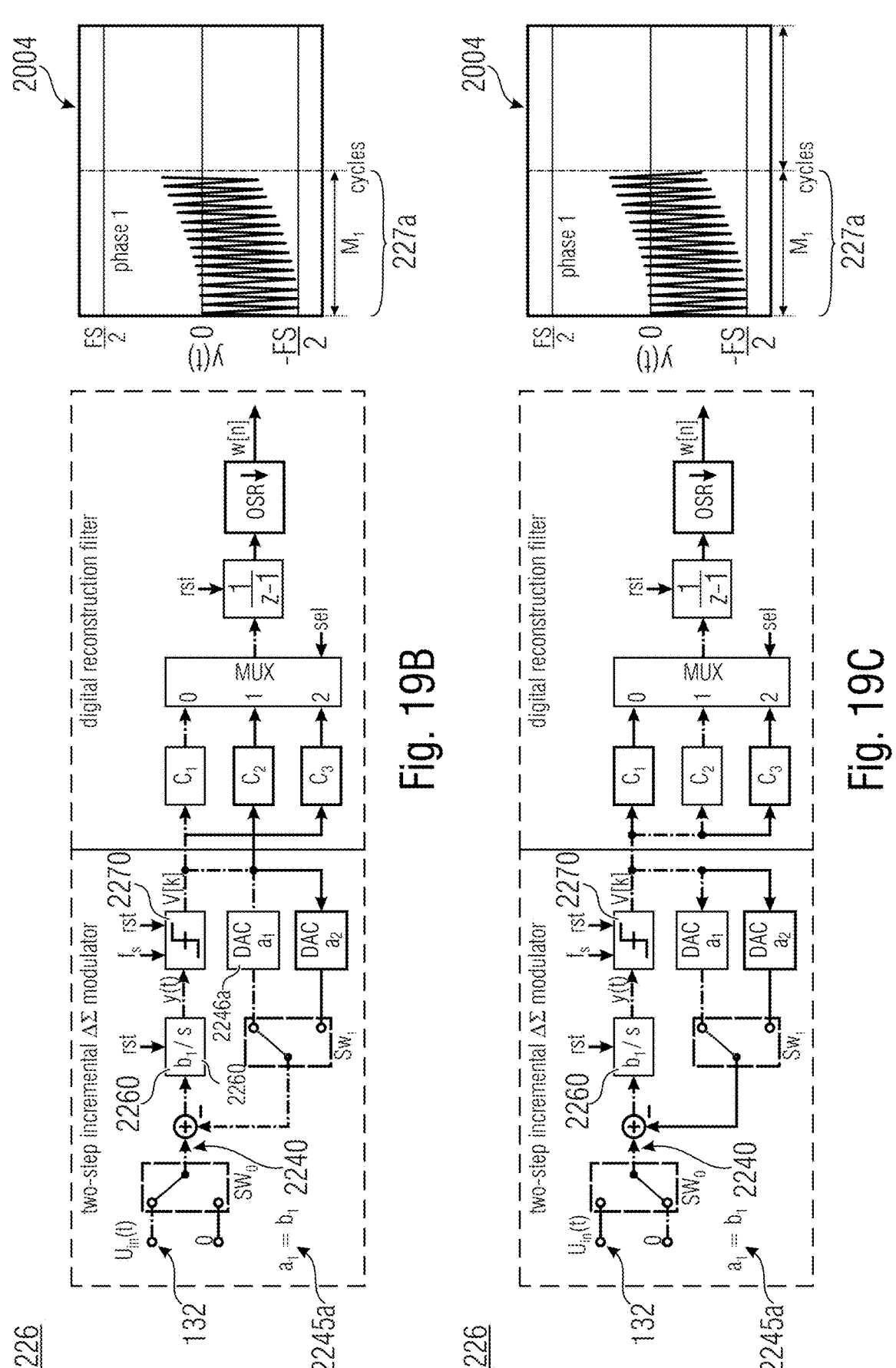

FIG. 19*b* shows an embodiment of the first operating mode 227*a*. The in-situ analog-to-digital converter 226 is configured as $\Delta\Sigma$ for coarse quantization. The resolution of the system is given by $ENOB_{P1}=\log_2(M_1)$, wherein $M_1$ is the number of cycles of the first operating mode 227*a*. The in-situ analog-to-digital converter 226 comprises no input feedforward to minimize signal paths. The quantization error and signal are stored in the integrator 2260.

FIG. 19*c* shows the last clock cycle of the first operating mode 227*a*. The input signal 132 is disconnected from the signal input 2240 of the in-situ analog-to-digital converter 226. Only the residual quantization error remains for the second operating mode 227*b*. The quantizer 2270 input y(t) can be determined as follows:

$$y(M_1)=b_1\int_0^{M_1-1}u_{in}(t)dt-a_1\int_1^{M_1}v(t)dt$$

Figures 19D, 19E:
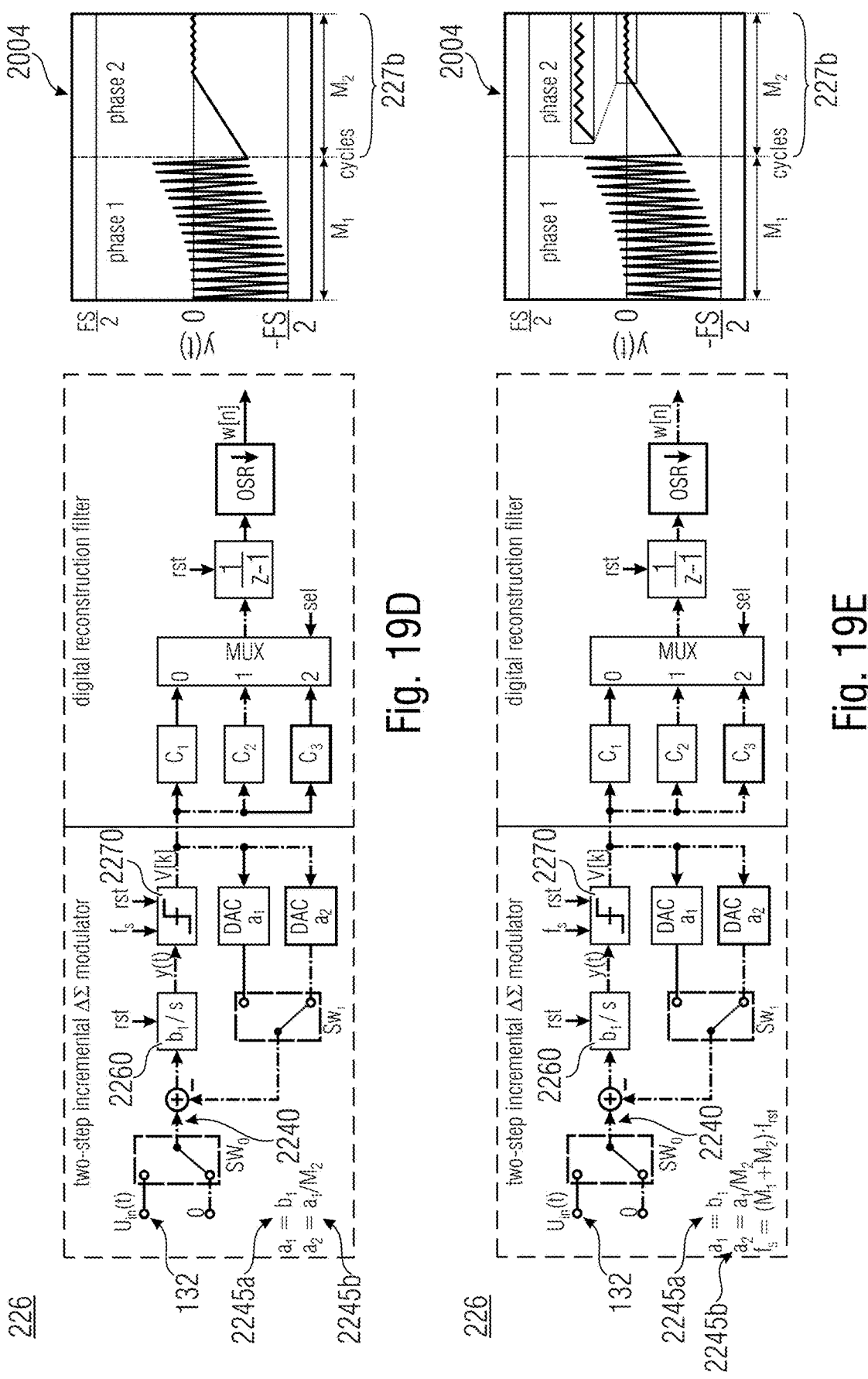

FIG. 19*d* shows an embodiment of the second operating mode 227*b*. The quantizer 2270 input y(t) is evaluated by integrating towards zero. The integrator 2260 and the comparator 2270 used in the first operating mode 227*a* are reused in the second operating mode 227*b*. The feedback gain 2245*b* is reduced by the number of cycles $M_2$ of the second operating mode 227*b* compared to the feedback gain 2245*a* of the first operating mode 227*a*. The resolution of the system is given by $ENOB_{P2}=\log_2(M_2)$.

FIG. 19*e* shows the last clock cycle of the second operating mode 227*b*. In the last clock cycle of the second operating mode 227*b*, the residue of the second operating mode 227*b* is evaluated resulting in one additional bit of resolution by checking the sign of the quantizer 2270 input y(t). The resolution of the system is given by $ENOB=\log_2(M_1)+\log_2(M_2)+1$ with $OSR=M_1+M_2$. The OSR is reduced by $(2M_1M_2/M_1+M_2)$ compared to a first order I$\Delta\Sigma$ ADC.

FIG. 20*a* shows a transistor-level implementation of the incremental $\Delta\Sigma$ modulator 2250 with a reconfigurable minimal area Gm-C integrator 2260 with current feedback and an optional IDAC 2246 for electrode-offset compensation. The time constant is not critical as the quantizer gain is ill defined. The area is minimized by reducing the time constant, i.e., $C_{int}$. The two-step I$\Delta\Sigma$ ADC 226 in FIG. 20*a* is implemented with a Gm-C integrator 2260 and has an oversampling ratio of 136 ($M_1$=128, $M_2$=8). Thus, the OSR is reduced by a factor of about compared to a first-order I$\Delta\Sigma$ ADC. The output bitstream of the dynamic latch comparator with reset is fed into the reconstruction filter and used to control the feedback current source ($I_{FB1}$ or $I_{FB2}=I_{FB1}/M_2$), i.e. the NMOS feedback, draining current from the left or right branch of the integrator 2260. A dummy path is included to enhance the transient response when the feedback currents are switched between the conversion phases, i.e. between the operating modes 227*a* and 227*b*. Instead of using an additional CMFB amplifier, the cross-coupled load transistors $T_L$ are self-biased by the OTA output, thus saving area and power. Chopping the NMOS load transistors in phase 1 227*a* with a frequency $f_{chop}$=340 kHz ($f_{chop}$ represents $f_{chn}$) reduces flicker noise. Since $f_{chop}$ is a multiple of the I$\Delta\Sigma$ reset frequency $f_{rst}$=20 kHz, the spectral components caused by chopping are suppressed by the transfer characteristic of the converter and folded to DC, i.e. avoiding spectral components within the frequency bands of APs/LFPs. The frequency $f_{chop}$ is generated by a power of 2 integer division of $f_s$ in the base. To avoid switching at the high-impedance OTA inputs when disconnecting the input during the second conversion phase, each of the PMOS input transistors with Gm=21.7 μS is divided/split into two unit transistors $T_{IN}$, where one of each can be switched to the opposite current branch, i.e. one of each can be switched to the left and right branch. This avoids switching at the high-impedance input. By cross-coupling these unit transistors, the differential output current of the OTA is cancelled. The cascode transistors $T_{CN}$ and $T_{CP}$ are implemented to protect the high-impedance output. The Gm-C integrator 2260 might have noise critical input and load transistors. Moreover, the residual offset in phase 2 is minimized by chopping the current branches at the input and the OTA current source loads with the sample frequency $f_s$. The integrated offset in phase 2 should be $<<FS/(2M_2)$ to not limit the resolution of the fine conversion. The reconstruction filter 2280 consists of or comprises a 7b (bits) and a 3b ripple-carry adder whose results are merged together with the LSB resulting from the last conversion cycle. The 7b ripple-carry counter is used for the first operating mode 227*a* and the 3b ripple-carry counter is used for the second operating mode 227*b*. The 11b result is stored in a shift register that is cascaded to the result registers of adjacent ADCs, e.g. by the communication interface 2230. The in-situ analog-to-digital converter has a resolution of 11 bit. Each front-end includes 5 configuration bits for offset compensation and to turn the ADC on/off. Depending on the application and the electrode material [12], electrochemical offset variations between electrodes may occur that exceed the full-scale (FS) input range of the ADC. The FS ranges were defined based on in vivo measurements using dc-coupled fully immersible neural probes with untreated electrodes [12]. Thereby an FS of ±60 mV can reliably cover all electrochemical offsets between electrodes. However, it is expected that improvements in post-CMOS electrode deposition techniques will further reduce the local offset. Thus, two prototypes have been designed: a compact high-density recording site with a full scale (FS) of ±7 mV and an electrode pitch of 35 μm for applications with low local offset variations, and a more versatile front-end with an additional 4b IDAC 2246 that covers offsets up to ±60 mV and a pitch of 55 μm, see also FIG. 20b. Neural signal needs to be in the ADC full-scale range. Different prototype chips with 8, 12, and 24 electrodes have been fabricated and tested. Due to the system's modularity, the number of recording sites can be easily increased to electrode counts as in and above. However, in this specific prototype run the length of the probe was limited by the available CMOS reticle. The two-step IΔΣ ADC 226 might have a bandwidth of 10 kHz ($f_{rst}$=20 kHz, $f_s$=2.72 MHz).

The differential output current for the first operating mode 227a can be determined according to $I_{out}$=Gm$_{in}$·(V$_{electrode}$−V$_{BODY}$) and for the second operating mode 227b according to $I_{out}$≈0.

The IDAC 2246 for offset compensation in FIG. 20a, the os comp 2285 in FIG. 18 may be configured for compensating an offset in the analog signal 132, e.g., the biosignal. Such an offset compensation circuit may be arranged, for example, in each modular recording site 2200 but may also be arranged, at least in parts, in or at the base 2100 and/or a different location. The offset compensation circuit may be configured for compensating the offset such that the input signal 132 is adapted in view of a dc-offset so as to match a conversion full-scale window of the analog-to-digital converter 226. Thereby, an offset between adjacent sensors may be compensated which may occur, for example, in a body due to local variations, e.g., in a pH-value.

Figure 21A:
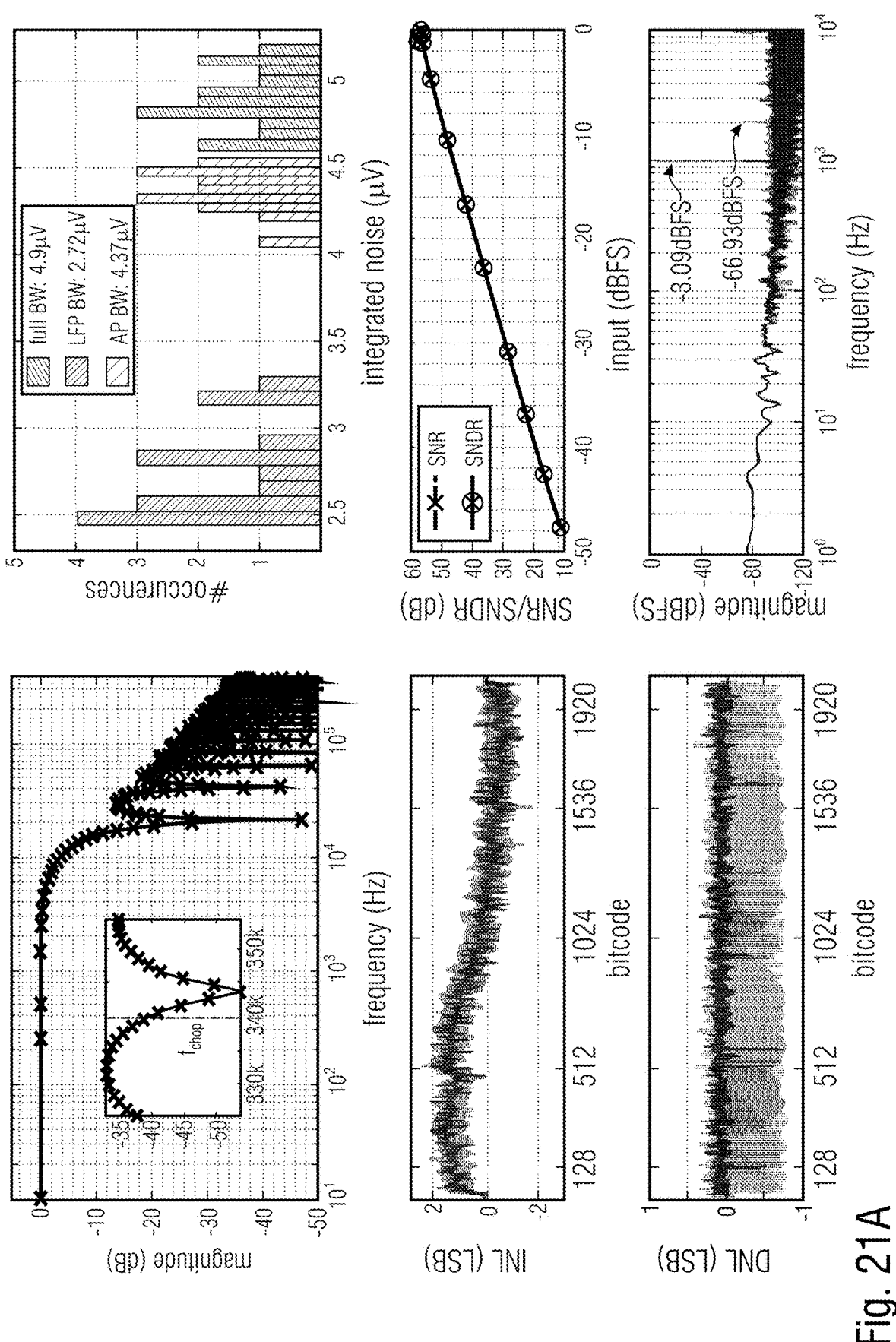

FIG. 21a shows the measured transfer characteristic after decimation together with the noise and the linearity performance of the ADC with offset compensation, i.e. the performance metrics of the two-step incremental ΔΣ ADC 226 with offset compensation, e.g. using an IDAC. Statistical noise distributions are measured across 16 recording sites 2200 (two 8-channel chips). The average integrated noise in the full bandwidth of 10 kHz results to 4.9 μVrms, while the average noise in the frequency band of local field potentials (LFP, and action potentials (AP, 0.3 Hz-10 kHz) amounts to 2.72 μVrms and 4.37 μVrms, respectively. Nonlinearity measurements show a DNL of −0.84/+0.44 LSB and an INL of −1.72/+2.55 LSB. A THD of 0.078% is measured for a 1 kHz input signal with an amplitude of 10 mVpp. Each ADC has a power consumption of 8.59 μW, of which 2.67 μW is taken by the digital circuits (decimation, controller and non-overlapping clock generators, e.g. two non-overlapping clock generators for NMOS and PMOS transistors). The digital data interface, e.g. the communication interface, and data transmission need an additional 6.35 μW per channel.

FIG. 21b shows the measured sinc-shaped transfer characteristic after decimation together with the noise for a sensor array 2000 comprising 12 recording sites 2200 without an IDAC for offset compensation. The power consumption per channel is 13.94 μW. It can be seen that chopping artifacts are reduced by approximately 40 dB.

FIG. 21c shows the measured noise for a sensor array 2000 comprising 8 recording sites 2200 with IDAC for offset compensation or increasing the dynamic range of the ADC.

The power consumption per channel is 14.94 μW. It can be seen that the peak of SNDR is around 57.5 dB.

Figure 22:
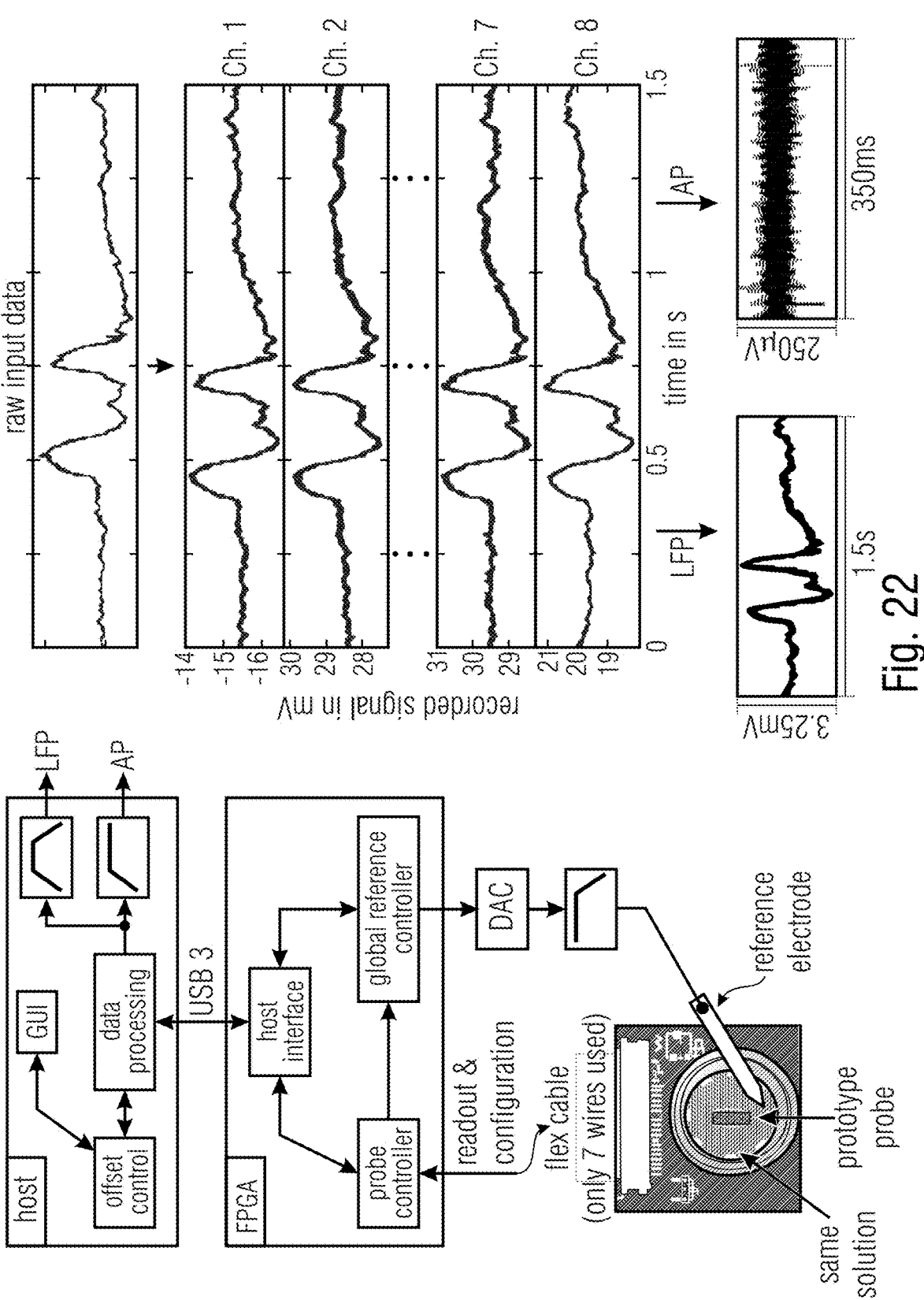
FIG. 22 shows an experimental setup of a measurement system with a sensor array comprising local offset compensation.

The functionality of the proposed system is validated in saline solution on an 8-channel prototype with offset compensation by the experimental setup shown in FIG. 22. Prerecorded neural signals were applied via an aluminum reference electrode to the saline solution, as well as the reference potential that was regulated by a global reference controller [12]. The prerecorded neural signals are measured with the prototype probe. Standard AlCu pads with a size of 11×11 μm$^2$ from the CMOS fabrication process served as recording electrodes, i.e. as the sensor elements. The recorded signals are separated in APs and LFPs by digital postprocessing. The diagrams show that the maximum amplitude of the LFPs of around 3 mV is covered well by the full scale of the ADC. However, as can be seen by the numbers on the y-axis, the actual values of the input signals to the ADC are spread over a wide range covering positive and negative voltages of a few 10 millivolts. Although channels 1 and 2 are adjacent they have a high difference in local electrochemical offsets, which are nevertheless locally compensated through the extension of the dynamic range of the ADC. This demonstrates the effectiveness of the local offset compensation in combination with the automatic control of the global reference. The signals recorded with this system are separated in APs and LFPs by digital post-processing.

Figure 24:
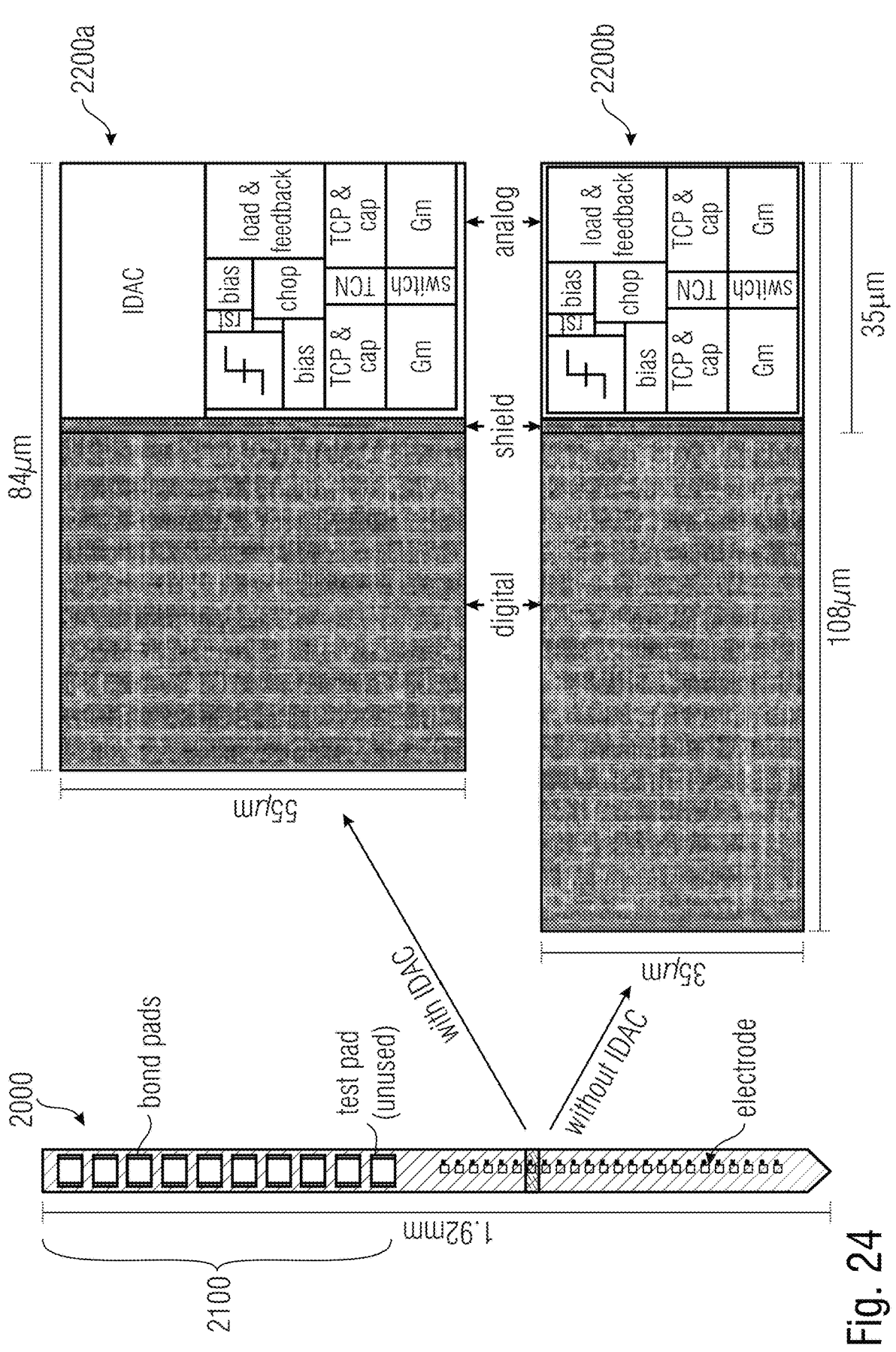
FIG. 24 shows a micrograph of a sensor array prototype together with the layouts of front-ends with and without electrode-offset compensation.

The presented modular neural recording front-ends are implemented in a 0.18 μm CMOS technology on an area of 0.00378 mm$^2$ without and 0.00462 mm$^2$ with offset compensation. This results in E-A Ch. FoMs [11] of 4.04 fJ/C·s·mm$^2$ and 5.97 fJ/C·s·mm$^2$ for SNDRs of 58.04 dB and 57 dB. Both versions are compared to the state-of-the-art neural probes in FIG. 23, showing that the presented architecture achieves a 2-3 times smaller power/channel on an up to 23% smaller silicon area compared to other fully integrated probe designs. The noise in the AP and LFP bands are reduced by 31-38% and 65-70%, respectively. A micrograph of a neural probe prototype is depicted in FIG. 24 together with the layouts of both front-ends with and without electrode-offset compensation. A unit cell, i.e. a modular recording site 2200, has approximately dimensions of 108×35 μm$^2$ without electrode-offset compensation and dimensions of 84×55 μm$^2$ with electrode-offset compensation. Since the integrated digital circuits occupy up to 67% of the total area, the presented designs would strongly benefit from technology and supply scaling. FIG. 24 shows a sensor array with a base 2100 comprising 10 bond pads, wherein only 9 are currently used.

Figure 25:
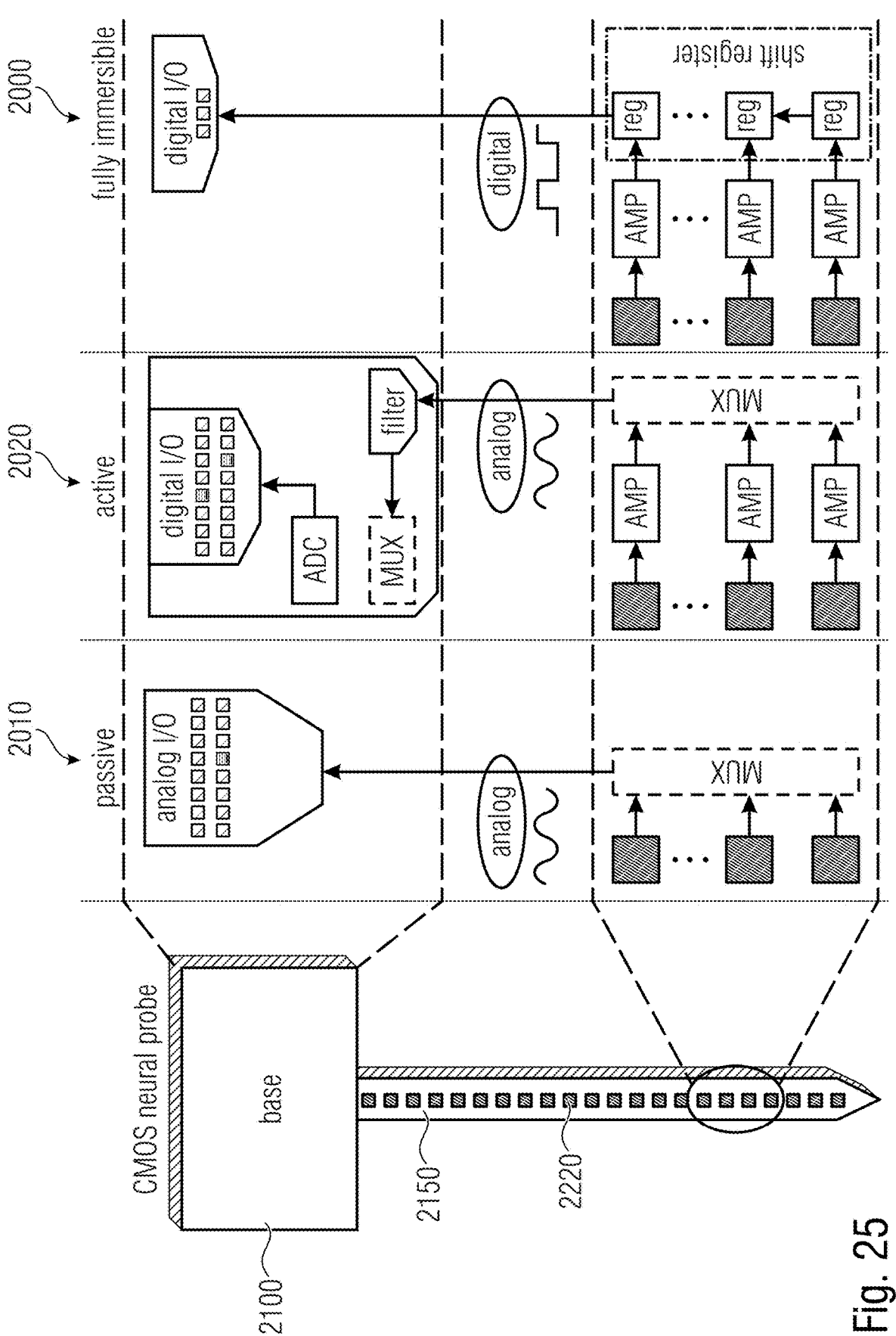
FIG. 25 shows different options for a signal conditioning integrable in a CMOS neural probe.

FIG. 25 shows schematically a CMOS neural probe with a base 2100 and a shank 2150 comprising a plurality of sensor elements 2220. Additionally, FIG. 25 shows different options for a signal conditioning integrable in a CMOS neural probe. Passive neural probes 2010 have no on-chip signal conditioning, a low number of parallel readout channels and a high spatial resolution (with multiplexing). EMI and crosstalk sensitive signals are routed in the shank 2150. Additionally, passive neural probes 2010 have a large base due to a high number of interconnections. Active neural probes 2020 have the complete signal conditioning on-chip, have a high spatial resolution and an increased number of parallel readout channels. Buffered signals, which are less sensitive to crosstalk and EMI, are routed in the shank 2150. Additionally, active neural probes 2020 have a large base due to integrated electronics. The herein proposed fully immersible neural probe 2000 has a minimized signal conditioning chain, an in-situ A/D conversion, a small base, independent on the number of recording sites, and a full parallel readout. No sensitive signals are routed in the shank 2150. However, the spatial resolution is challenging. Especially advantageous is a reduced silicon area/electrode pitch, a reduced power consumption and an increased noise performance.

Figures 1, 26:
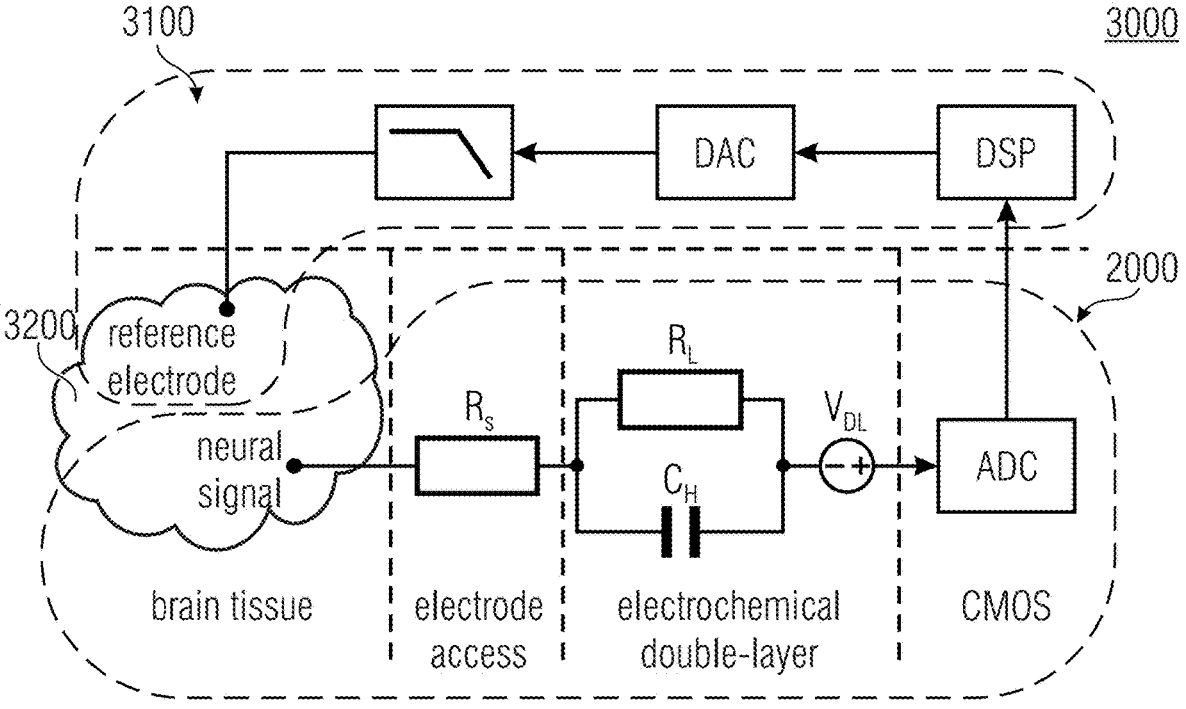
Figure 26:
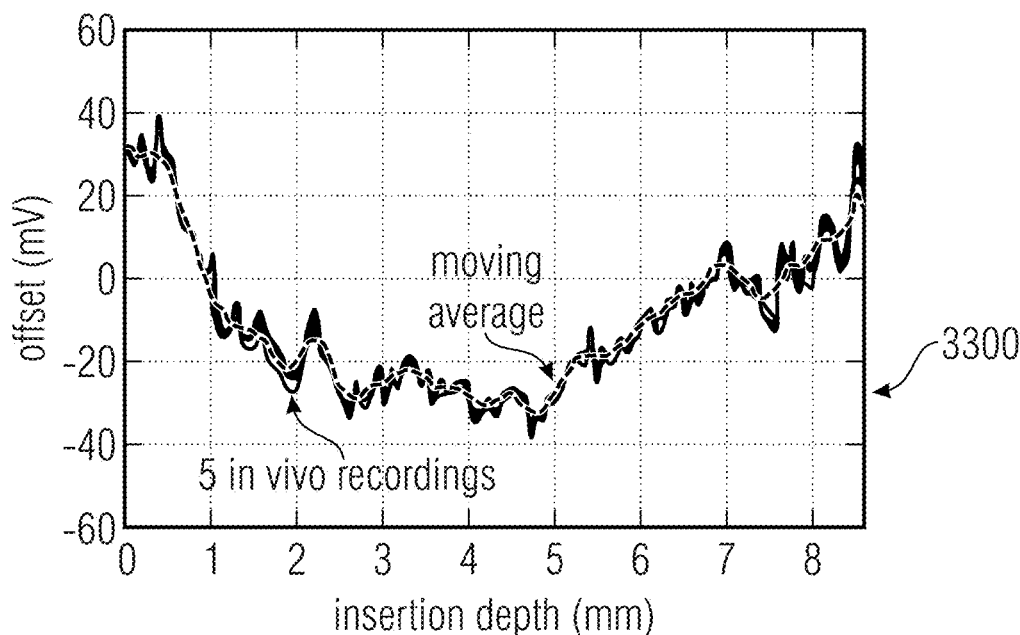
Figure 2:
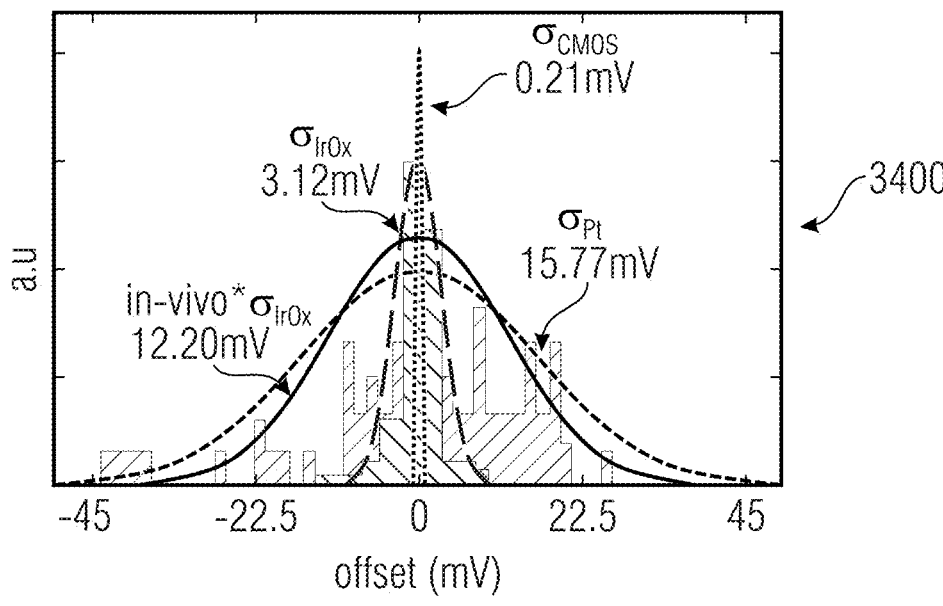

FIG. 26 shows a system 3000, e.g. a control system, comprising a sensor array 2000 and a global reference controller 3100. The global reference controller 3100 is configured to determine a mean value of all channels, i.e. recording sites 2200 of the sensor array 2000, and control a reference potential applied to tissue 3200. The diagram 3300 shows in vivo measurements in the motor cortex of a nonhuman primate using fully immersible neural probes [12]. The diagram 3300 shows a variance of the electrode offset, i.e. a local offset. As shown in the diagram 3400, a ±50 mV offset compensation is sufficient, e.g. implemented in the IDAC of the in-situ analog-to-digital converter 226 of the sensor array 2000.

Conclusions:

Neural Recording Front End based on a Two Step I$\Delta\Sigma$ ADC

Figure 27:
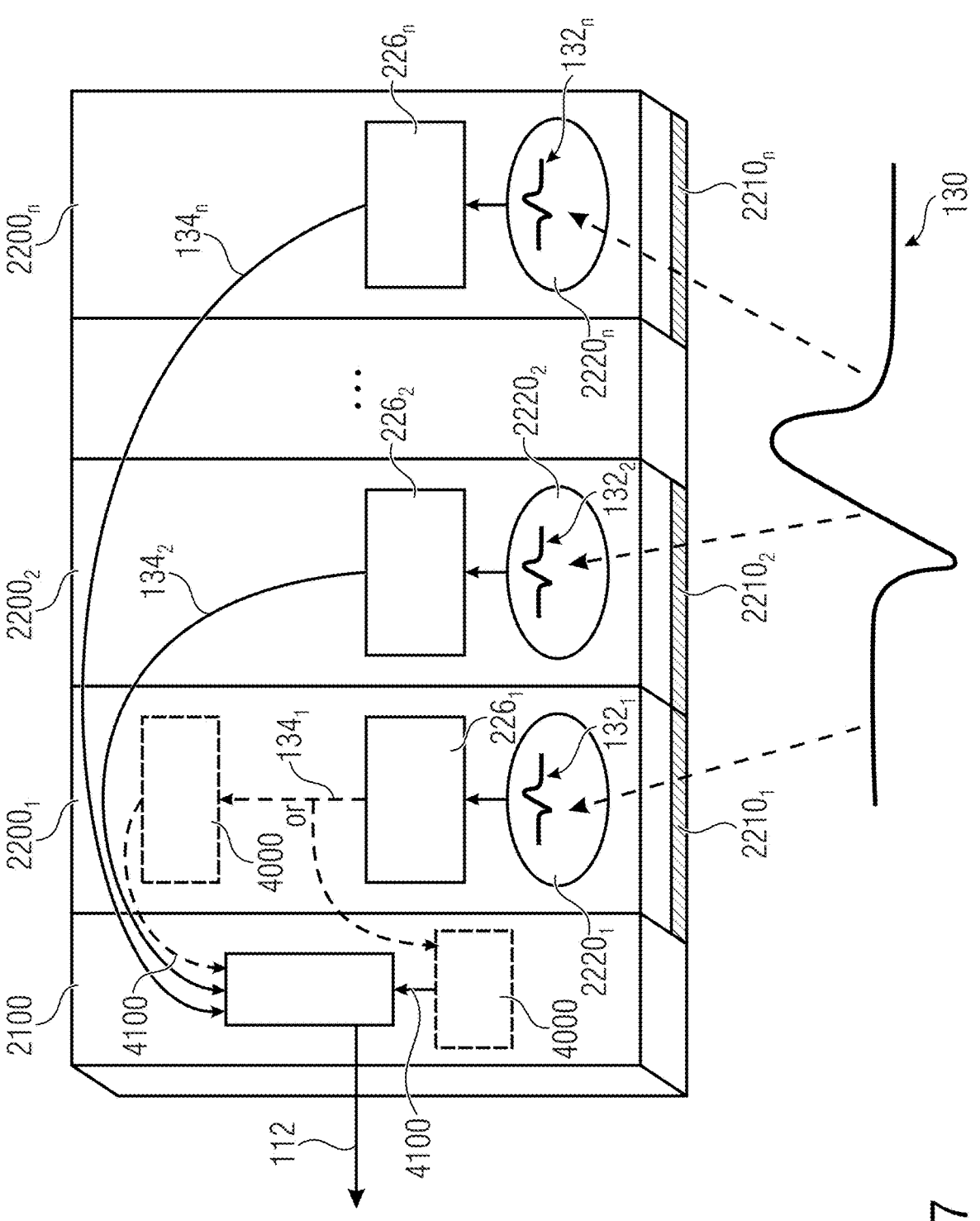
FIG. 27 shows an embodiment of a sensor array with a data compression unit.

Reduced OSR and thus power consumption at the same resolution of a first-order I$\Delta\Sigma$ ADC Minimal silicon area due to hardware reuse Fully Immersible Neural Probe Prototypes ±60 mV offset compensation/4-bit configurable Lowest power consumption for fully integrated neural probes Best noise performance for fully integrated neural probes Highly scalable with process technology and supply since up to 67% of the circuit is covered by digital cells FIG. 27 shows a sensor array 2000 comprising a base 2100 and a plurality of modular recording sites 2200. Each modular recording site 2200 of the plurality of modular recording sites comprises, a CMOS substrate 2210, at least one sensor element 2220 and an in-situ analog-to-digital converter 226. The features can have functionalities as described above with regard to one or more of the sensor arrays. However, the sensor elements 2220 are at least configured for receiving an analog signal 132 and the in-situ analog-to-digital converters 226 are at least configured for converting the respective analog signal 132 into a respective digital sensor signal 134. Especially the in-situ analog-to-digital converter 226 can be implemented in different ways described above.

The base 2100 is configured to provide a probe signal 112 based on the digital sensor signals 134 provided by the plurality of modular recording sites 2200. The base 2100 might receive from each modular recording site 2200 the respective digital sensor signals 134 and can be configured to provides same as the probe signal 112. Alternatively, the digital sensor signals 134 are further processed to obtain the probe signal 112.

Further, the sensor array 2000 comprises a data compression unit 4000, e.g. a data compressor, configured for reducing a data rate of the digital sensor signal $134_1$ obtained by a modular recording site $2200_1$ of the plurality of modular recording sites 2200. The in-situ analog-to-digital converter 226 might be configured to directly provide the digital sensor signal $134_1$ to the data compression unit 4000. Alternatively, the modular recording site 2200 and/or the base 2100 might comprise additional processing means for processing the digital sensor signal $134_1$ before providing it to the data compression unit 4000.

As shown in FIG. 27, the data compression unit 4000 can be implemented, e.g., integrated or incorporated, in the modular recording site $2200_1$ or in the base 2100.

According to an embodiment, the data compression unit 4000 is configured for determining a difference $4100a$ between a first digital sensor signal $134a_1$ obtained by the modular recording site $2200_1$ during a first instance of time $t_1$ and a second digital sensor signal $134b_1$ obtained by the modular recording site $2200_1$ during a second, later instance of time $t_2$, see FIG. 28. The data compression unit 4000, for example, is configured to superimpose the two digital sensor signals $134a_1$ and $134b_1$ to determine the difference $4100a$. The difference $4100a$ might represent a delta-signal or a residual-signal. The difference $4100a$ can be associated with the second digital sensor signal $134b_1$. In other words, the difference $4100a$ can represent a delta encoded version of the second digital sensor signal $134b_1$. Therefore, the data compression unit 4000 can also be understood as a delta encoder. The data compression unit 4000 might be configured for reducing a data rate of a present, e.g., current, digital sensor signal 134 by determining the difference $4100a$ between the present digital sensor signal 134 and a timely preceding digital sensor signal 134, wherein both digital sensor signals 134 are obtained by the same modular recording site $2200_1$. The timely preceding digital sensor signal 134 might be stored in the data compression unit 4000 and the data compression unit 4000 might be configured for replacing the timely preceding digital sensor signal 134 with the present digital sensor signal 134, e.g., after the determination of the difference $4100a$ associated with the present digital sensor signal 134, for a determination of a difference $4100a$ associated with a subsequent digital sensor signal 134 obtained by the modular recording site $2200_1$.

Figures 1, 28:
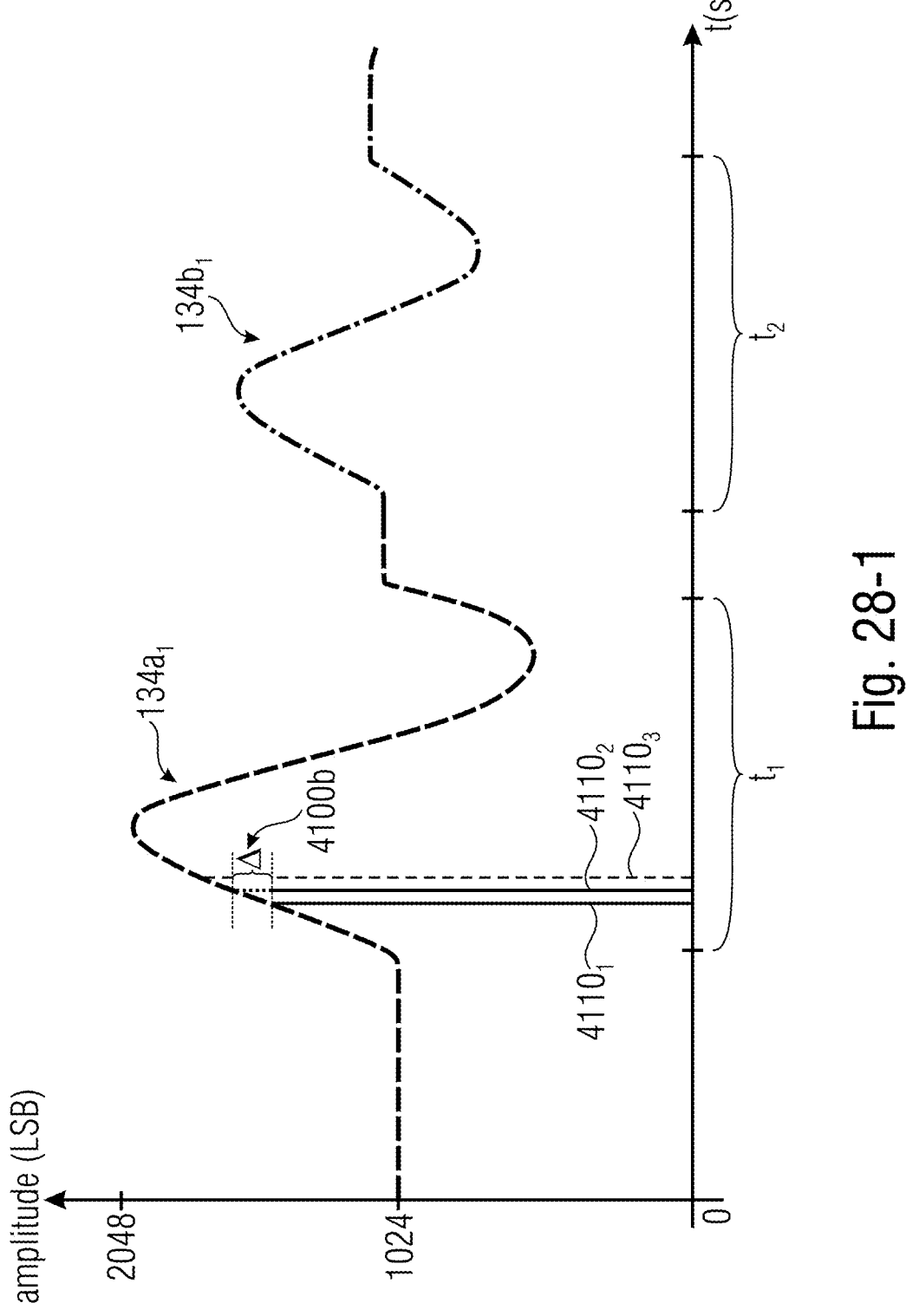
Figures 2, 28:
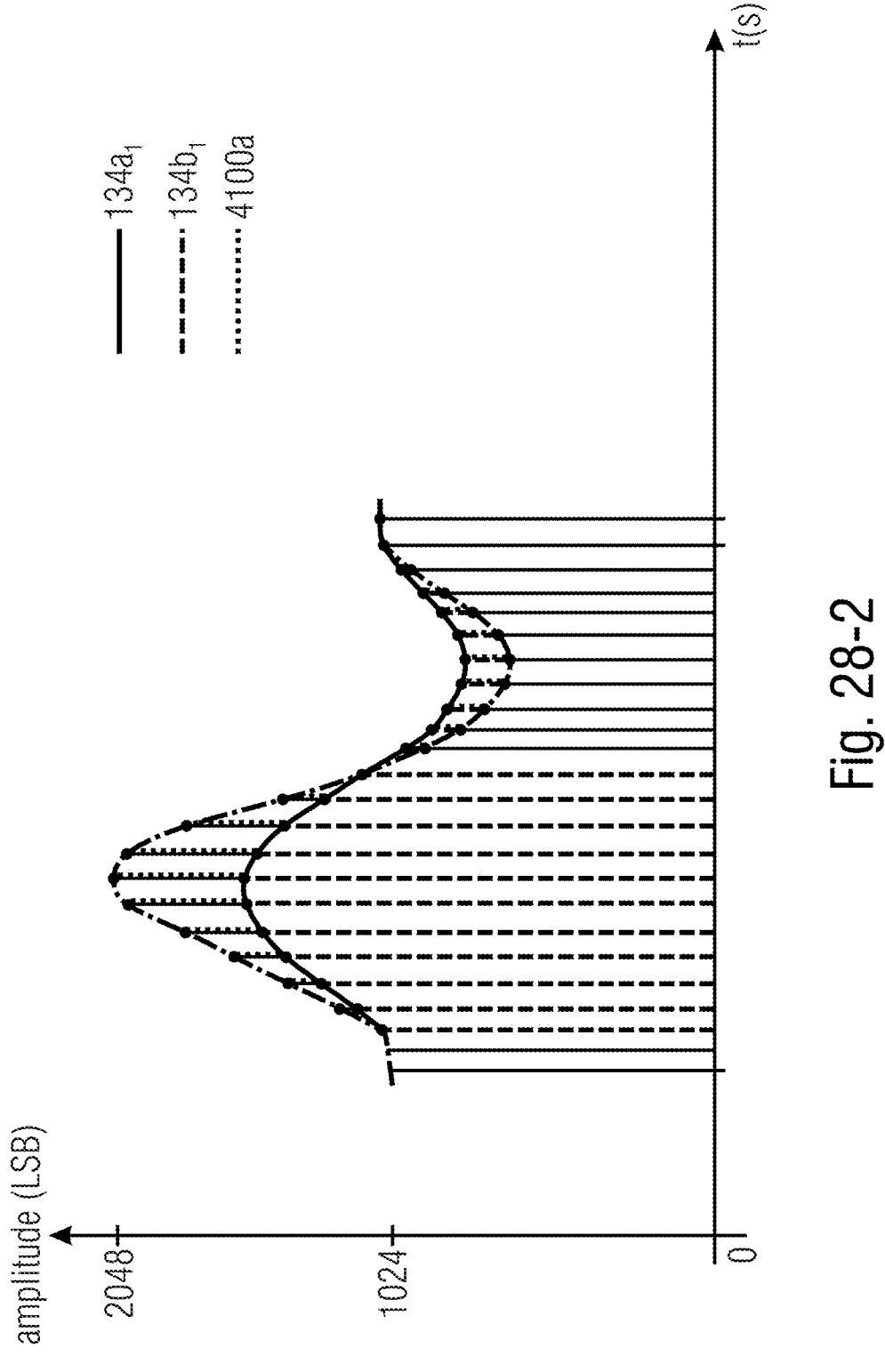

According to an alternative embodiment, also shown in FIG. 28, the data compression unit 4000 is configured for determining a difference $4100b$ between two consecutive samples $4110_1$ and $4110_2$ of the digital sensor signal $134_1$ (e.g., indicated in FIG. 28 with the reference numeral $134a_1$) obtained by the modular recording site $2200_1$. The difference $4100b$ might represent a delta-value or a residual-value. The two consecutive samples $4110_1$ and $4110_2$ are represented by a first sample $4110_1$ and a second sample $4110_2$, wherein the second sample $4110_2$ is obtained by the modular recording site $2200_1$ after the first sample $4110_1$. The difference $4100b$ can be associated with the second sample $4110_2$. In other words, the difference $4100b$ can represent a delta encoded version of the second sample $4110_2$. Therefore, the data compression unit 4000 can also be understood as a delta encoder. A timely preceding sample 4110 (e.g. the first sample $4110_1$), might be stored in the data compression unit 4000 and the data compression unit 4000 might be configured for replacing the timely preceding sample 4110 with the present sample 4110 (e.g. the second sample $4110_2$), e.g., after the determination of the difference $4100b$ associated with the present sample 4110, for a determination of a difference $4100b$ associated with a subsequent sample $4110_3$ of the digital sensor signal $134_1$.

According to an embodiment, the base 2100 is configured to provide the probe signal 112 based on the delta-signal, e.g., the difference $4100a$, or the delta-value, e.g., the difference $4100b$. Advantageously, the base 2100 is configured to provide the delta-signal, e.g., the difference $4100a$, or the delta-value, e.g., the difference $4100b$, as the probe signal 112.

According to an embodiment, the data compression unit 4000 integrated in the base 2100 can be configured to receive from each modular recording site 2200 of the plurality of modular recording sites 2200 the respective digital sensor signal 134 and reduce a respective data rate of the respective digital sensor signal 134. For each digital sensor signal 134 provided by the plurality of modular recording sites 2200, the data compression unit 4000 can be configured to obtain the difference 4100a or 4100b as described above. The difference 4100a, for example, is determined between digital sensor signals 134 obtained by and provided from the same modular recording site 2200 of the plurality of modular recording sites 2200, e.g., a difference 4100a between two consecutive digital sensor signals 134 received from the same modular recording site 2200.

According to another embodiment, a first modular recording site $2200_1$ of the plurality of modular recording sites 2200 comprises the data compression unit 4000 and a second modular recording site 22002 of the plurality of modular recording sites 2200 comprises a further data compression unit. The further data compression unit can comprise features and/or functionalities as described above with regard to the data compression unit 4000.

According to an embodiment, each modular recording site 2200 of the plurality of modular recording sites 2200 can comprise a data compression unit with the same features and/or functionalities as described above with regard to the data compression unit 4000. Thus, each modular recording site 2200 can provide the respective digital sensor signal 134 with a reduced data rate to the base 2100.

According to an embodiment, each modular recording site 2200 of the plurality of modular recording sites 2200 can further comprise a communication interface (e.g., 228, 328, 440, 460, 550 and/or 2230) as described with regard to one of the aforementioned sensor arrays. The respective communication interface might be configured to provide the respective digital sensor signal 134 or the digital sensor signal 134 with a reduced data rate to the base 2100, dependent on whether the respective modular recording site comprises a data compression unit 4000 or not.

This sensor array 2000 enables a reduction of the data rate in fully-integrated CMOS neuronal probes with local digitization based on digital delta encoding. An analysis of neuronal signals, i.e. analog signals 132, recorded during in-vivo experiments revealed that the data compression, e.g. delta encoding, performed by the data compression unit 4000 can reduce the data rate by 36% with respect to a full scale of ±11.25 mV and a resolution of 11 bit, e.g. of the in-situ analog-to-digital converter $226_1$. The delta encoding can be determined off-chip or directly integrated into a decimation filter of an in-situ analog-to-digital converter $226_1$, e.g., an incremental delta-sigma ADC, located under each sensor element 2220, e.g. under the electrodes, on the shank of the probe, i.e. the sensor array 2000. An area estimate of the filter by synthesis in a 180 nm technology resulted in a 34% reduced area when using delta encoding.

Optionally, each of one or more modular recording sites 2200 of the plurality of modular recording sites 2200 further comprises a reduction element 4200 as will be described in more detail with regard to FIG. 30.

Figure 29:
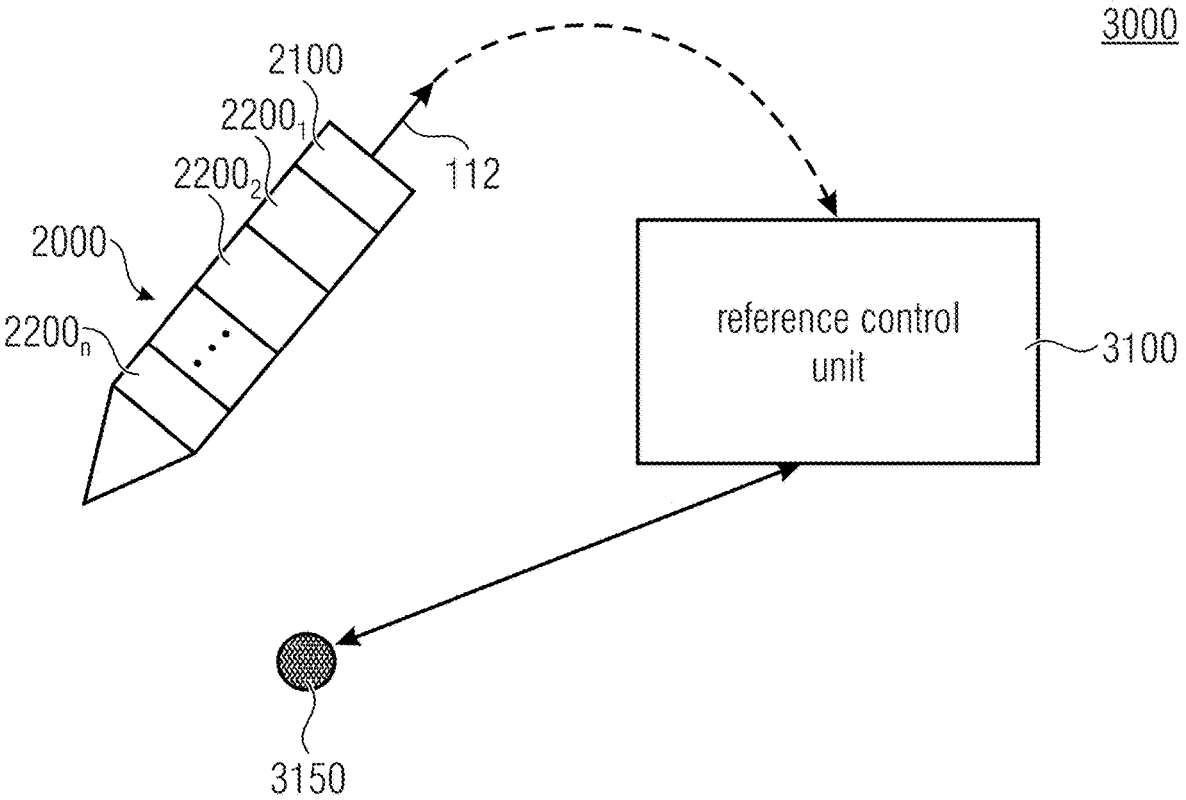
FIG. 29 shows an embodiment of a measurement system with a sensor array comprising a data compression unit.

FIG. 29 shows a measurement system 3000 comprising a sensor array 2000 as described with regard to FIGS. 27 and 28. Additionally, the measurement system 3000 comprises a reference electrode 3150 and a reference control unit 3100 configured to control a reference voltage of the reference electrode 3150. The measurements system 3000 might be configured to determine an offset compensation, which can be implemented in the in-situ analog-to-digital converters 226 of the sensor array 2000.

According to an embodiment, the data compression unit 4000 of the sensor array 2000 or a plurality of data compression units comprising the data compression unit 4000 is configured for determining, for each digital sensor signal 134 provided by the plurality of modular recording sites 2200, a respective difference 4100a or 4100b, wherein respective raw data, e.g. a reconstructed value, a reconstructed signal, a decoded value or a decoded signal, representing the respective originally received analog sensor signal 132 is determinable based on the respective difference 4100a or 4100b.

To control the potential of a reference electrode in the DC-coupled neuronal probe 2000, the uncompressed raw data, for example, are needed. Since delta coding is lossy, an initial reference sweep is presented to enable regulation. This is validated with measurements in a phosphate buffered saline.

According to an embodiment, in an initial step the reference control unit 3100 is configured to change the reference voltage of the reference electrode 3150 until, for each modular recording site 2200 of the plurality of modular recording sites 2200, the respective difference 4100a or 4100b equals zero. Then, in a further step, the reference control unit 3100 is configured to further change the reference voltage of the reference electrode 3150 with a configurable increment and obtain, for each reference voltage, an average of a plurality of the reconstructed values, and perform the further change of the reference voltage until the average of the plurality of the reconstructed values is equal to a predetermined value. It is possible that at an initialization of the initial step the delta values associated with the plurality of modular recording sites 220 are already all equal to zero. In this case, the reference control unit 3100 is configured to continue with the further step.

Figure 31:
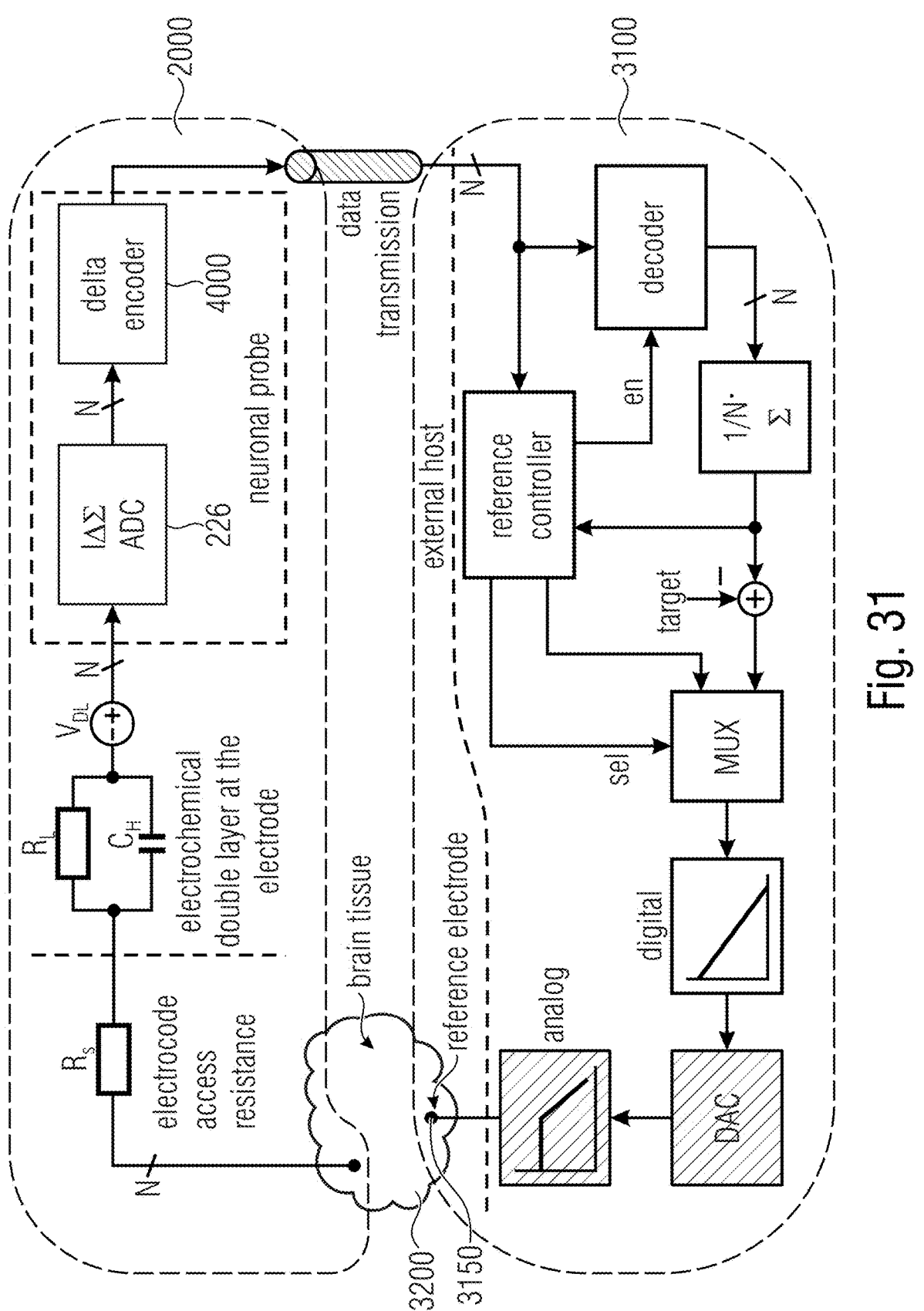
FIG. 31 shows a detailed view of a measurement system with a sensor array comprising a data compression unit.
Figure 32:
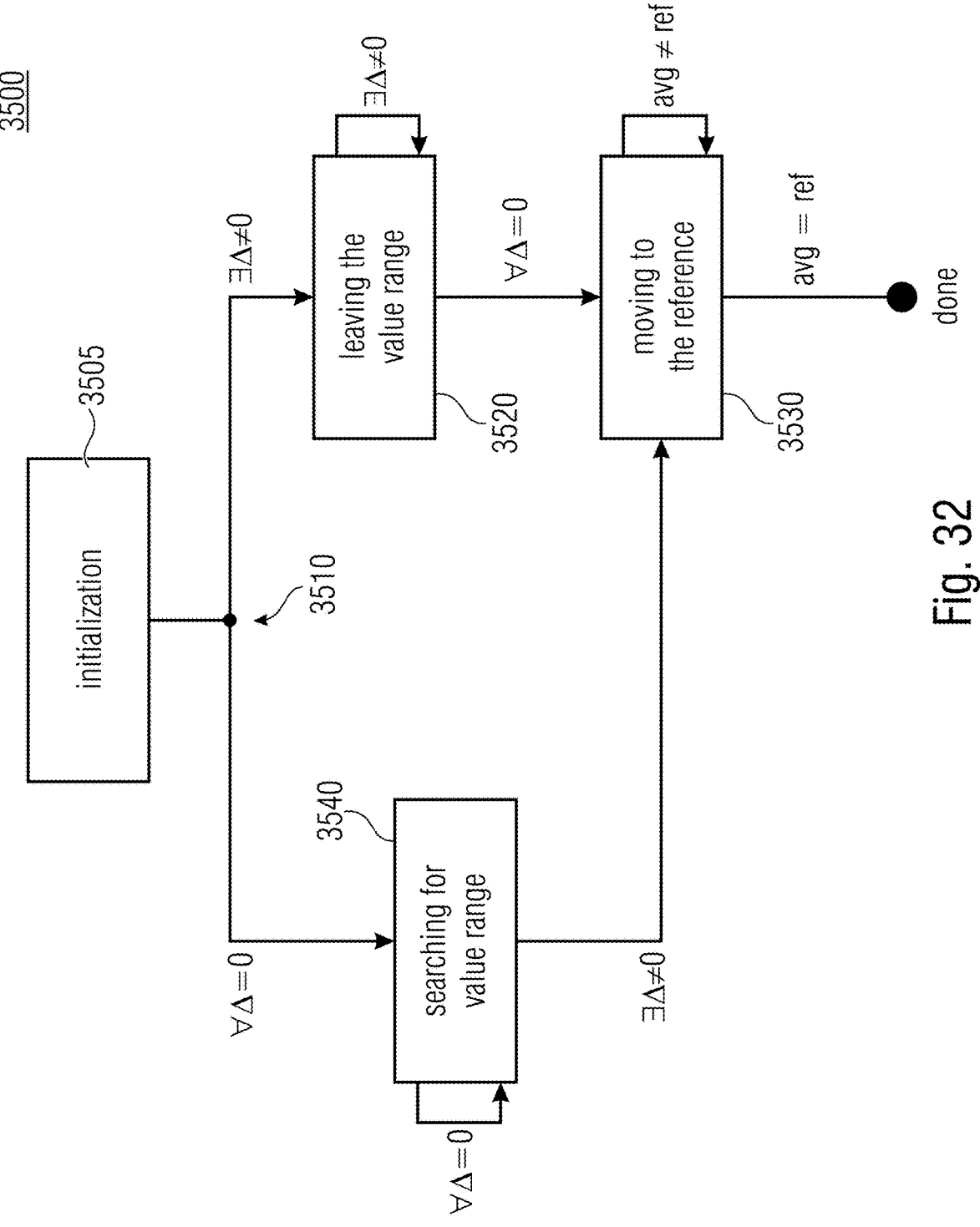
FIG. 32 shows flow diagram of an initial reference sweep.

More optional details with regard to the measurement system 3000 and the reference sweep are described with regard to FIGS. 31 and 32.

Figure 30:
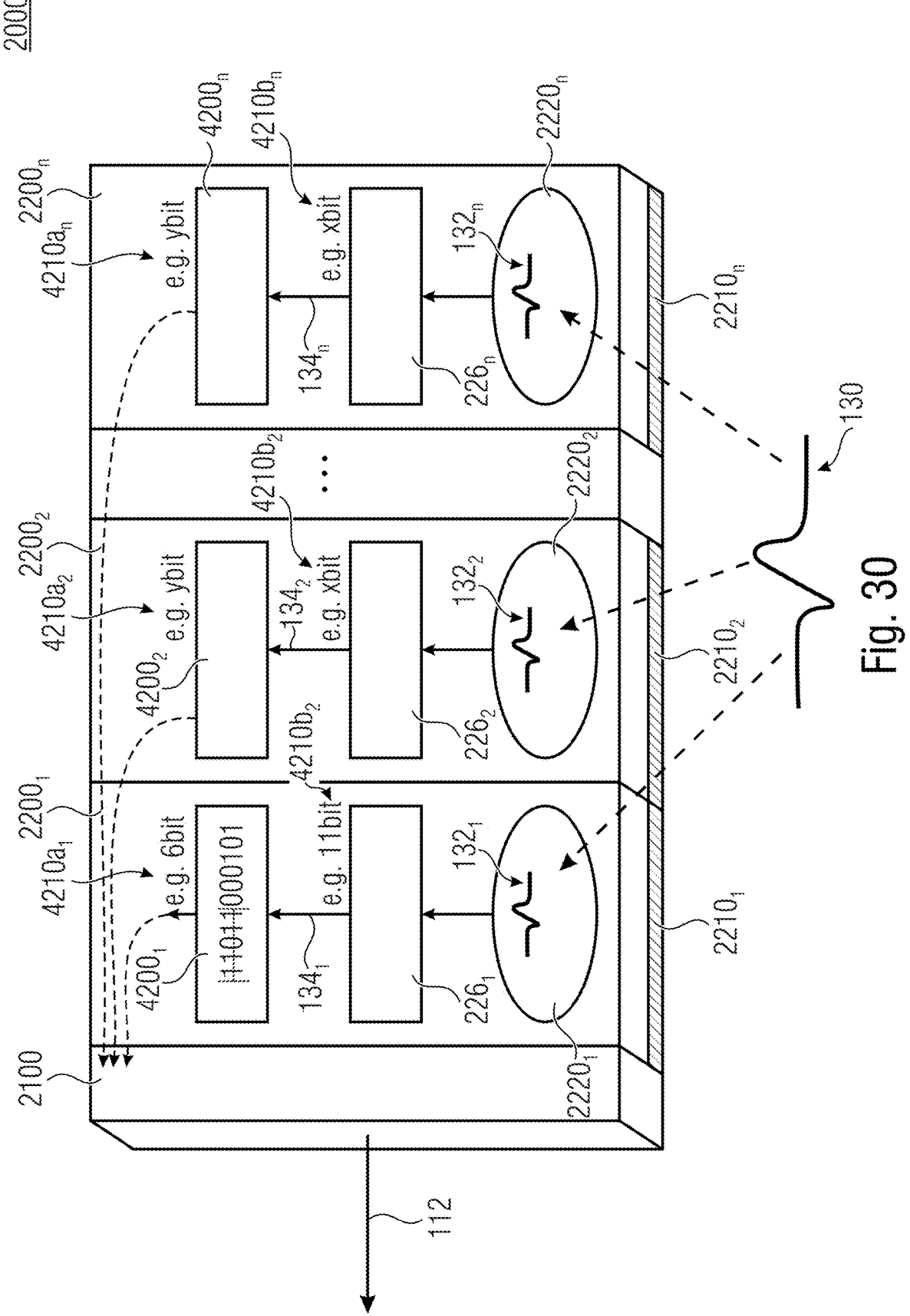
FIG. 30 shows an embodiment of a sensor array comprising a reduction element.

FIG. 30 shows a sensor array 2000 comprising a base 2100 and a plurality of modular recording sites 2200. Each modular recording site 2200 of the plurality of modular recording sites comprises, a CMOS substrate 2210, at least one sensor element 2220 and an in-situ analog-to-digital converter 226. The features can have functionalities as described above with regard to one or more of the sensor arrays. However, the sensor elements 2220 are at least configured for receiving an analog signal 132 and the in-situ analog-to-digital converters 226 are at least configured for converting the respective analog signal 132 into a digital sensor signal 134. Especially the in-situ analog-to-digital converter 226 can be implemented in different ways described above. Additionally, it is to be noted that the sensor array 2000 can comprise further features and/or functionalities of other herein described sensor arrays.

Each modular recording site 2200 of the plurality of modular recording sites further comprises a reduction element 4200 configured to reduce a word size of the respective digital sensor signal 134 provided by the respective in-situ analog-to-digital converter 226 of the respective modular recording site 2200. For example, for each modular recording site 2200, the respective reduction element 4200 can be configured to provide the respective digital sensor signals with a word size smaller than a resolution of the respective in-situ analog-to-digital converter 226. The reduced word size corresponds to a first number 4210a of bits being smaller than a second number 4210b of bits representing the resolution of the in-situ analog-to-digital converter 226, e.g. a 6 bit reduced word size at an 11 bit resolution.

According to an embodiment, for each modular recording site 2200, the respective reduction element 4200 is configured to reduce the word size of the respective digital sensor signal 134 by omitting a predefined number of high-order bits, e.g., omitting the certain number of high-order bits so that the respective digital sensor signals 134 are represented by at least 6 lower-order bits.

The herein proposed sensor arrays, especially the one described with regard to FIGS. 27 and 28, can be used to evaluate in-vivo data, as will be explained in the following in more detail:

With neuronal signals, a differentiation is conventionally made between low-frequency local field potentials (LFP, 0.5 Hz-1 kHz) and high-frequency action potentials (AP, 300 Hz-10 kHz), see [12], [16-18]. Although the value ranges of the read-out electronics of the probe are specified with ±11.25 mV, ±22.5 mV and ±45 mV in [12], they are not designed for pure neuronal signals, but they are designed to be able to cover variations of the electrochemical potential difference between the individual electrodes. However, the maximum amplitudes of the neuronal signals measurable by means of invasive methods, e.g. with a neuronal probe, are specified with 1 mV [20]. Thus, the full dynamic range of the read-out system is not required for the signals of interest, promising possible compression of the digitized neuronal signals through consideration of the delta values.

In order to be able to make a statement as to whether delta encoding is a suitable compression method for neuronal read-out systems with in-situ $\Delta\Sigma$ ADC front-end, and as to which word width, i.e. word size, in bits is sufficient for a delta data transfer, data sets from in-vivo experiments are statistically analyzed with respect to their delta values first. The statistical parameters (standard deviation a and maximum delta values $\Delta_{max}$), the value range (FS) and the least-significant bit (LSB) of the evaluated raw data with a sampling rate of 20 kHz are given in Table 1. The data sets nc-m1, nc-m2, and nc-m3 were recorded with fully immersible CMOS probes [12] in the motor cortex of non-human primates, and the data set HC2 (ec013.527) [21] was recorded in the hippocampus of rats.

TABLE 1

| Statistical analysis of raw data from available in-vivo experiments recorded at a sampling rate of 20 kHz. | | | | |
|---|---|---|---|---|
| data set | FS (mV) | LSB (µV) | $\sigma$ (µV) | $\Delta_{max}$ (µV) |
| nc-m1 | ±11.25 | 11 | 20.3 | 275 |
| nc-m2 | ±22.5 | 22 | 22.9 | 176 |
| nc-m3 | ±45 | 44 | 27.5 | 176 |
| hc2 | 20 | 0.3 | 9.32 | 343 |

However, the standard deviation is not meaningful in this case, since, even when considering a range of 12σ, not all of the maximum delta values are reached. The latter are associated with the APs, which becomes apparent through digital post-processing of the raw data, i.e. band-pass filtering in the corresponding frequency range. Due to the refractory period of a neuron, APs occur only sporadically with a frequency limit of approximately 500 Hz; however, due to their characteristic shape they have larger rates of change. On the other hand, LFPs only change slowly, which is why the standard deviation is low and the maximum delta value is large in comparison. With delta encoding, it has to be ensured that the maximum signal change can be detected. According to the data evaluation in Table 1, this is possible for a maximum delta value of 343 µV with a 6-bit data word plus a sign bit, i.e. with a word size corresponding to a number of bits being 6 plus the sign bit. In this case, reference is made to a probe, i.e. a sensor array 2000, with a value range of ±11.25 mV and a resolution of 11 bits [12]. Accordingly, signal change rates of approximately 700 µV/sample can be detected, and the data rate can be reduced by 36%.

FIG. 31 shows a neuronal read-out system with N channels, i.e. modular recording sites 2200, based on I$\Delta\Sigma$ ADC 226 front-end with delta encoding, e.g. performed by the data compression unit 4000, in each recording channel. The global reference 3150 is controllable with the delta values. The full neuronal read-out system, e.g. the measurement system 3000, comprising a probe, e.g. the sensor array 2000, with an in-situ I$\Delta\Sigma$ ADC front-end, as well as delta encoding integrated in each recording channel and an external reference closed-loop control, e.g., the reference control unit 3100, is illustrated in FIG. 31. The delta encoding integrated in each recording channel is, e.g., realized by a plurality of data compression units 4000, wherein each data compression unit 4000 is integrated in a modular recording site 2200 of the sensor array 2000, e.g., so that each modular recording site 2200 of the plurality of modular recording sites comprises a data compression unit 4000. The reference control unit 3100 is used to compensate the electrochemical potential difference between the tissue 3200 and the input of the electric read-out system [12] and [18], e.g., the analog signals 132 received from the sensor elements 2220, in order to ensure that the neuronal signals, i.e. the analog signals 132, are in the value range of the ADCs, i.e. the in-situ analog-to-digital converters 226. To this end, the decoded mean value of all, or selected, channels (e.g. modular recording sites 2200) is determined, and a compensation voltage is applied to the reference electrode 3150 via an integrated controller, e.g. the reference control unit 3100. With respect to the input and output signals of the front-end, the digital integrator leads to a high-pass behavior in the closed-loop control system. By setting the amplification of the integrator, the cut-off frequency of the high-pass filter can be controlled, and mutual signals of the read-out channels, such as the half-cell potential of the electrodes 2220, can be compensated up to a desired frequency.

However, delta encoding is a lossy compression method, only containing information about time-varying signals. For AC-coupled read-out systems [16, 17], this loss of information would not be relevant, however, this information is required for DC-coupled systems with such a reference closed-loop control [12] and [18]. Information with respect to a DC portion or an initial offset is lost, said information being essential to correctly closed-loop control the compensation voltage. In order to ensure the functionality of the reference closed-loop control in combination with delta encoding, an initial reference sweep 3500 is performed according to the flow diagram in FIG. 32. To this end, decoding is initially deactivated, and it is verified 3510 whether one of the read-out channels, i.e. one of the plurality of modular recording sites 2200, transfers a non-zero delta value. If this is the case, the compensation voltage, i.e. the reference voltage, is controlled 3520 in one direction until all delta values correspond to zero, i.e. all channels are outside of the value range of the ADC 226. Subsequently 3530, the start value for decoding is set according to the direction of the closed-loop control, decoding is activated and is closed-loop controlled with a fixed increment into the opposite direction until the decoded mean value, i.e. an average of reconstructed values, corresponds to the desired target value. In the case of all delta values initially corresponding to zero, decoding can be activated at the start already; however, the value range of the ADCs 226 has to be searched for 3540, since the electrochemical potential varies with the material of the reference 3150 and capturing electrodes, i.e. the sensor elements 2220, as well as with the pH value of the tissue 3200. To this end, control is carried out with a specified increment into one direction until a non-zero delta value is transferred. The start value for decoding is set accordingly and is closed-loop controlled to the target value 3530. The aforementioned encoding corresponds to the reduction of the data rate of the digital sensor signal 134 obtained by a modular recording site 2200 by the data compression unit 4000 and the decoding corresponds to a reconstruction of the digital sensor signal 134 based on the digital sensor signal with the reduced data rate, e.g. the difference 4100. Such an encoding and decoding can be performed for all digital sensor signals 134 provided by the plurality of modular recording sites 2200.

In other words, at the reference sweep 3500, the reference control unit 3100 is configured to control the reference voltage of the reference electrode 3150 by applying in an initial step 3505 a predetermined reference voltage to the reference electrode 3150, obtaining from the data compression unit 4000, for each modular recording site 2200 of the plurality of recording sites 2200, the respective difference 4100, so that a plurality of differences 4100 is obtained, checking 3510 whether all differences 4100 of the plurality of differences 4100 are equal to zero, and if all differences of the plurality of differences are equal to zero, the reference control unit 3100 is configured to change 3540 the reference voltage in a first direction with a configurable increment until at least one difference 4100 unequal to zero is obtained from the data compression unit 4000, and then continue changing 3530 the reference voltage in the first direction and obtain an average of signals reconstructed based on the plurality of differences 4100 determined by the data compression unit 4000 until the average is equal to a predetermined value, and optionally then automatically perform the reference control (e.g., P, I, D, PI, PD, or PID control), i.e., direction and increment are no longer predetermined;

if at least one of the plurality of differences 4100 is unequal to zero, the reference control unit 3100 is configured to change 3520 the reference voltage in a second direction with a configurable increment until for each modular recording site 2200 of the plurality of modular recording sites 2200, a difference 4100 equal to zero is obtained from the data compression unit 4000, and then change 3530 the reference voltage in a direction opposite to the second direction and obtain an average of signals reconstructed based on the plurality of differences 4100 determined by the data compression unit 4000 until the average is equal to the predetermined value, and optionally then automatically perform the reference control (e.g., P, I, D, PI, PD, or PID control), i.e., direction and increment are no longer predetermined.

Figures 33A, 33B:
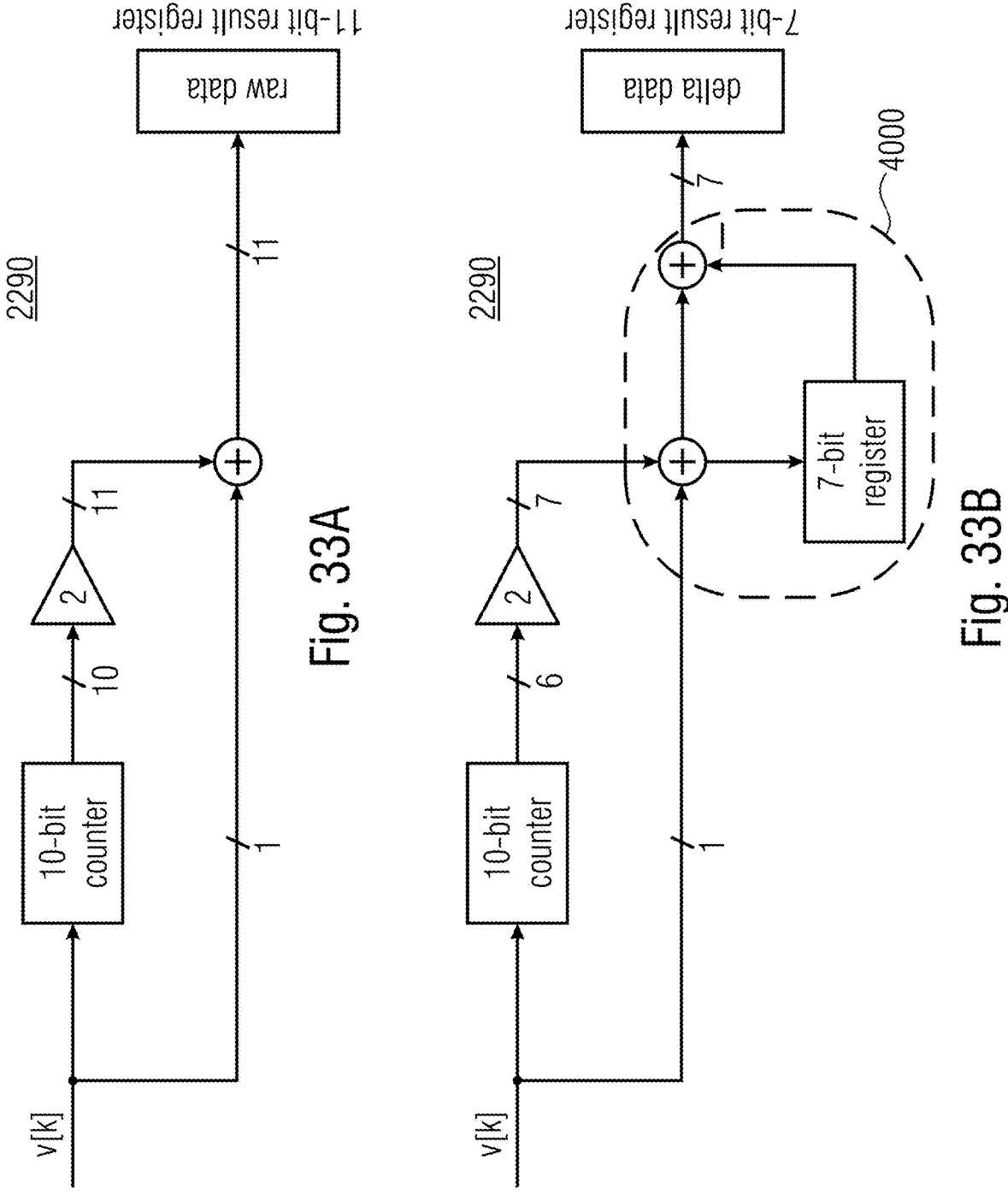
FIG. 33$a$ shows a conventional decimation filter of a first-order $I\Delta\Sigma$ ADC.

As is illustrated in FIG. 33(*a*), the decimation filter 2290 of a first-order IΔΣ ADC with a resolution of 11 bits may be realized with a simple up-counter and a result register [12]. The latter is required for transferring the data to the base

2100. However, as is illustrated in FIG. 33(*b*), delta encoding may be directly integrated into the decimation filter 2290. According to the embodiment shown in FIG. 33(*b*), the data compression unit 4000 can be integrated in the decimation filter 2290 of the in-situ analog-to-digital converter 226 of the modular recording site 2200. In this case, an area estimation by means of synthesis of the digital implementation resulted in 1859 μm$^2$ for 7 bit encoding, i.e. an increase of the area of the filter of approximately 21% in a 180 nm CMOS technology. Instead of the direct integration of delta encoding 4000 into the decimation filter 2290, the same may also be determined outside of the probe 2000. However, this does not require 11 bits of the raw data, i.e. the digital sensor signal 134, to be transferred; the 7 LSBs are sufficient, since the transfer bit exclusively influences the higher-value bits when calculating the delta values. According to the two's complement, this allows a signal change in the range of $(-2^6, \ldots, 0, \ldots 2^6-1) \cdot$LSB to be covered, and the decimation filter 2290 in FIG. 33(*a*) may be realized with a 6-bit up-counter and a 7-bit result register. Such a decimation filter 2290 can correspond to the reduction element 4200 mentioned in FIG. 30. An area estimation by means of synthesis of this digital implementation resulted in 999 μm$^2$, i.e. an area decrease of ~34% compared to the conventional filter.

Figure 34:
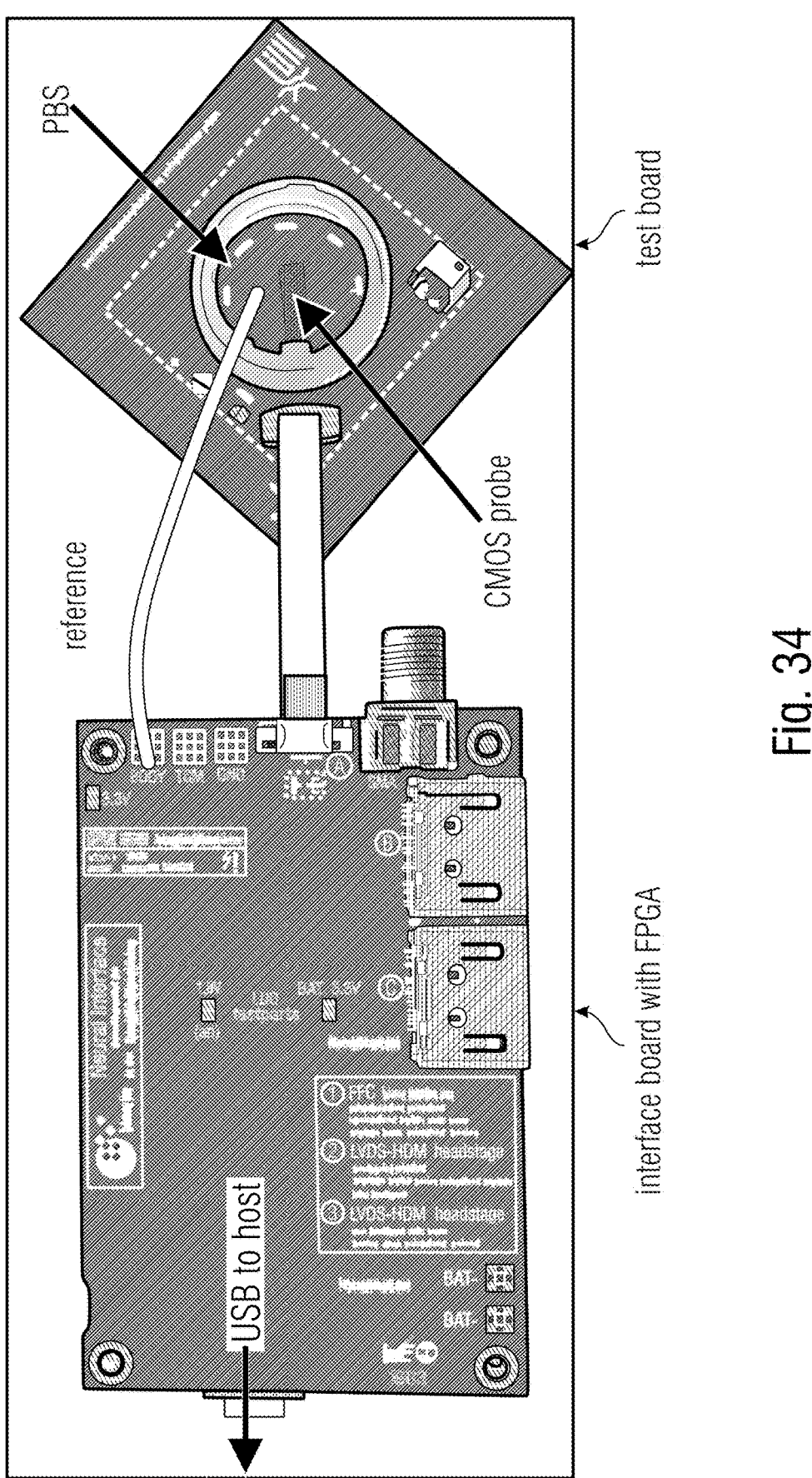
FIG. 34 shows a schematic view of a measurement system with a sensor array comprising a data compression unit.

To validate the concept of the delta transfer with reference closed-loop control and the initial reference sweep, the concept described in connection with FIGS. 29, 31 and 32 was implemented on a field-programmable gate array (FPGA), and was tested with a neuronal CMOS probe 2000 [12] in a phosphate-buffered saline (PBS) according to the setup in FIG. 34. FIG. 34 shows a measurement setup consisting of an interface board with a Spartan-6 FPGA, a flexible cable for the data transfer between the probe and the FPGA, and a test board with a neuronal CMOS probe in PBS.

Figure 35:
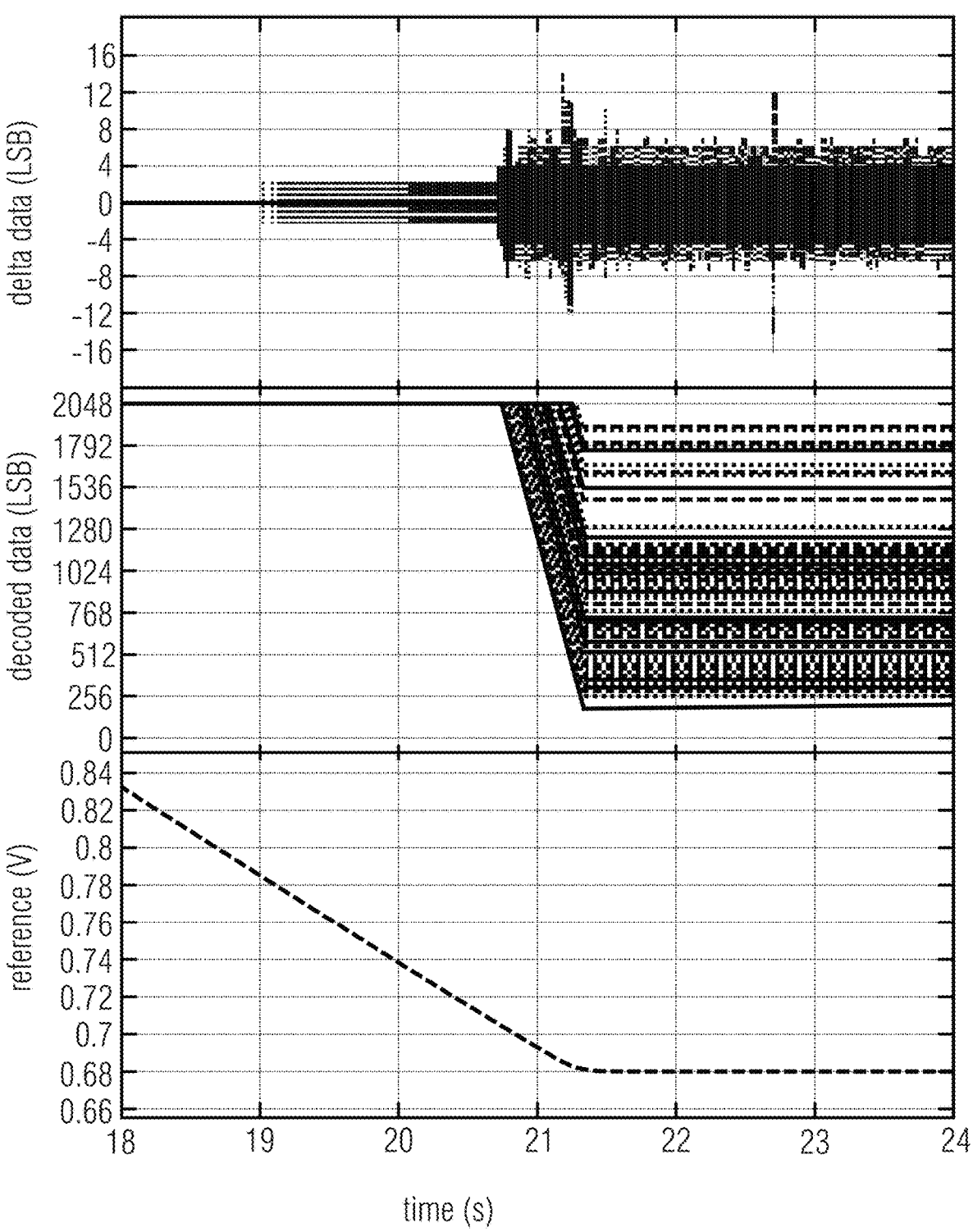
FIG. 35 shows measurement result obtained with the setup shown in FIG. 34.

In case of the probe 2000 used, since a decimation filter 2290 is integrated on the shank in each of the 144 channels 2200, the 11 bits of raw data 134 were initially transferred from the probe 2000 to the FPGA, and the delta values 4100 for controlling the reference voltage were determined there. The encoded and decoded data as well as the voltage at the reference electrode 3150 during the initial reference sweep 3500 are illustrated in the measurement results in FIG. 35, and they validate the proposed concept. FIG. 35 shows measurements with a neuronal CMOS probe with 144 channels and a value range of ±11.25 mV [12] in PBS using delta encoding and the initial reference sweep 3500 implemented on the FPGA. In this case, in the initialization 3505, all input signals were outside of the value ranges of the capturing channels 2200, which were configured in the ±11.25 mV mode. Initially, the reference voltage was 1.7 V, and it was 0.68 V in the compensated state.

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus. Some or all of the method steps may be executed by (or using) a hardware apparatus like, for example, a microprocessor, a programmable computer or an electronic circuit. In some embodiments, one or more of the most important method steps may be executed by such an apparatus.

Depending on certain implementation requirements, embodiments of the invention can be implemented in hardware or in software. The implementation can be performed using a digital storage medium, for example, a floppy disk, a DVD, a Blu-Ray, a CD, a ROM, a PROM, an EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may, for example, be stored on a machine-readable carrier.

Other embodiments comprise the computer program for performing one of the methods described herein, stored on a machine-readable carrier.

In other words, an embodiment of the inventive method is, therefore, a computer program having a program code for performing one of the methods described herein, when the computer program runs on a computer.

A further embodiment of the inventive methods is, therefore, a data carrier (or a digital storage medium, or a computer-readable medium) comprising, recorded thereon, the computer program for performing one of the methods described herein. The data carrier, the digital storage medium or the recorded medium are typically tangible and/or non-transitionary.

A further embodiment of the inventive method is, therefore, a data stream or a sequence of signals representing the computer program for performing one of the methods described herein. The data stream or the sequence of signals may, for example, be configured to be transferred via a data communication connection, for example, via the Internet.

A further embodiment comprises a processing means, for example, a computer, or a programmable logic device, configured to or adapted to perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example, a field programmable gate array) may be used to perform some or all of the functionalities of the methods described herein. In some embodiments, a field programmable gate array may cooperate with a microprocessor in order to perform one of the methods described herein. Generally, the methods are performed by any hardware apparatus.

The apparatus described herein may be implemented using a hardware apparatus, or using a computer, or using a combination of a hardware apparatus and a computer.

The apparatus described herein, or any components of the apparatus described herein, may be implemented at least partially in hardware and/or in software.

The methods described herein may be performed using a hardware apparatus, or using a computer, or using a combination of a hardware apparatus and a computer.

The methods described herein, or any components of the apparatus described herein, may be performed at least partially by hardware and/or by software.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

REFERENCES

[1] G. Buzsaki et al., "Tools for Probing Local Circuits: High-Density Silicon Probes Combined with Optogenetics," Neuron, vol. 86, pp. 92-105, 2015.

[2] K. Seidl, M. Schwaerzle, I. Ulbert, H. P. Neves, O. Paul and P. Ruther, "CMOS-Based High-Density Silicon Microprobe Arrays for Electronic Depth Control in Intracortical Neural Recording—Characterization and Application," in Journal of Microelectromechanical Systems, vol. 21, no. 6, pp. 1426-1435, December 2012.

[3] A. S. Herbawi et al., "High-density CMOS neural probe implementing a hierarchical addressing scheme for 1600 recording sites and 32 output channels," Transducers, pp. 20-23, 2017.

[4] V. Viswam et al., "High-density mapping of brain slices using a large multi-functional high-density CMOS microelectrode array system," Transducers, pp. 135-138. 2017, doi: 10.1109/TRANSDUCERS.2017.7994006

[5] C. M. Lopez et al., "22.7 A 966-electrode neural probe with 384 configurable channels in 0.13 $\mu$m SOI CMOS," ISSCC Dig. Tech. Papers, pp. 392-393, 2016.

[6] B. C. Raducanu et al, "Time multiplexed active neural probe with 678 parallel recording sites", IEEE ESSDERC, 2016, pp. 385-388.

[7] F Heer, W Franks, A Blau, S Taschini, C Ziegler, A Hierlemann, H Baltes, "CMOS microelectrode array for the monitoring of electrogenic cells", Biosensors and Bioelectronics, vol. 20, pp. 358-366, 2004, ISSN 0956-5663, doi: 10.1016/j.bios.2004.02.006.

[8] J. Scholvin et al., "Close-packed silicon microelectrodes for scalable spatially oversampled neural recording", IEEE Trans. Biomed. Eng., vol. 63, pp. 120-130, 2016.

[9] T. D. Y. Kozai and A. L. Vazquez, "Photoelectric Artefact from Optogenetics and Imaging on Microelectrodes and Bioelectronics: New Challenges and Opportunities," J. Mater. Chem. B, pp. 4965-4978, 2015.

[10] S. Tao and A. Rusu, "A Power-Efficient Time-continuous Incremental Sigma-Delta ADC for Neural Recording Systems," in IEEE Transactions on Circuits and Systems I: Regular Papers, vol. 62, no. 6, pp. 1489-1498, June 2015, doi: 10.1109/TCSI.2015.2418892.

[11] S. Park et al., "Modular 128-Channel—Analog Front-End Architecture Using Spectrum Equalization Scheme for 1024-Channel 3-D Neural Recording Microsystems", IEEE JSSC, vol. 53, no. 2, pp. 501-514, February 2018.

[12] D. De Dorigo et al., "Fully Immersible Subcortical Neural Probes With Modular Architecture and a Delta- Sigma ADC Integrated Under Each Electrode for Parallel Readout of 144 Recording Sites," IEEE JSSC, vol. 53, no. 11, pp. 3111-3125, 2018.

[13] Patent: WO2019154989—SENSOR ARRAYS, METHOD FOR OPERATING A SENSOR ARRAY AND A COMPUTER PROGRAM FOR PERFORMING A METHOD FOR OPERATING A SENSOR ARRAY

[14] Patent: U.S. Pat. No. 5,410,310—METHOD AND APPARATUS FOR EXTENDING THE RESOLUTION OF A SIGMA-DELTA TYPE ANALOG TO DIGITAL CONVERTER

[15] Y. Zhang et al., "A 16 b Multi-Step Incremental Analog-to-Digital Converter With Single-Opamp Multi-Slope Extended Counting", IEEE JSSC, vol. 52, no. 4, pp. 1066-1076, April 2017.

[16] C. M. Lopez et al., A Neural Probe With Up to 966 Electrodes and Up to 384 Configurable Channels in 0.13 µm SOI CMOS, IEEE Trans. Biomed. Circuits Syst., vol. 11, no. 3, pp. 510-522, June 2017

[17] B. C. Raducanu et al., Time Multiplexed Active Neural Probe with 1356 Parallel Recording Sites. Sensors (Basel, Switzerland), 2017 Oct. 19; 17(10):2388.

[18] D. Wendler et al., 28.7 A 0.00378 mm2 Scalable Neural Recording Front-End for Fully Immersible Neural Probes Based on a Two-Step Incremental Delta-Sigma Converter with Extended Counting and Hardware Reuse, 2021 IEEE International Solid-State Circuits Conference (ISSCC), 2021, pp. 398

[19] S. Kim et al., Thermal impact of an active 3-D micro-electrode array implanted in the brain, IEEE Trans. Neural Syst. Rehabil. Eng., vol. 15, no. 4, pp. 493-501, 2007

[20] Rikky Muller, Brain-computer interfaces: Fundamentals to future technologies, 2021 IEEE International Solid-State Circuits Conference (ISSCC) Tutorial

[21] Collaborative Research in Computational Neuroscience—Data sharing, web: https://crcns.org/(besucht am 03/02/2021)

The invention claimed is:

1. A sensor array comprising:
a base for providing a probe signal; and
a plurality of modular recording sites, wherein each modular recording site of the plurality of modular recording sites comprises:
a CMOS substrate;
at least one sensor element configured for receiving an analog signal;
an in-situ analog-to-digital converter configured for converting the analog signal into a digital sensor signal; and
a communication interface configured to provide the digital sensor signal to the base,
wherein communication interfaces of the plurality of modular recording sites are connected serially with respect to each other and to the base, and
wherein the in-situ analog-to-digital converter is configured to operate in a first operating mode of performing a first quantization of the analog signal using a first quantization setting and acquiring a residual error from the first quantization and to operate in a second operating mode of performing a second quantization of the residual error using a second quantization setting which is different from the first quantization setting of the in-situ analog-to-digital converter.

2. The sensor array of claim 1, wherein the in-situ analog-to-digital converter represents a continuous-time incremental delta-sigma converter.

3. The sensor array according to claim 1, wherein the first quantization represents a coarse quantization and the second quantization represents a fine quantization.

4. The sensor array according to claim 1, wherein each in-situ analog-to-digital converter comprises a signal input and is configured for providing a connection between the signal input and the analog signal in the first operating mode and for disconnecting the signal input from the analog signal in the second operating mode.

5. The sensor array according to claim 1, wherein the first operating mode and the second operating mode differ from each other in view of an amplification applied in a feedback loop of a delta-sigma modulator of the in-situ analog-to-digital converter, a sampling rate of the delta-sigma modulator, or of a signal shape applied for sampling in the delta-sigma modulator.

6. The sensor array according to claim 1, wherein in the second operating mode an integrator and/or a quantizer and/or a feedback DAC of a delta-sigma modulator of an analog-to-digital-converter is reused with respect to the first operating mode.

7. The sensor array according to claim 1, wherein a delta-sigma-modulator of a digital-to-analog converter is implemented in absence of an input-feedforward path.

8. The sensor array according to claim 1, wherein the communication interface is configured to receive configuration data from the base, and wherein the each modular recording site is configured for adapting a parameter relating to an operation of the each modular recording site based on the received configuration data.

9. The sensor array according to claim 1, wherein the communication interface comprises a serial interface, wherein the communication interfaces of the plurality of modular recording sites are connected to each other in a serial communication chain comprising a forward path from the base to an endpoint of the sensor array and a backward path from the endpoint of the sensor array to the base, and wherein for each pair of a first modular recording site and a neighboring second modular recording site, the communication interface of the first modular recording site is connected to the forward path and the communication interface of the neighboring second modular recording site is connected to the backward path.

10. The sensor array according to claim 1, wherein a first subset of the plurality of modular recording sites is arranged on a first CMOS substrate, wherein an adjacent and neighboring second subset of the plurality of modular recording sites is arranged on a second CMOS substrate, and wherein the first CMOS substrate and the second CMOS substrate are spaced apart from each other by a gap and electrically connected to each other by at least one conductive line.

11. The sensor array according to claim 1, wherein the base comprises a wired output interface for providing the probe signal, and wherein a number of channels of the wired output interface is independent of a number of the plurality of modular recording sites and independent of a cross section of the plurality of modular recording sites in a plane perpendicular to an axial extension of the sensor array.

12. The sensor array according to claim 1, wherein the plurality of modular recording sites is arranged between the base and an endpoint of the sensor array, and wherein the sensor array forms a needle.

13. The sensor array according to claim 1, wherein at least one modular recording site of the sensor array is configured for sampling the analog signal with at least a first and a second sensor element and for multiplexing outputs of the first and the second sensor element into the digital sensor signal.

14. The sensor array according to claim 1, further comprising, in each modular recording site, an offset compensation circuit configured for compensating an offset in the analog signal as a biosignal.

15. The sensor array according to claim 1, further comprising a data compression unit configured for reducing a data rate of the digital sensor signal acquired by a modular recording site of the plurality of modular recording sites;

wherein the data compression unit is configured for determining a difference between a first digital sensor signal acquired by the modular recording site during a first instance of time and a second digital sensor signal acquired by the modular recording site during a second, later instance of time.

16. The sensor array according to claim 15, wherein the base comprises the data compression unit and wherein the data compression unit is configured to reduce a respective data rate of each digital sensor signal provided from the plurality of modular recording sites to the base.

17. The sensor array according to claim 15, wherein the modular recording site comprises the data compression unit.

18. The sensor array according to claim 13, wherein each modular recording site comprises a reduction element configured to reduce a word size of the digital sensor signal provided by the in-situ analog-to-digital converter, and wherein, for each modular recording site, the reduction element is configured to reduce the word size of the digital sensor signal by omitting a predefined number of high-order bits.

19. An analog-to-digital converter comprising a continuous-time delta-sigma modulator configured to operate in a first operating mode of performing a first quantization of an analog signal using a first quantization setting and acquiring a residual error from the first quantization and to operate in a second operating mode of performing a second quantization of the residual error using a second quantization setting which is different from the first quantization setting.

20. A neuronal probe comprising the analog-to-digital converter according to claim 19 and an offset compensation circuit, the offset compensation circuit configured for compensating an offset in the analog signal.

21. A method for operating a sensor array, wherein the sensor array comprises:

a base for providing a probe signal; and a plurality of modular recording sites, wherein each modular recording site of the plurality of modular recording sites comprises:

a CMOS substrate;

at least one sensor element configured for receiving an analog signal;

an in-situ analog-to-digital converter configured for converting the analog signal into a digital sensor signal; and a communication interface configured to provide the digital sensor signal to the base, wherein communication interfaces of the plurality of modular recording sites are connected serially with respect to each other and to the base, wherein the in-situ analog-to-digital converter is configured to operate in a first operating mode of performing a first quantization of the analog signal using a first quantization setting and acquiring a residual error from the first quantization and to operate in a second operating mode of performing a second quantization of the residual error using a second quantization setting which is different from the first quantization setting of the in-situ analog-to-digital converter, and wherein the method comprises:

recording of a signal with a sensor of a modular recording site of the plurality of modular recording sites of the sensor array;

converting of the signal into a plurality of digital sensor signals using the plurality of modular recording sites of the sensor array by operating each analog-to-digital converter in the first operating mode and in the second operating mode to acquire the digital sensor signal;

providing of the plurality of digital sensor signals to the base of the sensor array using the communication interfaces of the plurality of modular recording sites of the sensor array;

receiving of the plurality of digital sensor signals from the plurality of modular recording sites of the sensor array with the base of the sensor array;

processing of the plurality of digital sensor signals by the base of the sensor array so as to acquire the probe signal; and providing the probe signal with the base of the sensor array for a remote device.

* * * * *